US012146199B2

(12) United States Patent
Yang et al.

(10) Patent No.: US 12,146,199 B2
(45) Date of Patent: Nov. 19, 2024

(54) METHODS AND COMPOSITIONS FOR INFLUENZA A VIRUS SUBTYPING

(71) Applicant: The United States of America, as represented by the Secretary, Dept. of Health and Human Services, Bethesda, MD (US)

(72) Inventors: Genyan Yang, Tucker, GA (US); Charles Todd Davis, Decatur, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 248 days.

(21) Appl. No.: 17/555,862

(22) Filed: Dec. 20, 2021

(65) Prior Publication Data
US 2022/0112567 A1 Apr. 14, 2022

Related U.S. Application Data

(62) Division of application No. 16/313,330, filed as application No. PCT/US2017/039018 on Jun. 23, 2017, now Pat. No. 11,248,272.

(60) Provisional application No. 62/355,267, filed on Jun. 27, 2016.

(51) Int. Cl.
C12Q 1/70 (2006.01)
C12Q 1/6806 (2018.01)
C12Q 1/6816 (2018.01)
C12Q 1/686 (2018.01)

(52) U.S. Cl.
CPC .......... *C12Q 1/701* (2013.01); *C12Q 1/6806* (2013.01); *C12Q 1/6816* (2013.01); *C12Q 1/686* (2013.01); *C12Q 1/70* (2013.01); *C12Q 2600/112* (2013.01); *C12Q 2600/156* (2013.01); *C12Q 2600/16* (2013.01); *C12Q 2600/166* (2013.01)

(58) Field of Classification Search
CPC .... C12Q 1/701; C12Q 1/6806; C12Q 1/6816; C12Q 1/686; C12Q 1/70; C12Q 2600/112; C12Q 2600/156; C12Q 2600/16; C12Q 2600/166
See application file for complete search history.

(56) References Cited

U.S. PATENT DOCUMENTS

| 8,232,058 B2 | 7/2012 | McBride et al. |
| 2003/0175706 A1 | 9/2003 | Zhang |
| 2005/0053957 A1 | 3/2005 | Rosenblum |
| 2013/0338022 A1 | 12/2013 | Kuersten et al. |
| 2014/0128279 A1 | 5/2014 | Lindstrom et al. |
| 2019/0247395 A9* | 8/2019 | Karp .................... C12N 5/0627 |

FOREIGN PATENT DOCUMENTS

| WO | WO 2004/083460 A1 | 9/2004 | |
| WO | WO 2005/092038 A2 | 10/2005 | |
| WO | WO-2007130519 A2 * | 11/2007 | ............... C12Q 1/70 |
| WO | WO 2012/021749 A1 | 2/2012 | |
| WO | WO-2013113965 A1 * | 8/2013 | ........... C12Q 1/6837 |
| WO | WO 2015/061475 A2 | 4/2015 | |

OTHER PUBLICATIONS

Machine Translation of WO-2013113965-A1. (Year: 2013).*
Sequence Listing for WO-2007130519-A2. (Year: 2007).*
Choi et al., "Accurate and effective multidrug-resistant *Mycobacterium tuberculosis* detection method using gap-filling ligation coupled with high-resolution capillary electrophoresis-based single strand conformation polymorphism," *Scientific Reports*, 7:46090, 2017 (9 pages).
Jacobs et al., "The thermal stability of oligonucleotide duplexes is sequence independent in tetraalkylammonium salt solutions: application to identifying recombinant DNA clones," *Nucl. Acids Res.*, vol. 16, pp. 4637-4650, 1988.
Parham et al., "Specific Magnetic Bead-Based Capture of Genomic DNA from Clinical Samples: Application to the Detection of Group B Streptococci in Vaginal/Anal Swabs," *Clin. Chem.*, vol. 53, pp. 1570-1576, 2007.
Ritari et al., "Detection of Human Papillomaviruses by Polymerase Chain Reaction and Ligation Reaction on Universal Microarray," *PLOS ONE*, vol. 7, e34211, pp. 1-8, 2012.
Stone et al., "Rapid detection and simultaneous subtype differentiation of influenza A viruses by real time PCR," *Journal of Virological Methods*, vol. 117, No. 2, pp. 103-112, 2004.
Sun et al., "A bead-based microfluidic approach to integrated single-cell gene expression analysis by quantitative RT-PCR," *RSC Advances*, vol. 5, pp. 4886-4893, 2015.
Wang et al., "Development of multiplex reverse transcription-ligase detection reaction-polymerase chain reaction (MRLP) mediated universal DNA microarray for diagnostic platform," *Biosensors and Bioelectronics*, vol. 26, pp. 3719-3724, 2011.

(Continued)

*Primary Examiner* — Angela M. Bertagna
*Assistant Examiner* — Francesca Filippa Giammona
(74) *Attorney, Agent, or Firm* — Klarquist Sparkman, LLP

(57) ABSTRACT

Disclosed herein are methods for detecting presence of a target nucleic acid (such as an influenza virus nucleic acid) in a sample. In some embodiments, the methods include contacting the sample with a first probe capable of hybridizing to the target nucleic acid and a second probe capable of hybridizing to the target nucleic acid, contacting the resulting complex with one or more gap filling reagents, thereby producing a gap-filled target nucleic acid, isolating and amplifying the gap-filled target nucleic acid. The amplified gap-filled target nucleic acid covalently linked to the substrate is then detected, for example with a detectably labeled probe. Also disclosed herein are probes capable of hybridizing to influenza virus nucleic acids. The disclosure also includes kits for detecting and/or discriminating influenza virus nucleic acids in a sample. In some examples, the kits include two or more of the disclosed probes.

8 Claims, 12 Drawing Sheets

Specification includes a Sequence Listing.

(56) References Cited

OTHER PUBLICATIONS

Wang et al., "Subtyping Clinical Specimens of Influenza A Virus by Use of a Simple Method to Amplify RNA Targets," *J. Clin. Microbiol.*, vol. 51, No. 10, pp. 3324-3330, 2013.

Wood et al., "Base composition-independent hybridization in tetramethylammonium chloride: A method for oligonucleotide screening of highly complex gene libraries," *PNAS*, vol. 82, pp. 1585-1588, 1985.

Yang et al., "Multiplex assay for subtyping avian influenza A viruses by cDNA hybridization and adapter-mediated amplification," *Applied Microbiology and Biotechnology*, vol. 100, No. 20, pp. 8809-8818, 2016.

Yang, "Multiplex Assay for Subtyping Zoonotic Influenza A Virus by cDNA Hybridization & Adapter-Mediated Amplification," *Influenza* 2015, Sep. 8-10, 2015 (presentation, 17 pages).

Yi et al., "A New Genotyping Method for Detecting Low Abundance Single Nucleotide Mutations Based on Gap Ligase Chain Reaction and Quantitative PCR Assay," *Cell Biochem. Biophys.*, vol. 62, pp. 161-167, 2012.

\* cited by examiner

1. Conjugation of hybridization probes (HPs) to beads
   Can be prepared as a stock (>1 yr shelf life)

2. Hybridization of probes to DNA (BPs, on-bead HPs) (30 min)

3. Gap filling with dNTPS (10 min)

4. Denaturation/Purification (10 min)

5. TaqMan qPCR (90 min)

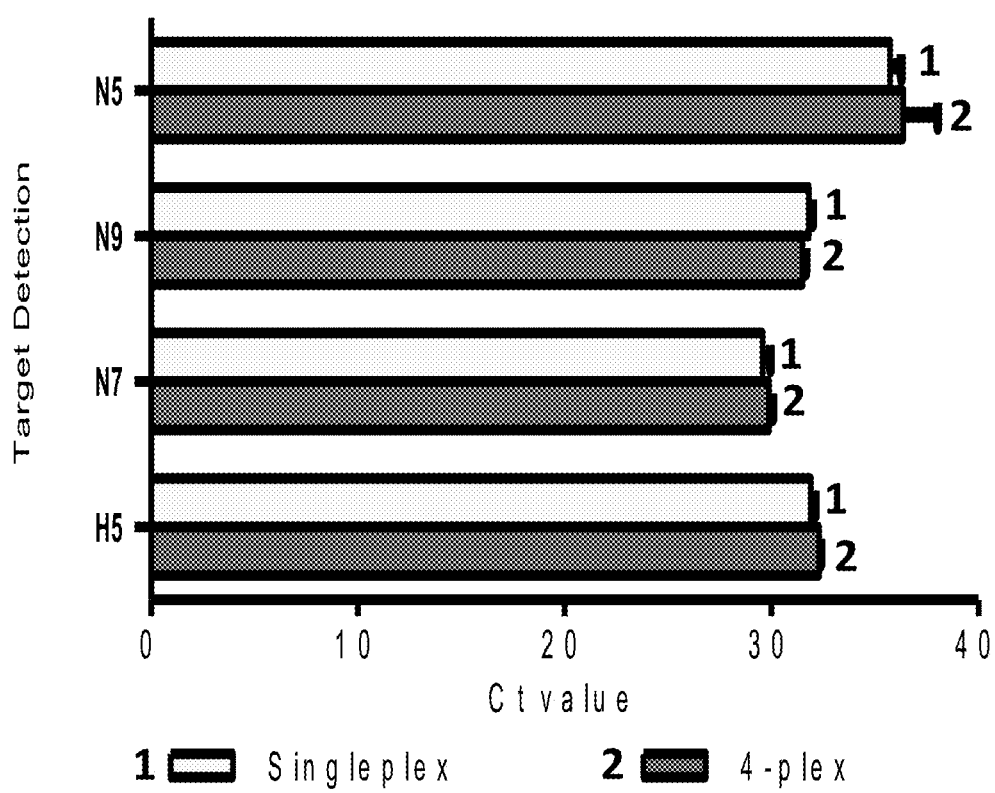

FIG. 5

| Dye | Em (nm) | Target* (number of probes: HP, BP, TMP) | | | | | |
|---|---|---|---|---|---|---|---|
| | | Set 1 | Set 2 | Set 3 | Set 4 | Set 5 | Set 6 |
| Atto425 | 484 | H8 (1,1,1) | H9 (2,2,3) | IBV (1,1,1)* | H11 (1,2,1) | β-Actin (1,1,1) | |
| FAM | 518 | N8 (1,1,1) | H5 (3,3,3) | N6 (2,2,2) | N1 (2,3,1) | H16 (1,2,3) | H13 (2,1,3) |
| HEX | 556 | N7 (1,2,3) | NDV (1,1,1) | N4 (1,1,1) | H14 (1,1,1) | H10 (1,1,3) | H15 (1,1,1) |
| TEX | 615 | H4 (1,2,2) | H7 (2,2,2) | H12 (1,1,1) | N3 (1,1,1) | N2 (1,2,2) | N9 (1,1,1) |
| Cy5 | 667 | H2 (1,1,1) | InfA (rRNA) (1,1,1)* | H3 (1,2,2) | H6 (2,2,1) | N5 (2,2,2) | H1 (3,3,2) |

Abbreviations: Em=emission wave length; HP=hybridization probe; DP=detection probe; TMP=TaqMan probe
* The matrix gene of influenza A was used for probe design

FIG. 6C

| Subtype | Strain name | Passage | copies/µL |
|---|---|---|---|
| H1N1 | A/duck/Bangladesh/1352/2009 | E1(05/26/2011) | (2.13±0.65)x10^6 |
| H2N4 | A/Nomadic Duck/Bangladesh/727/2011 | E2(02/28/2013) | (6.16±0.7)x10^5 |
| H3N8 | A/duck/Vietnam/NCVD-476/2010 | Ex/E1(1/20/2011) | (7.5±0.0.62)x10^5 |
| H4N2 | A/duck/Bangladesh/1746/2010 | E1(05/16/2011) | (9.92±0.49)x10^5 |
| H5N6 | A/duck/Vietnam/NCVD14-A338/2014 | E1(4/3/2015) | (2.18±0.4)x10^6 |
| H6N5 | A/wigeon/Italy/6127-23/2007 | Ex/E1(3/11/2010) | (5.06±0.63)x10^6 |
| H7N9 | A/Anhui/01/2013 | P3/E1/E1(7/3/2013) | (2.11±0.31)x10^6 |
| H8N4 | A/Garganey/Ukraine/05835-NAMRU3/2006 | E1(5/26/11) | (2.37±0.35)x10^5 |
| H9N2 | A/chicken/Bangladesh/21C-531/2015 | E1(9-16-15) | (4.37±1.33)x10^7 |
| H10N7 | A/duck/Vietnam/NCVD-0100/2012 | E1(6/26/2013) | (2.14±0.27)x10^6 |
| H11N3 | A/duck/Bangladesh/1595/2010 | E1(05/20/2011) | (1.33±0.08)x10^6 |
| H12N5 | A/MALLARD/ALBERTA/60/76 | E2/E1C1(05/26/2014) | (7.62±0.19)x10^5 |
| H13N9 | A/SHOREBIRD/DE/68/2004 | E2/E1C1(05/26/2014) | (2.97±0.63)x10^6 |
| H14N6 | A/Garganey/Ukraine/05839-NAMRU3/2006 | E1/E1(10/28/2009) | (1.91±0.24)x10^6 |
| H15N9 | A/SHEARWATER/WEST AUSTRALIA/2576/79 | EXE3/E1C1(05/26/2014) | (5.79±0.99)x10^5 |
| H16N3 | A/SHOREBIRD/DE/172/06 | E2/E1C1(05/26/2014) | (2.18±0.0.81)x10^5 |

FIG. 7A

| Subtype | Strain name | Target | Copies/hybridization | Copies/µL |
|---|---|---|---|---|
| H1N1 | A/duck/Bangladesh/1352/2009 | H1 | 9,075 | 363 |
| H2N4 | A/Nomadic Duck/Bangladesh/727/2011 | H2 | 34 | 1 |
| H3N8 | A/duck/Vietnam/NCVD-476/2010 | H3 | 303 | 12 |
| H4N2 | A/duck/Bangladesh/1746/2010 | H4 | 303 | 12 |
| H5N6 | A/duck/Vietnam/NCVD14-A338/2014 | H5 | 34 | 1 |
| H6N5 | A/wigeon/Italy/6127-23/2007 | H6 | 303 | 12 |
| H7N9 | A/Anhui/01/2013 | H7 | 101 | 4 |
| H8N4 | A/Garganey/Ukraine/05835-NAMRU3/2006 | H8 | 34 | 1 |
| H9N2 | A/chicken/Bangladesh/21C-531/2015 | H9 | 34 | 1 |
| H10N7 | A/duck/Vietnam/NCVD-0100/2012 | H10 | 9,075 | 363 |
| H11N3 | A/duck/Bangladesh/1595/2010 | H11 | 9,075 | 363 |
| H12N5 | A/MALLARD/ALBERTA/60/76 | H12 | 34 | 1 |
| H13N9 | A/SHOREBIRD/DE/68/2004 | H13 | 303 | 12 |
| H14N6 | A/Garganey/Ukraine/05839-NAMRU3/2006 | H14 | 9,075 | 363 |
| H15N9 | A/SHEARWATER/WEST AUSTRALIA/2576/79 | H15 | 9,075 | 363 |
| H16N3 | A/SHOREBIRD/DE/172/06 | H16 | 303 | 12 |

FIG. 7B

| Subtype | Strain name | Target | Copies/hybridization | Copies/µL |
|---|---|---|---|---|
| H1N1 | A/duck/Bangladesh/1352/2009 | N1 | 27,263 | 1,091 |
| H4N2 | A/duck/Bangladesh/1746/2010 | N2 | 34 | 1 |
| H9N2 | A/chicken/Bangladesh/21C-531/2015 | N2 | 9,075 | 363 |
| H11N3 | A/duck/Bangladesh/1595/2010 | N3 | 497* | 9* |
| H16N3 | A/SHOREBIRD/DE/172/06 | N3 | 217* | 4* |
| H2N4 | A/Nomadic Duck/Bangladesh/727/2011 | N4 | 9,075 | 363 |
| H8N4 | A/Garganey/Ukraine/05835-NAMRU3/2006 | N4 | 1,091 | 34 |
| H6N5 | A/wigeon/Italy/6127-23/2007 | N5 | 34 | 1 |
| H12N5 | A/MALLARD/ALBERTA/60/76 | N5 | 34 | 1 |
| H5N6 | A/duck/Vietnam/NCVD14-A338/2014 | N6 | 34 | 1 |
| H14N6 | A/Garganey/Ukraine/05839-NAMRU3/2006 | N6 | 303 | 12 |
| H10N7 | A/duck/Vietnam/NCVD-0100/2012 | N7 | 27,263 | 1,091 |
| H3N8 | A/duck/Vietnam/NCVD-476/2010 | N8 | 101 | 4 |
| H7N9 | A/Anhui/01/2013 | N9 | 791* | 14* |
| H13N9 | A/SHOREBIRD/DE/68/2004 | N9 | 1,115* | 20* |
| H15N9 | A/SHEARWATER/WEST AUSTRALIA/2576/79 | N9 | 217* | 4* |

METHODS AND COMPOSITIONS FOR INFLUENZA A VIRUS SUBTYPING

CROSS REFERENCE TO RELATED APPLICATIONS

This application is the divisional of co-pending U.S. application Ser. No. 16/313,330, filed Dec. 26, 2018, which is the § 371 U.S. National Stage of International Application No. PCT/US2017/039018, filed Jun. 23, 2017, which was published in English under PCT Article 21(2), which in turn claims the benefit of U.S. Provisional Application No. 62/355,267, filed Jun. 27, 2016, each of which is incorporated herein by reference in its entirety.

FIELD

This disclosure relates to methods for detecting one or more subtypes of influenza virus and compositions for use in the disclosed methods.

SEQUENCE LISTING INCORPORATION BY REFERENCE

The Sequence Listing is submitted as an ASCII text file in the form of the file named 4239-97168-04_Sequence_Listing_ST25.txt, which was created on May 4, 2024, and is 33,037 bytes, which is incorporated by reference herein.

BACKGROUND

Influenza A viruses circulating in animals, especially swine and poultry, represent potential sources of infection for humans. Given the appropriate conditions and potential for mutation, reassortment, and adaptation, zoonotic infections may generate a virus capable of further human-to-human transmission (Neumann and Kawaoka, *Virology*, 479-480:234-246, 2015). The human population has little to no pre-existing antibodies to many of the influenza subtypes circulating in various animal reservoirs. Thus, zoonosis can lead to severe morbidity and mortality and may initiate a pandemic. Historically, influenza pandemics have resulted from emergence of animal-origin influenza A viruses, including the most recent 2009 influenza A (H1N1) pandemic (Dowdle, *Emerg. Inf. Dis.* 12:34-39, 2006; Rambaut and Holmes, *PLoS Curr.* 1:RRN1003, 2009; Swerdlow et al., *Clin. Infect. Dis.* 52:S1-3, 2011). In recent years, human infections with avian influenza A(H5N1), A(H5N6), A(H6N1), A(H7N3), A(H7N7), A(H7N9), A(H9N2), A(H10N7), and A(H10N8) subtype viruses from poultry and A(H3) and A(H1) subtypes from swine have led to a surge in surveillance activities (Abdelwhab et al., *Epidemiol. Infect.* 142:896-920, 2014; Arzey et al., *Emerg. Inf Dis.* 18:814-816, 2012; Jernigan and Cox, *Ann. Rev. Med.* 66:361-371, 2015; Neumann and Kawaoka, *Virology*, 479-480:234-246, 2015).

The genome of influenza A virus contains eight segments of single-stranded, negative-sense RNA. Two segments encoding highly variable viral surface antigens, hemagglutinin (HA) and neuraminidase (NA), are used for determining subtypes of influenza A viruses. To date, 16 different HA subtypes (H1 to H16) and 9 NA subtypes (N1 to N9) have been identified in avian and mammalian species. Recently, H17N10 and H18N11 have been discovered in bats, but the origin and ecology of the viruses remain unclear (Tong et al., *Proc. Natl. Acad. Sci. USA* 109:4269-4274, 2012; Tong et al., *PLoS Pathog.* 9:e1003657, 2013).

SUMMARY

Conventional PCR, Sanger sequencing, real-time RT-PCR, and next generation sequencing are currently utilized as alternatives to classical serologic methods used to subtype influenza A viruses (Caliendo *Clin. Infect. Dis.* 52:S326-330, 2011; Spackman, *Meth. Mol. Biol.* 1161:119-123, 2014). While these technologies are powerful, they require constant monitoring of viral genomes to ensure primer and/or probe complementarity to keep pace with the highly variable influenza virus genome. Error prone replication, rapid evolution, reassortment, and emergence of previously uncharacterized viruses can, therefore, increase effort and cost of genetically characterizing viruses. Thus, there remains a need for rapid, sensitive, and specific influenza virus detection and subtyping. In some non-limiting embodiments, the methods described herein are used to subtype and/or characterize diverse influenza A viruses using cDNA hybridization and adapter-mediated amplification for subtyping influenza virus (referred to herein as AmASIV).

Disclosed herein are methods for detecting presence of a target nucleic acid (such as an influenza virus nucleic acid) in a sample. In some embodiments, the methods include contacting the sample with a first probe capable of hybridizing to the target nucleic acid and a second probe capable of hybridizing to the target nucleic acid under conditions sufficient for the first probe and the second probe to hybridize to the target nucleic acid to produce a complex comprising the first probe, the second probe, and the target nucleic acid, wherein the first probe and the second probe hybridize to the target nucleic acid with a gap of 5-200 nucleotides between the first probe and the second probe and wherein one of the first probe and the second probe is covalently linked to a substrate. The complex comprising the first probe, the second probe, and the target nucleic acid is contacted with one or more gap filling reagents under conditions sufficient to fill the gap between the first probe and the second probe, thereby producing a gap-filled target nucleic acid. The resulting double-stranded gap-filled target nucleic acid is denatured and the gap-filled target nucleic acid covalently linked to the substrate is isolated and amplified. The amplified gap-filled target nucleic acid covalently linked to the substrate is then detected, for example with a detectably labeled probe (such as using real-time PCR).

In some examples, each of the first probe and the second probe include a first region capable of hybridizing to the target nucleic acid and a second portion not capable of hybridizing to the target nucleic acid. The second portion of each probe is also referred to herein as an "adapter" probe or AP. The amplification of the isolated gap-filled target nucleic acid can be performed using primers (such as universal amplification primers, or UAP) that are complementary to the AP. As a result, a single set of amplification primers can be utilized for amplification of multiple different gap-filled target nucleic acids, providing that the probes for each target nucleic acid include the same "universal" adapter sequences.

In some embodiments, the disclosed methods include detecting an influenza virus nucleic acid in a sample, wherein the method includes contacting the sample with at least two probes comprising a first probe capable of hybridizing to a target influenza virus nucleic acid and a second probe capable of hybridizing to the target influenza virus nucleic acid under conditions sufficient for the first probe and the second probe to hybridize to the target influenza virus nucleic acid to produce a complex comprising the first probe, the second probe, and the target influenza virus nucleic acid, wherein the first probe and the second probe hybridize to the target influenza virus nucleic acid with a gap of 5-200 nucleotides between the first probe and the second probe and wherein one of the first probe and the second probe is covalently linked to a substrate, and wherein each of the first probe and the second probe each comprise a first portion capable of hybridizing to the target influenza virus nucleic acid and a second portion not capable of hybridizing to the target influenza virus nucleic acid. The complex comprising the first probe, the second probe, and the target influenza virus nucleic acid is contacted with one or more gap filling reagents under conditions sufficient to fill the gap between the first probe and the second probe, thereby producing gap-filled double-stranded target nucleic acid. The gap-filled double stranded target nucleic acid is denatured and the gap-filled target nucleic acid covalently linked to the substrate is isolated and the isolated gap-filled target nucleic acid covalently linked to the substrate is amplified by contacting the isolated gap-filled target nucleic acid covalently linked to the substrate with a pair of oligonucleotide primers complementary to at least a portion of the second portion of each of the first probe and the second probe. The amplified gap-filled target nucleic acid covalently linked to the substrate is measured by contacting the amplified gap-filled target nucleic acid covalently linked to the substrate with at least one detection probe capable of hybridizing to the target influenza virus nucleic acid, thereby detecting presence of the influenza virus in the sample.

In some examples of the disclosed methods, the first portion of the first probe selected from the sequence of any one of SEQ ID NOs: 1, 2, 7, 12, 15, 18-21. 28, 29, 34, 44, 47, 48, 52-54, 60, 64, 69, 74-79, 90, 91, 95, 96, 101, 104, 105, 111, 116, 120, 123, 124, 129, 132, 135, 141, 144, 147, 149, and 152 and the second portion of the first probe is SEQ ID NO: 155 and the first portion of the second probe is selected from any one of SEQ ID NOs: 3-5, 8, 9, 13, 16, 22-25, 30, 31, 35-39, 45, 49, 50, 55-57, 61, 65, 66, 70, 71, 80-85, 159, 92, 93, 97, 98, 102, 106, 107, 112, 117, 118, 121, 125, 130, 133, 136, 137, 142, 145, 148, 150, and 153 and the second portion of the second probe is SEQ ID NO: 156. In some examples of the methods, the detection probe includes the nucleic acid sequence of at least one of SEQ ID NOs: 6, 10, 11, 14, 17, 26, 27, 32, 33, 40-43, 46, 51, 58, 59, 62, 63, 67, 68, 72, 73, 86-89, 160, 94, 99, 100, 103, 108-110, 113-115, 119, 122, 126-128, 131, 134, 138-140, 143, 146, 151, and 154 and a detectable label.

Also disclosed herein are probes capable of hybridizing to influenza virus nucleic acids, such as subtype-specific probes, for example, probes including the sequence of any one of SEQ ID NOs: 1-148. Also disclosed are probes capable of hybridizing to Newcastle disease virus (NDV) nucleic acids, for example probes including the sequence of any one of SEQ ID NOs: 149-151, and probes capable of hybridizing to beta-actin nucleic acids (such as avian beta-actin), for example probes including the sequence of any one of SEQ ID NOs: 152-154. In some examples, the probes also include an adapter sequence, such as the sequence of SEQ ID NO: 155 or 156.

In particular examples, the probes are hybridization or bridge probes including the sequence of any one of SEQ ID NOs: 1, 2, 7, 12, 15, 18-21. 28, 29, 34, 44, 47, 48, 52-54, 60, 64, 69, 74-79, 90, 91, 95, 96, 101, 104, 105, 111, 116, 120, 123, 124, 129, 132, 135, 141, 144, 147, 149, and 152 plus adapter sequence SEQ ID NO: 155 or the sequence of any one of SEQ ID NOs: 3-5, 8, 9, 13, 16, 22-25, 30, 31, 35-39, 45, 49, 50, 55-57, 61, 65, 66, 70, 71, 80-85, 159, 92, 93, 97, 98, 102, 106, 107, 112, 117, 118, 121, 125, 130, 133, 136, 137, 142, 145, 148, 150, and 153 plus adapter sequence SEQ ID NO: 156. Some of the disclosed probes are detection probes that include at least one detectable label. In particular examples, the probes include the sequence of any one of SEQ ID NOs: 6, 10, 11, 14, 17, 26, 27, 32, 33, 40-43, 46, 51, 58, 59, 62, 63, 67, 68, 72, 73, 86-89, 160, 94, 99, 100, 103, 108-110, 113-115, 119, 122, 126-128, 131, 134, 138-140, 143, 146, 151, and 154 and at least one detectable label. In some examples the at least one detectable label includes a fluorophore and at least one fluorescence quencher.

This disclosure also includes kits for detecting and/or discriminating influenza virus nucleic acids (such as influenza virus subtypes) in a sample. In some examples, the kits include two or more of the disclosed probes, such as at least one hybridization probe selected from the sequence of any one of SEQ ID NOs: 1, 2, 7, 12, 15, 18-21. 28, 29, 34, 44, 47, 48, 52-54, 60, 64, 69, 74-79, 90, 91, 95, 96, 101, 104, 105, 111, 116, 120, 123, 124, 129, 132, 135, 141, 144, 147, 149, and 152 plus adapter sequence SEQ ID NO: 155 and at least one bridge probe selected from any one of SEQ ID NOs: 3-5, 8, 9, 13, 16, 22-25, 30, 31, 35-39, 45, 49, 50, 55-57, 61, 65, 66, 70, 71, 80-85, 159, 92, 93, 97, 98, 102, 106, 107, 112, 117, 118, 121, 125, 130, 133, 136, 137, 142, 145, 148, 150, and 153 plus adapter sequence SEQ ID NO: 156. The kits also include at least one detectably labeled probe, such as at least one of SEQ ID NOs: 6, 10, 11, 14, 17, 26, 27, 32, 33, 40-43, 46, 51, 58, 59, 62, 63, 67, 68, 72, 73, 86-89, 160, 94, 99, 100, 103, 108-110, 113-115, 119, 122, 126-128, 131, 134, 138-140, 143, 146, 151, and 154 and a detectable label. In some embodiments, the kits further include a pair of universal amplification primers including the sequence of SEQ ID NO: 157 and SEQ ID NO: 158.

The foregoing and other features of the disclosure will become more apparent from the following detailed description, which proceeds with reference to the accompanying figures.

BRIEF DESCRIPTION OF THE DRAWINGS

FIG. 2A shows the amount of free probe left in the supernatant before and after conjugation of probes to magnetic beads for 2 or 16 hours. Coupling efficiency that measures the percentage of probes conjugated to the beads was estimated by comparing A260 readings pre- and post-coupling reactions. The error bars were calculated from duplicate readings. FIG. 2B shows target-probe hybridization efficiency after 2 or 16 hours of conjugation to magnetic beads. Hybridization efficiency was assessed using relative strength of fluorescence of the experimental group over the pre-coupling background control. FIG. 2C shows the effect of the ratio of HP to magnetic beads for conjugation efficiency. The specified amount of HPs were incubated with magnetic beads for 1 hour and the relative quantity of probe coupled to the beads was estimated using an adapter-complementary probe quality control method. Error bars were calculated from duplicate readings for each data point. Beads without probe conjugation were used as a background (NPC, no probe control).

FIG. 3A shows Ct values for H5N1 cDNA (A/poultry/Bangladesh/91392/2013) hybridized to bead conjugated HP for 30 minutes at the indicated temperatures. The relative quantity of cDNA hybridized to the on-bead probes was measured using an influenza A TaqMan qPCR. The P values were calculated using two-tailed t-test from the Ct value of multiple runs (n≥3) for each temperature. FIG. 3B shows Ct values for H5N1 (target) or influenza B virus (near neighbor non-target control) hybridized to bead-conjugated HP at 42° C. for the indicated times. The relative quantity of cDNA before (input control) and after hybridization (target detection) was determined using the corresponding TaqMan qPCR assay. PCR was performed in duplicate for each time point. IFA, influenza A; IFB, influenza B, NTC, no template control.

FIGS. 4A and 4B show performance of exemplary singleplex and four-plex assays. FIG. 4A shows TMPs synthesized with distinct fluorophores to detect and differentiate different HA and NA subtypes of influenza A viruses. Upper panel, image of TMPs prepared in 100× working concentration. Probes for H5, N7, N9, and N5 were labeled with FAM, HEX, TEX, and Cy5, respectively. Lower panel, the four fluorophores have distinct peak of emission wavelengths (FAM=518 nm, HEX=556 nm, TEX=615 nm, and Cy5=667 nm). FIG. 4B is a graph showing comparison between singleplex and 4-plex AmASIV assay. Ct value and the standard deviation were calculated from triplicate runs. The N5-, N9-, N7-, and H5-representing viruses were H6N5 (A/wigeon/Italy/6127-23/2007), H7N9 (A/Anhui/01/2013), H10N7 (A/duck/Vietnam/NCVD-0100/2012), and H5N1 (A/poultry/Bangladesh/91392/2013).

FIG. 5 shows exemplary sets of multiplex assays (Sets 1-6) for subtyping influenza A viruses (FIG. 5). Shaded targets are controls that can be included in the sets.

FIGS. 6A-6C are a series of panels showing RNA quantification of the indicated influenza A subtypes. FIGS. 6A and 6B are graphs showing quantification of the RNA of influenza A virus using standard curve analysis. RNA transcripts of the influenza A matrix gene were generated using in vitro RNA transcription. Six 10-fold serial dilutions of the transcripts were used as templates for TaqMan real-time RT-PCR (FIG. 6A). Standard curves were generated using copies of the transcripts against the Ct values from triplicate reactions per dilution of the transcripts (FIG. 6B). Influenza A virus isolates covering all HA (H1-H16) and NA (N1-N9) subtypes were quantified using standard curve analysis (FIGS. 6B and 6C). indicating the specific amount of RNA template that was tested in the assay.

FIGS. 7A and 7B show limit of detection of the AmASIV assay for influenza A subtypes H1-H16 (FIG. 7A) and N1-N9 (FIG. 7B).

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1-148 are exemplary influenza virus probes for use in the AmASIV assays described herein.

SEQ ID NOs: 149-151 are exemplary Newcastle disease virus probes

SEQ ID NOs: 152-154 are exemplary avian β-actin probes

SEQ ID NOs: 155 and 156 are exemplary adapter oligonucleotides.

SEQ ID NOs: 157 and 158 are exemplary universal adapter primers (UAP).

DETAILED DESCRIPTION

Rapid detection and characterization of animal influenza virus, especially those viruses with zoonotic or pandemic potential, is critical for identifying sources of infection and assessing risk. The serological and conventional molecular assays currently on hand have disadvantages due to continued evolution and emergence of novel or unusual subtypes. The methods disclosed herein are a rapid test for identification, subtyping, and semi-quantification of influenza A viruses. The adapter-mediated sequence independent amplification method developed by the inventors makes the assay less vulnerable to genomic mutations common to influenza A viruses. In addition, target enrichment through random-primer based cDNA hybridization can accommodate low quality samples with partial RNA degradation or high levels of non-target contamination that are often associated with animal and environmental samples.

Figure 1:
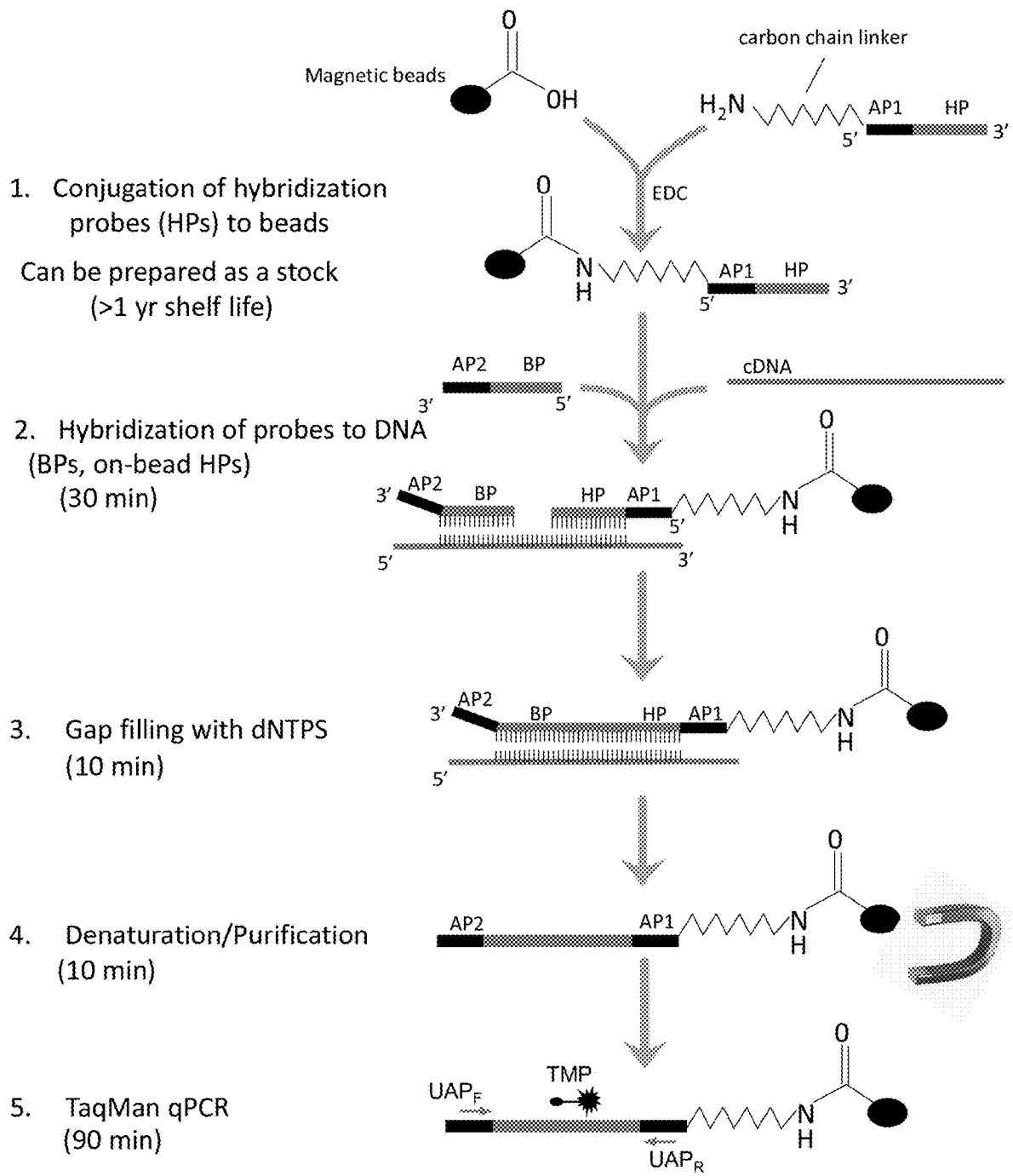
FIG. 1 is a schematic diagram of an exemplary adapter-mediated amplification for subtyping influenza virus (AmA-SIV) assay. A chimeric oligonucleotide is synthesized with an adaptor (AP1) and an influenza subtype-specific hybridization probe (HP). A second chimeric oligonucleotide with a second adapter (AP2) and a subtype-specific bridge probe (BP) is also synthesized. The chimeric AP1-HP oligonucleotide is covalently conjugated to magnetic beads using an amine group on the HP portion of the probe. Influenza cDNA converted from total RNA using random primers is hybridized to the bead-coupled HPs simultaneously with BPs of the same target to form a complex consisting of BP, HP and target cDNA. Following hybridization, the gap between the BP and HP is filled with dNTPs using a DNA polymerase and ligase. A brief denaturation at room temperature in 0.2N sodium hydroxide is followed by magnetic bead purification steps to remove excess free probes, impurities, and the input cDNA. The single-strand DNA immobilized on the bead is then used as a template for PCR amplification in an influenza sequence-independent manner using universal adapter primers (UAP). Identification of influenza subtype is done through subtype-specific PCR probes (e.g., TaqMan probes (TMP)).

Given that 25-30% sequence variation exists within many of the same HA and NA subtypes, it is difficult to design a single set of primers/probes to detect all variants within a given subtype. This is especially problematic when working with samples from diverse animal species from multiple continents where limited sequence data are available or distinct clusters of genetic variants are present. Choosing multiple sets of primers/probes has the potential to improve mutation coverage, but it also introduces the likelihood of primer-primer interactions or biased amplification when using conventional single- or multiplex RT-PCR strategies (Gunson et al., *J. Clin. Virol*. 35:355-367, 2006). To overcome these hurdles, the inventors developed an approach to separate target enrichment from target amplification in different steps (FIG. 1). In addition, using a modified hybridization buffer including tetramethylammonium chloride (TMAC) makes it possible to apply multiple HPs and BPs in a single hybridization reaction. TMAC selectively raises the stability of A-T base pairs to that of G-C base pairs of a probe (Wood et al., *Proc. Natl. Acad. Sci. USA* 82:1585-1588, 1985). Therefore, hybridization annealing temperature becomes irrelevant to the GC content, but is proportional to the length of a probe. This feature is especially useful for multiplex hybridization as it allows use of a uniform hybridization temperature for a variety of probes of the same length but with different sequences.

High specificity is crucial for animal influenza virus surveillance, especially for those viruses that produce high morbidity and mortality in infected poultry flocks or livestock, as false positive reports could incur devastating economic consequences as could failure to detect virus. For example, in many countries, if one bird is determined to be positive for highly pathogenic avian influenza virus, the entire flock and all poultry in a zone of specified radius around infected premises will be depopulated within hours of detection. To further improve the specificity of the assay disclosed herein, probes (HP, BP and TMP) were designed without significant overlap to eliminate potential amplification in the absence of a target. All probes were selected in regions that were subtype-specific, but away from 5' and 3'UTRs of the HA and NA genes due to high sequence conservation among influenza A virus segments in this region.

Thus, the inventors have developed a unique strategy for target enrichment, amplification, subtyping, and real-time quantification of influenza A viruses. This assay can more easily and rapidly subtype viruses in complex sample types than currently utilized assays, without the need to culture virus. As such, the method can be utilized as a screening tool to make decisions regarding downstream testing of samples and prioritize surveillance activities. In addition, the disclosed assay can be used as a surveillance tool to help us understand the prevalence and distribution dynamics of avian and swine influenza viruses at the animal-human interface, identify unusual subtypes of influenza A viruses infecting humans, and better target control measures.

I. Abbreviations

AmASIV adapter-mediated amplification for subtyping influenza virus
AP adapter oligonucleotide
BP bridge probe
EDC 1-ethyl-3-[3-dimethylaminopropyl] carbodiimide hydrochloride
$EID_{50}$ 50% egg infectious dose
HA (or H) hemagglutinin gene or protein
HP hybridization probe
InfA influenza A
LOD limit of detection
M matrix gene or protein
NA (or N) neuraminidase gene or protein
NDV Newcastle disease virus
qPCR quantitative real-time PCR
TMAC tetramethylammonium chloride
TMP TaqMan probe
UAP universal adapter primer

II. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, $3^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. Sequences associated with database Accession Numbers are herein incorporated by reference as present in the specified database on Jun. 27, 2016, unless otherwise noted. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include real-time PCR; quantitative real-time PCR; reverse transcriptase PCR (RT-PCR); real-time reverse transcriptase PCR (rRT-PCR); nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see Eur. Pat. Publ. EP320308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others.

Conditions sufficient for: Any environment that permits the desired activity, for example, that permits specific binding or hybridization between two nucleic acid molecules (such as an HP or BP and target nucleic acid) or that permits amplification of a target nucleic acid, or gap-filling of probes hybridized to a target nucleic acid.

Contact: Placement in direct physical association; includes both in solid and liquid form. For example, contacting can occur in vitro with a nucleic acid probe and a sample in solution.

Fluorophore: A chemical compound, which when excited by exposure to a particular stimulus such as a defined wavelength of light, emits light (fluoresces), for example at a different wavelength (such as a longer wavelength of light). Examples of particular fluorophores that can be used in the probes are disclosed herein.

"Acceptor fluorophores" (quenchers) are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

"Donor Fluorophores" are fluorophores or luminescent molecules capable of transferring energy to an acceptor fluorophore, thereby generating a detectable fluorescent signal when separated from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as an influenza virus nucleic acid. For example, a probe or primer having homology to an influenza virus nucleic acid molecule will form a hybridization complex with a complementary nucleic acid molecule. If a primer is used, the influenza virus nucleic acid can be amplified, for example using PCR.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, NY (chapters 9 and 11). The probes and primers disclosed herein can hybridize to nucleic acid molecules under low stringency, high stringency, or very high stringency conditions.

Hydrolysis probe: A dual-labeled oligonucleotide probe for use in real-time PCR. Hydrolysis probes (also referred to as TaqMan probes or TMP) are detectably labeled at both the 5' and 3' ends. Typically, a hydrolysis probe includes a fluorophore at the 5' end and a quencher at the 3' end. The oligonucleotide is complementary to a target nucleic acid and the length of the oligonucleotide is such that the quencher is close enough to the fluorophore to suppress fluorescence. During the extension phase of real-time PCR, the 5'-3' nuclease of Taq polymerase degrades the hydrolysis probe, separating the fluorophore and quencher and allowing detectable fluorescence from the fluorophore.

Influenza Virus: Influenza viruses are enveloped negative-strand RNA viruses belonging to the orthomyxoviridae family. Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza consists of eight linear RNA molecules that encode up to thirteen polypeptides. Two of the polypeptides, HA and NA, include the primary antigenic determinants or epitopes required for a protective immune response against influenza.

Influenza viruses are classified on the basis of their core proteins into three distinct types: A, B, and C. Within these broad classifications, subtypes are further divided based on the characterization of two antigenic surface proteins hemagglutinin (HA or H) and neuraminidase (NA or N). Based on the antigenic characteristics of the HA and NA proteins, influenza strains are classified into subtypes. While B and C type influenza viruses are largely restricted to humans, influenza A viruses are pathogens of a wide variety of species including humans, non-human mammals, and birds. Periodically, non-human strains, particularly of swine and avian influenza, have infected human populations, in some cases causing severe disease with high mortality. Reassortment between such swine or avian strains and human strains in co-infected individuals has given rise to influenza viruses to which immunity is lacking in the human population, resulting in influenza pandemics.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Nucleotide and amino acid sequences of HA isolated from recent, as well as historic, influenza strains can be found, for example in the GenBank database (available on the World Wide Web at ncbi.nlm.nih.gov/entrez), Global Initiative on Sharing All Influenza Data (GISAID) database (available on the World Wide Web at platform.gisaid.org/), or the Influenza Research Database (available on the World Wide Web at fludb.org).

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N2, N3, N6, and N9 subtypes. Nucleotide and amino acid sequences of NA isolated from recent, as well as historic, influenza strains can be found, for example in the GenBank database (available on the World Wide Web at ncbi.nlm.nih.gov/entrez), the Global Initiative on Sharing All Influenza Data (GISAID) database (available on the World Wide Web at platform.gisaid.org/), or the Influenza Research Database (available on the World Wide Web at fludb.org).

The remaining segments of the influenza genome encode the internal proteins. PB2 is a 759 amino acid polypeptide which is one of the three proteins which comprise the RNA-dependent RNA polymerase complex. PB2 is encoded by approximately 2340 nucleotides of the influenza genome segment 1. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively. Segment 2 also encodes two other proteins: PB1-F2, a pro-apoptotic protein, and PB1-N40, a recently identified functionally unknown variant of the PB1 protein. Segment 3 also encodes another protein, PA-X, which modulates virulence. Segment 5 consists of about 1565 nucleotides encoding an about 498 amino acid nucleoprotein (NP) protein that forms the nucleocapsid. Segment 7 consists of an about 1027 nucleotide sequence of the M gene, which encodes the two matrix (M) proteins; an about 252 amino acid M1 protein, and an about 96 amino acid M2 protein, which is translated from a spliced variant of the M RNA. Segment 8 consists of the NS gene, which encodes two different non-structural proteins, NS1 and NS2.

Isolated: An "isolated" or "enriched" biological component (such as a nucleic acid) has been substantially separated or purified away from other biological components in a sample, such as other chromosomal and extrachromosomal DNA, RNA, and proteins. Nucleic acids that have been "isolated" include nucleic acids purified by standard purification methods or prepared by recombinant expression in a host cell as well as chemically synthesized nucleic acids, such as probes and primers. The term "isolated" or "enriched" also encompasses nucleic acids that are purified from a sample (such as a sample from a subject or an environmental sample) using the magnetic bead-conjugated probes described herein. Isolated or enriched does not require absolute purity, and can include nucleic acid molecules that are at least 50% isolated, such as at least 75%, 80%, 90%, 95%, 98%, 99% or even 100% isolated.

Label or Detectable Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

Limit of detection (LOD): The lowest analyte concentration that can be reliably (for example, reproducibly) detected for a given type of sample and/or assay method. In some examples, LOD is determined by testing serial dilutions of a sample known to contain the analyte and determining the lowest dilution at which detection occurs. In some examples, the LOD for an influenza virus assay (such as those described herein) is expressed as level of infectivity (for example, 50% tissue culture infective dose/ml ($TCID_{50}$/ml) or 50% embryo (or egg) infective dose/ml ($EID_{50}$/ml), expressed as a $log_{10}$ scale) or RNA copy number/µl that can be detected. One of skill in the art can determine the LOD for a particular assay and/or sample type using conventional methods.

Primers: Short nucleic acid molecules, such as a DNA oligonucleotide, for example nucleic acid molecules of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of an influenza nucleic acid), wherein the sequence of the primer is specific for the target nucleic acid molecule, for example so that the primer will hybridize to the target nucleic acid molecule under high or very high stringency hybridization conditions.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of an influenza nucleic acid) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, 20-40 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer3 (World Wide Web at flypush.imgen.bcm.tmc.edu/primer/primer3_www.cgi).

Probe: A probe comprises an isolated nucleic acid capable of hybridizing to a target nucleic acid (such as an influenza nucleic acid). In some non-limiting examples, a detectable label or reporter molecule is attached to a probe. However, in other examples, the probes described herein do not include a detectable label.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 20-40 nucleotides, 30-50 nucleotides, or 40-60 nucleotides.

Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987). In some examples, a probe (such as the TMPs described herein) includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe. In other examples, the probe includes a second quencher (such as a ZEN or TAO quencher, Integrated DNA Technologies) that is internal to the probe in addition to the 5' or 3' quencher. Such probes are referred to as "double-quenched" probes.

Quencher: A molecule that reduces fluorescence signal of a fluorophore molecule when the quencher is within proximity of the fluorophore. In some examples, a quencher is included at one end of a hydrolysis probe and a fluorophore is included at the other end of the same hydrolysis probe. Non-limiting examples of quenchers include Dabcyl, QSY7 (Molecular Probes), QSY33 (Molecular Probes), BLACK HOLE QUENCHERS™ (e.g., BHQ1, BHQ2, or BHQ3; Glen Research), ECLIPSE™ Dark Quencher (Epoch Biosciences), or IOWA BLACK™ (Integrated DNA Technologies).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as an influenza nucleic acid) and/or quantitate the initial amounts of a target nucleic acid sequence. In some examples, real time PCR is real time reverse transcriptase PCR (rRT-PCR).

In some examples, the amount of amplified target nucleic acid (such as an influenza virus nucleic acid) is detected using a labeled probe, such as a probe labeled with a fluorophore, for example a hydrolysis probe (such as a TMP). In this example, the increase in fluorescence emission is measured in real time, during the course of the RT-PCR. This increase in fluorescence emission is directly related to the increase in target nucleic acid amplification (such as influenza nucleic acid amplification). In some examples, the change in fluorescence (dRn) is calculated using the equation $dRn=Rn^+ - Rn^-$, with $Rn^+$ being the fluorescence emission of the product at each time point and Rn being the fluorescence emission of the baseline. The dRn values are plotted against cycle number, resulting in amplification plots. The threshold value (Ct) is the PCR cycle number at which the fluorescence emission (dRn) exceeds a chosen threshold, which is typically 10 times the standard deviation of the baseline (this threshold level can, however, be changed if desired).

Sample: Refers to any biological or environmental sample that includes or may include nucleic acids. In some embodiments, the sample is a biological sample obtained from a subject, such as a mucous, saliva, blood, urine, or fecal sample. In other embodiments, the sample is an environmental sample, such as a surface swab or a water sample.

Sensitivity and specificity: Statistical measurements of the performance of a binary classification test. Sensitivity measures the proportion of actual positives which are correctly identified (e.g., the percentage of samples that are identified as including nucleic acid from a particular organism). Specificity measures the proportion of negatives which are correctly identified (e.g., the percentage of samples that are identified as not including nucleic acid from a particular organism).

Subject: Living multi-cellular vertebrate organisms, a category that includes both human and non-human mammals (such as dogs, swine, and bats) and birds (such as poultry and water fowl). In some embodiments herein, the subject is a human. In other embodiments, the subject is a pig or bird.

Substrate: A solid support or surface. The configuration of the solid support can be flat (e.g., a plate or slide), spherical (e.g., a bead), or another configuration. Suitable substrate materials include, but are not limited to organic polymers such as polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof. In general, the material used for the substrate is amenable to surface activation such that upon activation, the surface of the substrate is capable of covalently attaching a biomolecule, such as a probe.

Target nucleic acid molecule: A nucleic acid molecule whose identification, detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule, which can include RNA (such as viral RNA) or DNA (such as DNA produced by reverse transcription of viral RNA). Purification or isolation of the target nucleic acid molecule, if needed, can be conducted by methods known to those in the art, such as by using a commercially available purification kit or the like. In one example, a target nucleic molecule is an influenza virus nucleic acid molecule (such as an influenza virus HA or NA nucleic acid molecule).

Type- or subtype-specific: An agent, such as a probe or primer that binds substantially or preferentially only to a defined target, such as a nucleic acid from a particular influenza virus type (such as influenza A, B, or C) or subtype (such as an influenza virus with a particular HA or NA nucleic acid).

III. Methods of Detecting Target Nucleic Acids

Disclosed herein are methods for detecting, measuring, and/or identifying presence of one or more nucleic acids in a sample, such as a biological or environmental sample. In some embodiments, the methods include enrichment of a target nucleic acid, followed by PCR amplification using universal primers to detect, measure, and/or identify target nucleic acids in the sample. In some examples, the PCR amplification also includes a detectably labeled probe for the target nucleic acid (such as by real-time PCR).

In embodiments described herein the methods are primarily utilized to detect and/or identify influenza virus nucleic acids; however, one of ordinary skill in the art will recognize that the methods can be adapted for any target nucleic acid of interest. In non-limiting examples, the target nucleic acid can include viral nucleic acids (for example, influenza virus, hepatitis virus (such as hepatitis A, hepatitis B, or hepatitis C), human immunodeficiency virus, respiratory syncytial virus, polyoma virus, cytomegalovirus, human papilloma virus, flavivirus (for example, Dengue virus, West Nile virus, St. Louis encephalitis virus, Japanese encephalitis virus, tick-borne encephalitis virus), togavirus (for example, rubella, Western equine encephalitis, Eastern equine encephalitis, Venezuelan equine encephalitis virus), filovirus (for example, Ebola virus, Marburg virus), enterovirus, poliovirus, or smallpox virus nucleic acids), bacterial nucleic acids (for example, *E. coli, Streptococcus pneumoniae, Neisseria meningitidis, Legionella* spp., *Mycoplasma pneumoniae, Mycobacterium tuberculosis, Staphylococcus aureus, Haemophilus influenzae, Bacillus anthracis, Brucella,* or *Yersinia pestis* nucleic acids), fungal nucleic acids (for example, *Candida, Aspergillus, Blastomyces, Coccidioides, Cryptococcus, Histoplasma, Pneumocystis, Sporothrix,* or *Exserohilum*) or parasite nucleic acids (such as *Plasmodium, Trypanosoma, Toxoplasma, Leishmania, Cryptosporidium, Giardia,* or *Trichinella* nucleic acids).

In some embodiments, the methods include contacting a sample containing (or suspected to contain) a target nucleic acid with two probes, each of which include a target-specific portion (e.g., a first portion) and an adapter portion (e.g., a second portion). The first probe is also covalently attached to a substrate, such as a capturable bead (for example, a magnetic bead or a biotinylated bead). The first probe (referred to herein as a hybridization probe or HP) and the second probe (referred to herein as a bridge probe or BP) each hybridize to a similar region of the target nucleic acid (typically within about 200 nucleotides of each other). Following hybridization of the substrate conjugated-HP and the BP to the target nucleic acid, the gap between the hybridized HP and BP is filled by contacting the sample with dNTPs, DNA polymerase (such as T4 DNA polymerase), and DNA ligase (such as T4 DNA ligase). The resulting double-stranded nucleic acid is briefly denatured and target nucleic acid is enriched or purified using the substrate, for example, by magnetic collection if the substrate is a magnetic bead. The enriched target nucleic acid is then amplified utilizing forward and reverse universal adapter primers (UAP) complementary to the adapters on the HP and BP and detected. In some examples, the amplification includes real-time PCR (e.g., qPCR) and the sample is contacted with a detectably labeled hydrolysis probe (such as a TaqMan probe (also referred to herein as a TMP) or other fluorescently-labeled probes, such as molecular beacon probes) and the UAPs. An example of an embodiment of the method is schematically illustrated in FIG. 1.

Appropriate samples include any conventional biological or environmental sample, including clinical samples obtained from a human or animal subject. Suitable samples include all biological samples useful for detection of viral infection in subjects, including, but not limited to, cells, tissues (for example, lung, liver, and kidney), autopsy samples, bodily fluids (for example, blood, serum, urine, cerebrospinal fluid, middle ear fluids, bronchoalveolar lavage, tracheal aspirates, sputum, nasopharyngeal swabs or aspirates, oropharyngeal swabs or aspirates, or saliva), eye swabs, cervical swabs, vaginal swabs, rectal swabs, cloacal swabs, stool, and fecal samples. In other examples, a biological includes purified nucleic acids, such as RNA, cDNA, or DNA. In some examples, the subject is a human subject. In other examples, the subject is an animal subject, such as an animal known or suspected to be a reservoir for influenza virus. In some examples, animal reservoirs for influenza virus include wild or domestic animals, such as pigs, poultry (for example, chickens or turkeys), waterfowl (for example, ducks or geese), other birds (such as gulls, terns, or shorebirds), bats, dogs, horses, ferrets, and marine mammals (for example, whales and seals). Additional suitable samples include environmental samples, such as samples from water, soil, biofilms, or surfaces (e.g., swabs from floors, walls, feeding areas, or waste disposal areas) for example samples from livestock areas, such as areas where chickens, ducks, turkeys, or swine are housed, slaughtered, or marketed.

In some examples, the sample is used directly in the methods described herein, or with minimal processing, such as cell lysis or addition of water or buffer. In other examples, the sample is processed to purify nucleic acids (such as RNA or DNA). The purified nucleic acids may be further processed, for example, reverse transcription of RNA to produce cDNA. In some embodiments, detecting the presence of a target nucleic acid (such as an influenza virus nucleic acid) in a sample includes the extraction of RNA from the sample. RNA extraction relates to releasing RNA from a latent or inaccessible form in a virion, cell, or sample and allowing the RNA to become freely available. In such a state, it is suitable for effective detection and/or amplification of the nucleic acid. Releasing viral RNA may include steps that achieve the disruption of virions containing viral RNA, as well as disruption of cells that may harbor such virions. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral or cellular components, wherein such components may be either particulate or dissolved. The RNA may further be reverse transcribed to produce cDNA for use in the methods described herein.

One of ordinary skill in the art will know suitable methods for extracting RNA from a sample; such methods will depend upon, for example, the type of sample in which the RNA is found. For example, the RNA may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. RNA can be extracted using standard methods. For instance, rapid RNA preparation can be performed using a commercially available kit (such as the MAGNA PURE@ Compact Nucleic Acid Isolation Kit I (Roche Applied Science, Pleasonton, CA); QIAAMP® Viral RNA Mini Kit, QIAAMP® MinElute Virus Spin Kit or RNEASY® Mini Kit (Qiagen, Valencia, CA); NUCLISENS® EASYMAG® or NUCLISENS® MINIMAG® nucleic acid isolation system (bioMdrieux, Durham, NC); ChargeSwitch® Total RNA Cell Kit (Life Technologies, Carlsbad, CA); or MASTERPURE™ Complete DNA and RNA Purification Kit (Epicentre Biotechnologies, Madison, WI)). Alternatively, a virion may be disrupted by a suitable detergent in the presence of proteases and/or inhibitors of ribonuclease activity. Additional exemplary methods for extracting RNA are found, for example, in World Health Organization, *Manual for the Virological Investigation of Polio*, World Health Organization, Geneva, 2001. In addition, one of ordinary skill in the art will know suitable methods for reverse transcribing RNA. For example, reverse transcription can be performed using commercially available kits (such as QuantiTect® reverse transcription kit (Qiagen, Valencia, CA); SuperScript® III cDNA synthesis kit or SuperScript® VILO cDNA synthesis kit (ThermoFisher Scientific, Waltham, MA); or High-Capacity cDNA reverse transcription kit (Applied Biosystems)).

The disclosed methods include contacting a sample containing or suspected to contain a target nucleic acid of interest with at least one set of probes (e.g., two probes) that hybridize to the target nucleic acid in the same region of the target nucleic acid. The two probes hybridize to the target nucleic acid within close enough proximity to one another that the gap between them can be filled efficiently and the resulting gap-filled nucleic acid is of a suitable size for downstream amplification methods (such as real-time PCR). In some examples, the two probes (e.g., an HP and BP) are separated by about 200 nucleotides or less (such as 175 nucleotides or less, 150 nucleotides or less, 125 nucleotides or less, 100 nucleotides or less, 90 nucleotides or less, 80 nucleotides or less, 70 nucleotides or less, 60 nucleotides or less, 50 nucleotides or less, 40 nucleotides or less, 30 nucleotides or less, 20 nucleotides or less, or 10 nucleotides or less) when the probes are hybridized to the target nucleic acid. In other examples, the two probes are separated by about 5-200 nucleotides (for example, about 5-10, 10-15, 10-30, 20-50, 30-60, 40-70, 50-80, 60-90, 70-100, 80-120, 100-150, 125-175, 150-200, or 5-120 nucleotides) when the probes are hybridized to the target nucleic acid. However, in some examples, the two probes can be separated by more than 100 nucleotides when hybridized to the target nucleic acid, provided that the resulting gap-filled nucleic acid has suitable characteristics for downstream steps (such as real-time PCR).

The HP and BP can be designed to hybridize to a target nucleic acid of interest. HP and BP can be highly degenerate and are thus not constrained by sequence variation. Furthermore, more than one set of probes (e.g., more than one set of HP/BP) may be designed for each target nucleic acid (such as each influenza virus HA or NA subtype), thereby taking account sequence diversity within a target nucleic acid. Thus, a plurality of HP and/or BP designed to hybridize to variants of a particular target nucleic acid (such as influenza HA or NA subtype variants) can be utilized in the disclosed methods (for example, conjugated to a single substrate or included in the same reaction mixture). Exemplary HP and BP for influenza virus nucleic acids are described in Section IV and Table 2 (below). However, one of ordinary skill in the art can design additional HP and BP for the detection of influenza virus nucleic acids or other nucleic acids of interest.

In particular embodiments of the methods disclosed herein, each probe in a set of probes (e.g., each HP and BP set) includes a first portion that is capable of hybridizing (specifically binding) to a target nucleic acid and a second portion that does not specifically bind to the target nucleic acid. The second portion is referred to herein as an adapter probe or AP. The second (AP) portion of the probe is covalently linked to the 5' or 3' end of the HP or BP (for example, by a phosphodiester bond). In some examples, the 5' end of the second portion of the probe is covalently linked to the 3' end of the first portion of the probe (e.g., 5'-HP-adapter-3' or 5'-BP-adapter-3'). In other examples, the 3' end of the second portion of the probe is covalently linked to the 5' end of the first portion of the probe (e.g., 5'-adapter-HP-3' or 5'-adapter-BP-3'). Exemplary APs are provided in Table 2; however, additional adapter sequences can be selected, depending on the target nucleic acid to be detected. For example, adapter sequences can be selected from sequences from a highly divergent organism (e.g., plant sequences or bacterial sequences (such as M13 plasmid sequence) can be utilized as adapters in an assay for detection viral nucleic acids).

In the methods disclosed herein, at least one of the two probes in the set of probes (e.g., at least the HP or the BP) is covalently linked or conjugated to a substrate. In particular examples, the HP or BP is conjugated to a bead that can subsequently be captured for enriching or purifying the gap-filled nucleic acid (such as a magnetic bead or a biotinylated bead). However, the probe can be conjugated to any suitable substrate or solid support, including a surface such as a plate (e.g., a multi-well plate) or a slide (such as a microarray). In particular examples, the probe is conjugated to a magnetic bead (for example, DynaBeads® magnetic beads (ThermoFisher Scientific, Waltham, MA), BioPlex magnetic beads (Bio-Rad Laboratories, Hercules, CA), MagPlex® microspheres (Luminex Corporation, Austin, TX)). In some examples, the magnetic beads are about 1 μm diameter, about 2.8 μm diameter, or about 4.5 μm diameter. In some examples, beads having a smaller diameter (e.g., 1 μm diameter) have a larger surface binding area and are less likely to precipitate from solution than larger beads, and may be advantageously used in the methods disclosed herein.

In some embodiments, the HP or BP is covalently linked to the substrate through the adapter portion of the probe. Thus, in some examples, the probe is an AP-HP probe that is covalently linked to the substrate at its 5' end (e.g., substrate-AP-HP). In other examples, the probe is a BP-AP probe that is covalently linked to the substrate at its 3' end (e.g., BP-AP-substrate). One of ordinary skill in the art can select the location of the covalent linkage (such as the 5' end or 3' end of an adapter or probe), such that the substrate does not substantially interfere with the steps of the method, such as hybridization to a target nucleic acid or amplification of a target nucleic acid.

The probe can be covalently linked to the substrate by a variety of approaches. In one example, probes are synthesized separately and then attached to a solid support. In another example, probes are synthesized directly onto the substrate. Suitable methods for covalently coupling probes to a solid support and for directly synthesizing probes onto a support are known to those working in the field; a summary of suitable methods can be found in Matson et al., *Anal. Biochem.* 217:306-10, 1994. In one example, the probe(s) are synthesized onto the support using conventional chemical techniques for preparing oligonucleotides on solid supports (such as PCT applications WO 85/01051 and WO 89/10977, or U.S. Pat. No. 5,554,501). In other examples, the probe(s) are covalently linked to the substrate by reacting a primary amine group on the probe (such as an amino modifier at the 5' or 3' end of the probe) with a reactive group on the substrate. In one non-limiting example, a probe with a 5' amino modifier is conjugated to a surface-activated substrate (such as a substrate with surface carboxylic acid groups) by reacting in the presence of 1-ethyl-3-[3-dimethylaminopropyl]carbodiimide hydrochloride (EDC). One of ordinary skill in the art can select other appropriate conjugation methods for covalently linking a probe to a substrate.

The disclosed methods include contacting a sample with at least one set of probes (e.g., at least one HP and at least one BP) under conditions sufficient for the probes to hybridize to the target nucleic acid, if it is present in the sample. At least one of the set of probes (e.g., one or both of the HP and BP probes) is covalently linked to a substrate (such as a magnetic bead). In particular examples, the sample is contacted with at least one HP conjugated to a magnetic bead and at least one corresponding BP under conditions sufficient for the HP and BP to hybridize (for example, stably hybridize) to target nucleic acid present in the sample. Hybridization conditions (such as time and temperature) can be determined by one of ordinary skill in the art. Among the hybridization reaction parameters that can be varied are type of salt and/or salt concentration, buffer, pH, temperature, time of incubation, amount and type of denaturant such as formamide.

Typically, the nucleic acid sequence of a probe will have sufficient complementarity to its corresponding target nucleic acid to enable it to hybridize under selected hybridization conditions, for example hybridization at about room temperature or higher (such as about 30° C., 37° C., 42° C., 50° C., 55° C., 60° C., 65° C., 70° C., 75° C., or higher). The hybridization is carried out for an amount of time sufficient to allow hybridization between the probe(s) and target nucleic acid, such as about 5 minutes to about 16 hours (e.g., overnight) or more, such as about 5 minutes, 10 minutes, 20 minutes, 30 minutes, 45 minutes, 60 minutes, 90 minutes, 2 hours, 3 hours, 4 hours, 6 hours, 8 hours, 12 hours, 16 hours, or more (for example, 20 minutes to 2 hours, 30 minutes to 1 hour, 1-3 hours, 2-8 hours, 4-12 hours, or 10-16 hours). One exemplary hybridization buffer is 6×SSPE-T (0.9 M NaCl, 60 mM NaH$_2$PO$_4$, 6 mM EDTA, and 0.05% Triton X-100). In some examples, TMAC is included in the hybridization buffer, for example about 3 M TMAC in the final working hybridization buffer. In one example, 1× TMAC buffer includes 3 M TMAC, 50 mM Tris-HCl, pH8, 0.4 mM EDTA, pH 8, 25% Formamide, 0.1% Sarkosyl, 100 µg/mL salmon testis DNA. In one non-limiting example, the substrate-conjugated HP, BP, and sample are incubated at 42° C. in 1× TMAC buffer for 30 minutes. In some examples, the substrate (including the HP, BP, and hybridized target nucleic acid) is washed one or more times, for example to remove non-hybridized nucleic acids and/or to change the buffer.

Following hybridization of the HP and BP probes to target nucleic acid, the gap between the hybridized HP and BP is filled, producing a gap-filled nucleic acid. The sample including the substrate with HP and BP hybridized to the target nucleic acid is contacted with reagents for gap filling, such as dNTPs, enzymes (for example, a DNA polymerase and/or a DNA ligase), and buffer under conditions sufficient for the synthesis of DNA between the hybridized HP and BP (gap-filling). Exemplary DNA polymerases include T4 DNA polymerase, DNA polymerase 3, T7 DNA polymerase, DNA polymerase IV, Taq DNA polymerase, and Klenow fragment. Exemplary DNA ligases include DNA ligases that can repair nicks in double-stranded DNA, such as T4 DNA ligase, ElectroLigase® (New England Biolabs, Ipswich, MA), T3 DNA ligase, T7 DNA ligase, E. coli DNA ligase, SplintR® DNA ligase (New England Biolabs), Taq DNA ligase, and ligase I. The sample including the HP and BP hybridized to the target nucleic acid is contacted with the gap-filling reagents under conditions sufficient for the gap to be filled. In some examples, the conditions include incubation at room temperature (e.g., 20-25° C.) for 5 to 30 minutes. In one non-limiting example, the substrate with HP and BP hybridized to the target nucleic acid is contacted with dNTPs (for example, 100 µM dNTPs), buffer (e.g., ligase buffer), DNA polymerase (e.g., T4 DNA polymerase), and DNA ligase (e.g., T4 DNA ligase) at room temperature for 10 minutes. In other examples, the DNA synthesis and ligation reactions can be performed sequentially, such as gap filling with a DNA polymerase at room temperature to 72° C., followed by ligation at 4° C. to room temperature.

Following gap-filling, the sample includes double-stranded DNA including the original target nucleic acid strand and the gap-filled strand including HP and BP, attached to the substrate. The double-stranded DNA is denatured and the strand attached to the substrate is isolated to produce enriched target nucleic acid. In some examples, the substrate is a magnetic bead, and isolation (enrichment) of the gap-filled strand is by capturing the beads with a magnet (such as a DynaMag™ magnet, ThermoFisher Scientific). In some examples, the denaturation conditions are mild conditions, such as incubation of the sample with NaOH (such as 0.2 NaOH) for a short period of time (for example, 2-10 minutes) prior to neutralization and isolation of the substrate-associated strand. However, one of ordinary skill in the art can select additional denaturation conditions (such as incubation at 95° C.) that can be used.

The enriched target nucleic acid is detected using an adapter-mediated amplification reaction. The amplification utilizes primers (universal adapter primers, UAP) that are complementary to all or a portion of the adapter probes that are attached to the HP and BP probes and thus are incorporated into the enriched target nucleic acid. Exemplary UAPs include SEQ ID NOs: 157 and 158; however, the UAPs can be modified or other UAPs can be used if different AP sequences are utilized. In some embodiments, the target nucleic acids are amplified prior to or substantially simultaneously with using a hybridization probe for detection. For instance, it can be advantageous to amplify the target nucleic acid, and detect the presence of the amplified target nucleic acid, for example, to increase the number of nucleic acids that can be detected, thereby increasing the signal obtained. The nucleic acid primers can be used to amplify a region that is at least about 50, at least about 60, at least about 70, at least about 80 at least about 90, at least about 100, at least about 200, at least about 300, or more base pairs in length to produce amplified target nucleic acids.

Any nucleic acid amplification method can be used to detect the presence of the target nucleic acid. In one specific, non-limiting example, polymerase chain reaction (PCR) is used to amplify the enriched target nucleic acid. In other specific, non-limiting examples, real-time PCR, reverse transcriptase-polymerase chain reaction (RT-PCR), real-time reverse transcriptase-polymerase chain reaction (rRT-PCR), ligase chain reaction, or transcription-mediated amplification is used to amplify and detect the enriched target nucleic acid. In a specific example, a target influenza virus nucleic acid is amplified by real-time PCR. In embodiments utilizing real-time PCR, the amplification reaction includes both the UAPs and a hydrolysis probe (TMP) specific for the target nucleic acid. Exemplary TMPs are described in Section IV and Example 1, below. Techniques for nucleic acid amplification are well-known to those of ordinary skill in the art.

Any type of thermal cycler apparatus can be used for the amplification of the target nucleic acids and/or the determination of hybridization. Examples of suitable apparatuses include PTC-100® Peltier Thermal Cycler (MJ Research, Inc., San Francisco, CA), ROBOCYCLER® 40 Temperature Cycler (Stratagene; La Jolla, CA), or a GENEAMP® PCR System 9700 (Applied Biosystems; Foster City, CA). For real-time PCR, any type of real-time thermocycler apparatus can be used. For example, AriaMX real-time PCR thermocycler (Agilent Technologies, Santa Clara, CA), Bio-Rad iCycler iQTM, LIGHTCYCLER™ (Roche; Mannheim, Germany), 7700 Sequence Detector (Perkin Elmer/Applied Biosystems; Foster City, CA), ABI™ systems such as the 7000, 7500, 7700, or 7900 systems (Applied Biosystems; Foster City, CA), or MX4000™, MX3000™ or MX3005™ (Stratagene; La Jolla, CA), and Cepheid SMARTCYCLER™ can be used to amplify nucleic acid sequences in real-time. One of ordinary skill in the art can select additional thermocycler platforms suitable for the methods disclosed herein.

In some embodiments, fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the nucleic acid of interest and in this way, using influenza type and/or subtype-specific probes, can detect the presence, identity, and/or amount of an influenza type and/or subtype in a sample. In one embodiment, fluorescently-labeled DNA probes used to identify amplification products have spectrally distinct emission wavelengths, thus allowing them to be distinguished within the same reaction tube (for example, using multiplex PCR, multiplex RT-PCR or multiplex rRT-PCR).

In some examples, the disclosed methods can predict with a sensitivity of at least 90% and a specificity of at least 90% for presence of an influenza virus nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In other examples, disclosed methods can detect presence of an influenza virus nucleic acid in a sample with a limit of detection (LOD) of about $1\text{-}10^8$ $EID_{50}$/ml, $10^2\text{-}10^6$ $EID_{50}$/ml, about $10^4\text{-}10^7$ $EID_{50}$/ml, about $1\text{-}10^4$ $EID_{50}$/ml, about $10^2\text{-}10^5$ $EID_{50}$/ml, or about $10^3\text{-}10^6$ $EID_{50}$/ml (such as about 1, 10, $10^2$, $10^3$, $10^4$, $10^5$, $10^6$, $10^7$, or $10^8$ $EID_{50}$/ml).

In some embodiments, the disclosed methods can be used to detect more than one target nucleic acid in a single reaction (e.g., multiplex methods). In some examples, the multiplexing occurs at the level of target enrichment. For example, multiple different probes can be conjugated to a single substrate, such as a single bead. In some examples, probes for up to five different target nucleic acids (such as 1, 2, 3, 4, or 5 different influenza virus subtypes) are conjugated to a single substrate. Thus, during the target enrichment steps, up to five different target nucleic acids can be purified in a reaction with a single population of beads. In addition, a single reaction can include two or more populations of substrates, each conjugated to up to 5 different target nucleic acid probes.

Figure 4A:
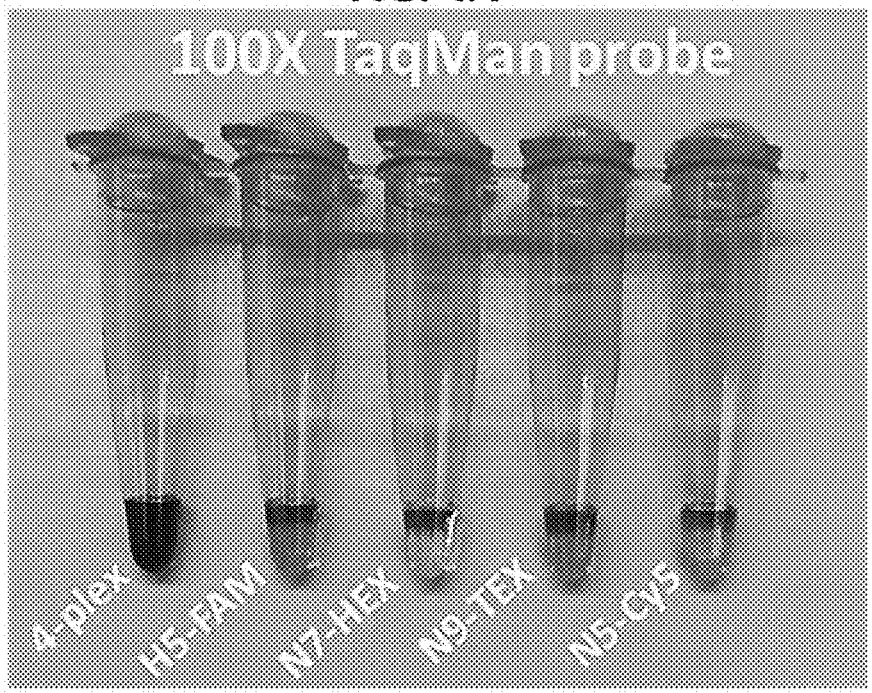
Figure 4A:
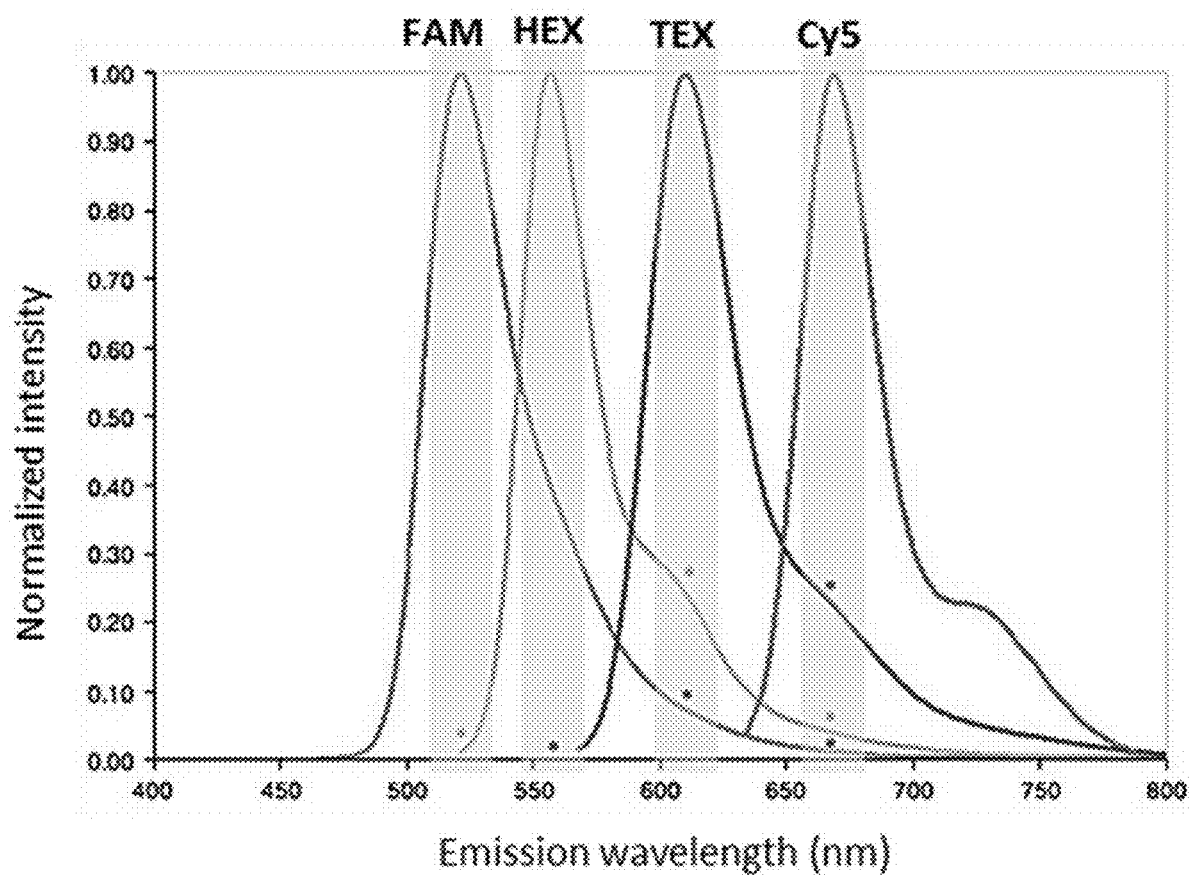

In other examples, the multiplexing occurs at the level of the adapter-mediated amplification and detection of the enriched target nucleic acid. For example, enriched target nucleic acids can be detected in a multiplex real-time PCR reaction including two or more (such as 2, 3, 4, 5, or more) hydrolysis probes in a single reaction (FIGS. 4A and 4B). In addition, the multiplexing can occur at both the target enrichment step (e.g., use of a substrate or population of substrates conjugated to 2 or more target nucleic acid probes) and the amplification and detection step (e.g., multiplex PCR).

In particular embodiments, the disclosed methods are used to detect presence of influenza virus nucleic acid in a sample, and may also be used to identify the subtype of influenza virus (e.g., H1 to H16 and/or N1 to N9). In some examples, the methods include contacting the sample with at least two probes comprising a first probe capable of hybridizing to a target influenza virus nucleic acid and a second probe capable of hybridizing to the target influenza virus nucleic acid under conditions sufficient for the first probe and the second probe to hybridize to the target influenza virus nucleic acid to produce a complex comprising the first probe, the second probe, and the target influenza virus nucleic acid, wherein the first probe and the second probe hybridize to the target influenza virus nucleic acid with a gap of 5-200 nucleotides between the first probe and the second probe and wherein one of the first probe and the second probe is covalently linked to a substrate, and wherein each of the first probe and the second probe each comprise a first portion capable of hybridizing to the target influenza virus nucleic acid and a second portion not capable of hybridizing to the target influenza virus nucleic acid. The complex comprising the first probe, the second probe, and the target influenza virus nucleic acid is contacted with one or more gap filling reagents under conditions sufficient to fill the gap between the first probe and the second probe, thereby producing gap-filled double-stranded target nucleic acid. The gap-filled double stranded target nucleic acid is denatured and the gap-filled target nucleic acid covalently linked to the substrate is isolated and the isolated gap-filled target nucleic acid covalently linked to the substrate is amplified by contacting the isolated gap-filled target nucleic acid covalently linked to the substrate with a pair of oligonucleotide primers complementary to at least a portion of the second portion of each of the first probe and the second probe. The amplified gap-filled target nucleic acid covalently linked to the substrate is measured by contacting the amplified gap-filled target nucleic acid covalently linked to the substrate with at least one detection probe capable of hybridizing to the target influenza virus nucleic acid, thereby detecting presence of the influenza virus in the sample.

In some examples, the methods include detecting presence of a N1 subtype influenza virus nucleic acid in the sample, wherein the first portion of the first probe comprises a nucleic acid sequence at least 90% identical to any one of SEQ ID NOs: 1 or 2, the first portion of the second probe comprises a nucleic acid sequence at least 90% identical to any one of SEQ ID NOs: 3-5, and the detection probe comprises a nucleic acid sequence at least 90% identical to SEQ ID NO: 6. In other examples, the methods include detecting presence of a N2 subtype influenza virus nucleic acid in the sample, wherein the first portion of the first probe comprises a nucleic acid sequence at least 90% identical to SEQ ID NO: 7, the first portion of the second probe comprises a nucleic acid sequence at least 90% identical to any one of SEQ ID NOs: 8 or 9, and the detection probe comprises a nucleic acid sequence at least 90% identical to any one of SEQ ID NOs: 10 or 11. In further examples, the methods include detecting presence of a N3 subtype influenza virus nucleic acid in the sample, wherein the first portion of the first probe comprises a nucleic acid sequence at least 90% identical to SEQ ID NO: 12, the first portion of the second probe comprises a nucleic acid sequence at least 90% identical to SEQ ID NO: 13, and the detection probe comprises a nucleic acid sequence at least 90% identical to SEQ ID NO: 14. In other examples, the methods include detecting presence of a N4 subtype influenza virus nucleic acid in the sample, wherein the first portion of the first probe comprises a nucleic acid sequence at least 90% identical to SEQ ID NO: 15, the first portion of the second probe comprises a nucleic acid sequence at least 90% identical to SEQ ID NO: 16, and the detection probe comprises a nucleic acid sequence at least 90% identical to SEQ ID NO: 17. In further examples, the methods include detecting presence of a N5 subtype influenza virus nucleic acid in the sample, wherein the first portion of the first probe comprises a nucleic acid sequence at least 90% identical to any one of SEQ ID NOs: 18-21, the first portion of the second probe comprises a nucleic acid sequence at least 90% identical to any one of SEQ ID NOs: 22-25, and the detection probe comprises a nucleic acid sequence at least 90% identical to any one of SEQ ID NOs: 26 or 27. In still further examples, the methods include detecting presence of a N6 subtype influenza virus nucleic acid in the sample, wherein the first portion of the first probe comprises a nucleic acid sequence at least 90% identical to any one of SEQ ID NOs: 28 or 29, the first portion of the second probe comprises a nucleic acid sequence at least 90% identical to any one of SEQ ID NOs:

30 or 31, and the detection probe comprises a nucleic acid sequence at least 90% identical to any one of SEQ ID NOs: 32 or 33. In other examples, the methods include detecting presence of a N7 subtype influenza virus nucleic acid in the sample, wherein the first portion of the first probe comprises a nucleic acid sequence at least 90% identical to SEQ ID NO: 34, the first portion of the second probe comprises a nucleic acid sequence at least 90% identical to any one of SEQ ID NOs: 35-39, and the detection probe comprises a nucleic acid sequence at least 90% identical to any one of SEQ ID NOs: 40-43. In additional examples, the methods include detecting presence of a N8 subtype influenza virus nucleic acid in the sample, wherein the first portion of the first probe comprises a nucleic acid sequence at least 90% identical to SEQ ID NO: 44, the first portion of the second probe comprises a nucleic acid sequence at least 90% identical to SEQ ID NO: 45, and the detection probe comprises a nucleic acid sequence at least 90% identical to SEQ ID NO: 46. In further examples, the methods include detecting presence of a N9 subtype influenza virus nucleic acid in the sample, wherein the first portion of the first probe comprises a nucleic acid sequence at least 90% identical to any one of SEQ ID NOs: 47 or 48, the first portion of the second probe comprises a nucleic acid sequence at least 90% identical to any one of SEQ ID NOs: 49 or 50, and the detection probe comprises a nucleic acid sequence at least 90% identical to SEQ ID NO: 51.

In some examples, the methods include detecting presence of a H1 subtype influenza virus nucleic acid in the sample, wherein the first portion of the first probe comprises a nucleic acid sequence at least 90% identical to any one of SEQ ID NOs: 52-54, the first portion of the second probe comprises a nucleic acid sequence at least 90% identical to any one of SEQ ID NOs: 55-57, and the detection probe comprises a nucleic acid sequence at least 90% identical to any one of SEQ ID NOs: 58 or 59. In other examples, the methods include detecting presence of a H2 subtype influenza virus nucleic acid in the sample, wherein the first portion of the first probe comprises a nucleic acid sequence at least 90% identical to SEQ ID NO: 60, the first portion of the second probe comprises a nucleic acid sequence at least 90% identical to SEQ ID NO: 61, and the detection probe comprises a nucleic acid sequence at least 90% identical to any one of SEQ ID NOs: 62 or 63. In further examples, the methods include detecting presence of a H3 subtype influenza virus nucleic acid in the sample, wherein the first portion of the first probe comprises a nucleic acid sequence at least 90% identical to SEQ ID NO: 64, the first portion of the second probe comprises a nucleic acid sequence at least 90% identical to any one of SEQ ID NOs: 65 or 66, and the detection probe comprises a nucleic acid sequence at least 90% identical to any one of SEQ ID NOs: 67 or 68. In still further examples, the methods include detecting presence of a H4 subtype influenza virus nucleic acid in the sample, wherein the first portion of the first probe comprises a nucleic acid sequence at least 90% identical to SEQ ID NO: 69, the first portion of the second probe comprises a nucleic acid sequence at least 90% identical to any one of SEQ ID NOs: 70 or 71, and the detection probe comprises a nucleic acid sequence at least 90% identical to any one of SEQ ID NOs: 72 or 73. In additional examples, the methods include detecting presence of a H5 subtype influenza virus nucleic acid in the sample, wherein the first portion of the first probe comprises a nucleic acid sequence at least 90% identical to any one of SEQ ID NOs: 74-79, the first portion of the second probe comprises a nucleic acid sequence at least 90% identical to any one of SEQ ID NOs: 80-85 and 159, and the detection probe comprises a nucleic acid sequence at least 90% identical to any one of SEQ ID NOs: 86-89 and 160. In other examples, the methods include detecting presence of a H6 subtype influenza virus nucleic acid in the sample, wherein the first portion of the first probe comprises a nucleic acid sequence at least 90% identical to any one of SEQ ID NOs: 90 or 91, the first portion of the second probe comprises a nucleic acid sequence at least 90% identical to any one of SEQ ID NOs: 92 or 93, and the detection probe comprises a nucleic acid sequence at least 90% identical to SEQ ID NO: 94. In further examples, the methods include detecting presence of a H7 subtype influenza virus nucleic acid in the sample, wherein the first portion of the first probe comprises a nucleic acid sequence at least 90% identical to any one of SEQ ID NOs: 95 or 96, the first portion of the second probe comprises a nucleic acid sequence at least 90% identical to any one of SEQ ID NOs: 97 or 98, and the detection probe comprises a nucleic acid sequence at least 90% identical to any one of SEQ ID NOs: 99 or 100. In still further examples, the methods include detecting presence of a H8 subtype influenza virus nucleic acid in the sample, wherein the first portion of the first probe comprises a nucleic acid sequence at least 90% identical to SEQ ID NO: 101, the first portion of the second probe comprises a nucleic acid sequence at least 90% identical to SEQ ID NO: 102, and the detection probe comprises a nucleic acid sequence at least 90% identical to SEQ ID NO: 103.

In some examples, the methods include detecting presence of a H9 subtype influenza virus nucleic acid in the sample, wherein the first portion of the first probe comprises a nucleic acid sequence at least 90% identical to any one of SEQ ID NOs: 104 or 105, the first portion of the second probe comprises a nucleic acid sequence at least 90% identical to any one of SEQ ID NOs: 106 or 107, and the detection probe comprises a nucleic acid sequence at least 90% identical to any one of SEQ ID NOs: 108-110. In other examples, the methods include detecting presence of a H10 subtype influenza virus nucleic acid in the sample, wherein the first portion of the first probe comprises a nucleic acid sequence at least 90% identical to SEQ ID NO: 111, the first portion of the second probe comprises a nucleic acid sequence at least 90% identical to SEQ ID NO: 112, and the detection probe comprises a nucleic acid sequence at least 90% identical to any one of SEQ ID NOs: 113-115. In yet other examples, the methods include detecting presence of a H11 subtype influenza virus nucleic acid in the sample, wherein the first portion of the first probe comprises a nucleic acid sequence at least 90% identical to SEQ ID NO: 116, the first portion of the second probe comprises a nucleic acid sequence at least 90% identical to any one of SEQ ID NOs: 117 or 118, and the detection probe comprises a nucleic acid sequence at least 90% identical to SEQ ID NO: 119. In further examples, the methods include detecting presence of a H12 subtype influenza virus nucleic acid in the sample, wherein the first portion of the first probe comprises a nucleic acid sequence at least 90% identical to SEQ ID NO: 120, the first portion of the second probe comprises a nucleic acid sequence at least 90% identical to SEQ ID NO: 121, and the detection probe comprises a nucleic acid sequence at least 90% identical to SEQ ID NO: 122. In still further examples, the methods include detecting presence of a H13 subtype influenza virus nucleic acid in the sample, wherein the first portion of the first probe comprises a nucleic acid sequence at least 90% identical to any one of SEQ ID NOs: 123 or 124, the first portion of the second probe comprises a nucleic acid sequence at least 90% identical to SEQ ID NO: 125, and the detection probe comprises a nucleic acid sequence at least 90% identical to any one of SEQ ID NOs: 126-128. In additional examples, the methods include detecting presence of a H14 subtype influenza virus nucleic acid in the sample, wherein the first portion of the first probe comprises a nucleic acid sequence at least 90% identical to SEQ ID NO: 129, the first portion of the second probe comprises a nucleic acid sequence at least 90% identical to SEQ ID NO: 130, and the detection probe comprises a nucleic acid sequence at least 90% identical to SEQ ID NO: 131. In other examples, the methods include detecting presence of a H15 subtype influenza virus nucleic acid in the sample, wherein the first portion of the first probe comprises a nucleic acid sequence at least 90% identical to SEQ ID NO: 132, the first portion of the second probe comprises a nucleic acid sequence at least 90% identical to SEQ ID NO: 133, and the detection probe comprises a nucleic acid sequence at least 90% identical to SEQ ID NO: 134. In further examples, the methods include detecting presence of a H16 subtype influenza virus nucleic acid in the sample, wherein the first portion of the first probe comprises a nucleic acid sequence at least 90% identical to SEQ ID NO: 135, the first portion of the second probe comprises a nucleic acid sequence at least 90% identical to any one of SEQ ID NOs: 136 or 137, and the detection probe comprises a nucleic acid sequence at least 90% identical to any one of SEQ ID NOs: 138-140.

In some examples, the disclosed methods also include detection of at least one control nucleic acid. For example, the methods can include contacting the sample with a set of probes that hybridize to a nucleic acid known to be present in the sample (e.g., a positive control target nucleic acid), such as β-actin or RNase P. In some examples, the control nucleic acid is avian β-action, and the methods include detecting avian β-action in the sample, wherein the first portion of the first control probe comprises a nucleic acid sequence at least 90% identical to SEQ ID NO: 152, the first portion of the second control probe comprises a nucleic acid sequence at least 90% identical to SEQ ID NO: 153, and the detection probe comprises a nucleic acid sequence at least 90% identical to SEQ ID NO: 154. In other examples, the positive control nucleic acid is a swine housekeeping gene, such as swine β-actin or RNase P.

Alternatively, the methods can include contacting a set of probes that hybridize to a nucleic acid known not to be present in the sample (e.g., a negative control). For example, a set of probes for a near neighbor target, such as influenza B can be included in the disclosed methods to serve as a negative control.

In further examples, the methods can include contacting the sample with a set of probes that hybridize to a nucleic acid that may be present in some avian samples, such as Newcastle disease virus (NDV). In some examples, the methods include detecting a NDV nucleic acid in the samples, wherein the first portion of the first probe comprises a nucleic acid sequence at least 90% identical to SEQ ID NO: 149, the first portion of the second probe comprises a nucleic acid sequence at least 90% identical to SEQ ID NO: 150, and the detection probe comprises a nucleic acid sequence at least 90% identical to SEQ ID NO: 151.

In still further examples, the disclosed methods can be used to detect or discriminate the presence of host cell infection (e.g., actively replicating influenza virus in a sample) or environmental exposure (e.g., contamination without replication in a sample). In such methods, the actively replicating influenza virus is detected by identifying the presence of influenza A (+) strand RNA. In some examples, the methods include detecting influenza A Matrix (+) strand RNA, wherein the first portion of the first probe comprises a nucleic acid sequence at least 90% identical to SEQ ID NO: 147, the first portion of the second probe comprises a nucleic acid sequence at least 90% identical to SEQ ID NO: 148, and the detection probe comprises a nucleic acid sequence at least 90% identical to SEQ ID NO: 146. In other examples, the environmental exposure is detected by identifying the presence of influenza A (−) stand RNA. In some examples, the methods include detecting influenza A Matrix (−) stand RNA, wherein the first portion of the first probe comprises a nucleic acid sequence at least 90% identical to SEQ ID NO: 144, the first portion of the second probe comprises a nucleic acid sequence at least 90% identical to SEQ ID NO: 145, and the detection probe comprises a nucleic acid sequence at least 90% identical to SEQ ID NO: 146.

In additional examples, the methods can be used to determine relative quantification of influenza A virus of different subtypes, for example by detecting mature (−)vRNA of influenza A virus. In some examples, the methods include detecting influenza A Matrix (−) stand RNA, wherein the first portion of the first probe comprises a nucleic acid sequence at least 90% identical to SEQ ID NO: 144, the first portion of the second probe comprises a nucleic acid sequence at least 90% identical to SEQ ID NO: 145, and the detection probe comprises a nucleic acid sequence at least 90% identical to SEQ ID NO: 146. In other examples, the methods include detecting influenza A Matrix (−) stand RNA, wherein the first portion of the first probe comprises a nucleic acid sequence at least 90% identical to SEQ ID NO: 141, the first portion of the second probe comprises a nucleic acid sequence at least 90% identical to SEQ ID NO: 142, and the detection probe comprises a nucleic acid sequence at least 90% identical to SEQ ID NO: 143.

IV. Probes and Primers

Probes capable of hybridizing to influenza virus nucleic acid and suitable for use in the disclosed methods are described herein. Also disclosed are primers that can be utilized for amplifying influenza virus nucleic acids (such as universal adapter primers) enriched or isolated using the methods described herein.

Probes capable of hybridizing to and/or detecting the presence of influenza nucleic acids are disclosed. The disclosed probes are between 20 and 60 nucleotides in length, such as 20, 21, 22, 23, 24, 25, 26, 27, 28, 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 (for example 20-40, 30-50, or 40-60) nucleotides in length and are capable of hybridizing to influenza virus nucleic acids. In several embodiments, a probe is capable of hybridizing to an influenza virus nucleic acid, such as an HA nucleic acid, for example an influenza virus H1-H16 nucleic acid, or an NA nucleic acid, for example, an influenza virus N1-N9 nucleic acid.

In several embodiments, a probe capable of hybridizing to an influenza virus nucleic acid includes a sequence that is at least 90% identical, such as at least 91%, at least 92%, at least 93%, at least 94%, at least 95%, at least 96%, at least 97%, at least 98%, at least 99%, or even 100% identical to the nucleic acid sequence of any one of SEQ ID NOs: 1-5, 7-9, 12, 13, 15, 16, 18-25, 28-31, 34-39, 44, 45, 47-50, 52-57, 60, 61, 64-66, 69-71, 74-85, 90-93, 95-98, 101, 102, 104-107, 111, 112, 116-118, 120, 121, 123-125, 129, 130, 132, 133, 135-137, 141, 142, 144, 145, 147-150, 152, or 153.

In several embodiments, a probe capable of hybridizing to an influenza nucleic acid consists essentially of a nucleic acid sequence with the sequence of any one of 1-5, 7-9, 12, 13, 15, 16, 18-25, 28-31, 34-39, 44, 45, 47-50, 52-57, 60, 61, 64-66, 69-71, 74-85, 90-93, 95-98, 101, 102, 104-107, 111, 112, 116-118, 120, 121, 123-125, 129, 130, 132, 133, 135-137, 141, 142, 144, 145, 147-150, 152, or 153.

In some embodiments, a probe capable of hybridizing to an influenza virus nucleic acid includes a first portion that specifically binds to (for example, is complementary to) an influenza virus nucleic acid and a second portion that does not specifically bind to (for example, is not complementary to) an influenza virus nucleic acid. In such examples, the first portion of the probe is referred to herein as a HP (such as SEQ ID NOs: 1, 2, 7, 12, 15, 18-21. 28, 29, 34, 44, 47, 48, 52-54, 60, 64, 69, 74-79, 90, 91, 95, 96, 101, 104, 105, 111, 116, 120, 123, 124, 129, 132, 135, 141, 144, 147, 149, or 152) or a BP (such as SEQ ID NOs: 3-5, 8, 9, 13, 16, 22-25, 30, 31, 35-39, 45, 49, 50, 55-57, 61, 65, 66, 70, 71, 80-85, 159, 92, 93, 97, 98, 102, 106, 107, 112, 117, 118, 121, 125, 130, 133, 136, 137, 142, 145, 148, 150, or 153). The second portion of such probes is referred to herein as an adapter oligonucleotide and includes a sequence that is at least 90% identical, such as at least 91%, at least 92%, at least 93%, at least 94%, at least 95%, at least 96%, at least 97%, at least 98%, at least 99%, or even 100% identical to the nucleic acid sequence of SEQ ID NO: 155 or SEQ ID NO: 156. In some examples, the adapter (second portion) consists essentially of a nucleic acid sequence of SEQ ID NO: 155 or SEQ ID NO: 156. One of ordinary skill in the art will appreciate that adapters with sequences other than those of SEQ ID NOs: 155 and 156 can be utilized in the disclosed methods, so long as the adapter sequences do not specifically bind to influenza virus nucleic acids. In some examples, the 5' end of the second portion of the probe is covalently linked to the 3' end of the first portion of the probe (e.g., 5'-HP-adapter-3' or 5'-BP-adapter-3'). In other examples, the 3' end of the second portion of the probe is covalently linked to the 5' end of the first portion of the probe (e.g., 5'-adapter-HP-3' or 5'-adapter-BP-3'). The covalent linkage between the first portion and the second portion is typically a phosphodiester bond; however, one of ordinary skill in the art can select other linkages that can be used.

In some embodiments, the probes disclosed herein also include a 5'- or 3'-end modification. The modifications can increase the stability of the probe (for example, decreasing or inhibiting probe degradation) or can be used to facilitate conjugation of the probe to a substrate (such as a surface or a bead). Exemplary modifications include molecules including a primary amino group, which can be used to attach an oligonucleotide to a solid surface or to attach a detectable label to an oligonucleotide. The amino group can be positioned at the 5'- or 3'-end of the probe and can include a carbon spacer (such as a C6 or C12 spacer). In one example, the modification is an amino modifier C6 (AmMC6) or amino modifier (AmMC12) and is attached at the 5'-end of a probe (such as at the 5'-end of a probe including an adapter-HP oligonucleotide). In another example, the modification is an amino modifier C6 (AmMC6) or amino modifier (AmMC12) and is attached at the 3'-end of a probe (such as at the 3'-end of a BP-adapter probe). In other examples, the probes include a 3' amino modifier (e.g., AmMO (IDT Technologies, Coralville, IA) that decreases degradation of the probe, for example, decreases digestion of the probe by a polymerase having 3' to 5' exonuclease activity (such as T4 DNA polymerase).

In some embodiments, a probe capable of hybridizing to an influenza virus nucleic acid is conjugated to a substrate. Substrates include a solid surface, such as a flat surface (for example, a plate or slide) or a spherical surface (for example, a bead). In particular examples, a probe capable of hybridizing to an influenza virus nucleic acid is conjugated to a bead, such as a magnetic bead. In one example, an HP probe or an adapter-HP probe is conjugated to a substrate (such as a magnetic bead) at its 5' end. In other examples, a BP probe or a BP-adapter probe is conjugated to a substrate (such as a magnetic bead) at its 3' end.

In some embodiments, the probe is detectably labeled, either with an isotopic or non-isotopic label. In particular examples, the hydrolysis probes (TMPs) used in the methods disclosed herein include a detectable label. In some examples, the TMPs (e.g., SEQ ID NOs: 6, 10, 11, 14, 17, 26, 27, 32, 33, 40-43, 46, 51, 58, 59, 62, 63, 67, 68, 72, 73, 86-89, 160, 94, 99, 100, 103, 108-110, 113-115, 119, 122, 126-128, 131, 134, 138-140, 143, 146, 151, and 154) include a detectable label, such as a 5' fluorophore and a 3' quencher, such as those shown in Example 1 and FIG. 5A. However, other fluorophore/quencher combinations or other detectable labels can be selected by one of skill in the art.

Non-isotopic labels for use with the probes described herein can include a fluorescent or luminescent molecule, a hapten (for example, biotin), an enzyme or enzyme substrate, or a chemical. Such labels are preferentially chosen such that the hybridization of the probe with target nucleic acid (such as an influenza nucleic acid) can be detected. In some examples, the probe is labeled with a fluorophore. Examples of suitable fluorophore labels are given below. In some examples, the fluorophore is a donor fluorophore. In other examples, the fluorophore is an accepter fluorophore, such as a fluorescence quencher. In some examples, the probe includes both a fluorophore and a quencher. Appropriate fluorophore/quencher pairs can be selected using routine methods.

In particular examples, the quencher is attached to the 3' end of the probe and the fluorophore is attached to a 5' end of the probe. In another particular example, the quencher is attached to a modified nucleotide (such as a T, for example, an internal T) and the fluorophore is attached to a 5' end of the probe. In a particular example, the quencher is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies).

Examples of particular fluorophores that can be used in the probes disclosed herein are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride);

4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as Atto 425-N-hydroxysuccinimide ester (Atto425), 5-carboxyfluorescein (FAM), 5-(4,6-dichlorotri-azin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; Cy5.5; Cy56-carboxyfluorescein; boron dipyrromethene difluoride (BODIPY); acridine; stilbene; TEXAS Red®; Cy3®; Cy5®, VIC@ (Applied Biosystems); LC Red 640; LC Red 705; and Yakima yellow, amongst others. Other suitable fluorophores include those known to those skilled in the art, for example those available from Molecular Probes (Eugene, OR). In particular examples, a fluorophore is used as a donor fluorophore or as an acceptor fluorophore.

In several embodiments, the probe (HP, BP, and/or TMP) is influenza subtype-specific. In some examples, an influenza subtype-specific probe is capable of hybridizing (for example, under high stringency or very high stringency conditions) to an influenza virus nucleic acid from a specific influenza subtype, such as an influenza virus H1, H2, H3, H4, H5, H6, H7, H8, H9, H10, H11, H12, H13, H14, H15, or H16 subtype. In other examples, an influenza subtype-specific probe is capable of hybridizing (for example, under high stringency or very high stringency conditions) to an influenza virus nucleic acid from an influenza virus N1, N2, N3, N4, N5, N6, N7, N8, or N9 subtype. In particular non-limiting examples, the disclosed influenza virus probes are N1 subtype-specific (for example, probes including a first portion of SEQ ID NOs: 1-6), N2 subtype-specific (for example, probes including a first portion of SEQ ID NOs: 7-11), N3 subtype-specific (for example, probes including a first portion of SEQ ID NOs: 12-14), N4 subtype-specific (for example, probes including a first portion of SEQ ID NOs: 15-17), N5 subtype-specific (for example, probes including a first portion of SEQ ID NOs: 18-27), N6 subtype-specific (for example, probes including a first portion of SEQ ID NOs: 28-33), N7 subtype-specific (for example, probes including a first portion of SEQ ID NOs: 34-43), N8 subtype-specific (for example, probes including a first portion of SEQ ID NOs: 44-46), or N9 subtype-specific (such as probes including a first portion of SEQ ID NOs: 47-51). In other examples, the disclosed influenza virus probes are H1 subtype-specific (for example, probes including a first portion of SEQ ID NOs: 52-59), H2 subtype-specific (for example, probes including a first portion of SEQ ID NOs: 60-63), H3 subtype-specific (for example, probes including a first portion of SEQ ID NOs: 64-68), H4 subtype-specific (for example, probes including a first portion of SEQ ID NOs: 69-73), H5 subtype-specific (for example, probes including a first portion of SEQ ID NOs: 74-89), H6 subtype-specific (for example, probes including a first portion of SEQ ID NOs: 90-94), H7 subtype-specific (for example, probes including a first portion of SEQ ID NOs: 95-100), H8 subtype-specific (for example, probes including a first portion of SEQ ID NOs: 101-103), H9 subtype-specific (for example, probes including a first portion of SEQ ID NOs: 104-110), H10 subtype-specific (for example, probes including a first portion of SEQ ID NOs: 111-115), H11 subtype-specific (for example, probes including a first portion of SEQ ID NOs: 116-119), H12 subtype-specific (for example, probes including a first portion of SEQ ID NOs: 120-122), H13 subtype-specific (for example, probes including a first portion of SEQ ID NOs: 123-128), H14 subtype-specific (for example, probes including a first portion of SEQ ID NOs: 129-131), H15 subtype-specific (for example, probes including a first portion of SEQ ID NOs: 132-134), or H16 subtype-specific (for example, probes including a first portion of SEQ ID NOs: 135-140). In other embodiments, the probe is not subtype-specific, but is specific for influenza A (for example, probes including a first portion of SEQ ID NOs: 141-148).

Subtype-specific probes (such as subtype-specific HP and/or BP) can be used to detect the presence of and/or differentiate between various influenza subtypes. Such probes are specific for one influenza subtype, for example specific for an influenza virus HA nucleic acid that is subtype-specific (such as H1, H2, H3, H4, H5, H6, H7, H8, H9, H10, H11, H12, H13, H14, H15, or H16) or an influenza virus NA nucleic acid that is subtype-specific (such as N1, N2, N3, N4, N5, N6, N7, N8, or N9). In particular non-limiting examples, the probe (HP or BP) is specific for an H1, H2, H3, H4, H5, H6, H7, H8, H9, H10, H11, H12, H13, H14, H15, or H16 nucleic acid or an N1, N2, N3, N4, N5, N6, N7, N8, or N9 nucleic acid.

In certain embodiments the probes are included in a set of probes, such as two or more (for example, 2-100, 10-50, 20-60, 2-30, 5-15, 10-20, or 15-30, such as 2, 3, 4, 5, 6, 7, 8, 9, 10, or more) probes capable of hybridizing to an influenza virus nucleic acid. In some examples, the set of probes includes one or more probes that are specific for a single influenza virus subtype (such as 2, 3, 4, 5, 6, 7, 8, 9, or more probes specific for a single influenza virus subtype). Thus, in some examples, a set of probes includes at least one N1 subtype-specific HP and at least one N1 subtype-specific BP (for example, one or more first probes with a first portion of SEQ ID NO: 1 or 2 and one or more second probes with a first portion of SEQ ID NOs: 4-6), at least one N2 subtype-specific HP and at least one N2 subtype-specific BP (for example, a first probe with a first portion of SEQ ID NO: 7 and one or more second probes with a first portion of SEQ ID NO: 8 or 9), at least one N3 subtype-specific HP and at least one N3 subtype-specific BP (for example, a first probe with a first portion of SEQ ID NO: 12 and one or more second probes with a first portion of SEQ ID NO: 13), at least one N4 subtype-specific HP and at least one N4 subtype-specific BP (for example, a first probe with a first portion of SEQ ID NO: 15 and one or more second probes with a first portion of SEQ ID NO: 16), at least one N5 subtype-specific HP and at least one N5 subtype-specific BP (for example, one or more first probes with a first portion of SEQ ID NOs: 18-21 and one or more second probes with a first portion of SEQ ID NOs: 22-25), at least one N6 subtype-specific HP and at least one N6 subtype-specific BP (for example, one or more first probe with a first portion of SEQ ID NOs: 28 or 29 and one or more second probes with a first portion of SEQ ID NO: 30 or 31), at least one N7 subtype-specific HP and at least one N7 subtype-specific BP (for example, a first probe with a first portion of SEQ ID NO: 34 and one or more second probes with a first portion of SEQ ID NO: 35-39), at least one N8 subtype-specific HP and at least one N8 subtype-specific BP (for example, a first probe with a first portion of SEQ ID NO: 44 and a second probe with a first portion of SEQ ID NO: 45), and/or at least one N9 subtype-specific HP and at least one N9 subtype-specific BP (for example, one or more first probes with a first portion of SEQ ID NO: 47 or 48 and one or more second probes with a first portion of SEQ ID NO: 49 or 50.

In other examples, the set of probes includes at least one H1 subtype-specific HP and at least one H1 subtype-specific BP (for example, one or more first probes with a first portion of SEQ ID NO: 52-54 and one or more second probes with a first portion of SEQ ID NO: 55-57), at least one H2 subtype-specific HP and at least one H2 subtype-specific BP (for example, a first probe with a first portion of SEQ ID NO: 60 and a second probe with a first portion of SEQ ID NO: 61), at least one H3 subtype-specific HP and at least one H3 subtype-specific BP (for example, a first probe with a first portion of SEQ ID NO: 64 and one or more second probes with a first portion of SEQ ID NO: 65 or 66), at least one H4 subtype-specific HP and at least one H4 subtype-specific BP (for example, a first probe with a first portion of SEQ ID NO: 69 and one or more second probes with a first portion of SEQ ID NO: 70 or 71), at least one H5 subtype-specific HP and at least one H5 subtype-specific BP (for example, one or more first probes with a first portion of SEQ ID NO: 74-79 and one or more second probes with a first portion of SEQ ID NO: 80-85 or 159), at least one H6 subtype-specific HP and at least one H6 subtype-specific BP (for example, one or more first probes with a first portion of SEQ ID NO: 90 or 91 and one or more second probes with a first portion of SEQ ID NO: 92 or 93), at least one H7 subtype-specific HP and at least one H7 subtype-specific BP (for example, one or more first probes with a first portion of SEQ ID NO: 95 or 96 and one or more second probes with a first portion of SEQ ID NO: 97 or 98), at least one H8 subtype-specific HP and at least one H8 subtype-specific BP (for example, a first probe with a first portion of SEQ ID NO: 101 and a second probe with a first portion of SEQ ID NO:102), at least one H9 subtype-specific HP and at least one H9 subtype-specific BP (for example, one or more first probes with a first portion of SEQ ID NO: 104 or 105 and one or more second probes with a first portion of SEQ ID NO: 106 or 107), at least one H10 subtype-specific HP and at least one H10 subtype-specific BP (for example, a first probe with a first portion of SEQ ID NO: 111 and a second probe with a first portion of SEQ ID NO: 112), at least one H11 subtype-specific HP and at least one H11 subtype-specific BP (for example, a first probe with a first portion of SEQ ID NO: 116 and one or more second probes with a first portion of SEQ ID NO: 117 or 118), at least one H12 subtype-specific HP and at least one H12 subtype-specific BP (for example, a first probe with a first portion of SEQ ID NO: 120 and a second probe with a first portion of SEQ ID NO: 112), at least one H13 subtype-specific HP and at least one H13 subtype-specific BP (for example, one or more first probes with a first portion of SEQ ID NO: 123 or 124 and a second probe with a first portion of SEQ ID NO: 125), H13 subtype-specific probes (for example, two or more of probes including a first portion of SEQ ID NOs: 123-128), at least one H14 subtype-specific HP and at least one H14 subtype-specific BP (for example, a first probe with a first portion of SEQ ID NO: 129 and a second probe with a first portion of SEQ ID NO: 130), at least one H15 subtype-specific HP and at least one H15 subtype-specific BP (for example, a first probe with a first portion of SEQ ID NO: 132 and a second probe with a first portion of SEQ ID NO: 133), and/or at least one H16 subtype-specific HP and at least one H16 subtype-specific BP (for example, a first probe with a first portion of SEQ ID NO: 135 and one or more second probes with a first portion of SEQ ID NO: 136 or 137). In other examples, the set of probes includes two or more influenza A specific probes (for example, one or more first probes with a first portion of SEQ ID NO: 141, 144, or 147 and one or more second probes with a first portion of SEQ ID NO: 142, 245, or 148). In further examples, the set of probes includes at least one Newcastle disease virus-specific HP (such as a first probe with a first portion of SEQ ID NO: 149) and at least one Newcastle disease virus-specific BP (such as a second probe with a first portion of SEQ ID NO: 150) and/or at least one β-actin-specific HP (such as a first probe with a first portion of SEQ ID NO: 152) and at least one 3-actin-specific BP (such as a second probe with a first portion of SEQ ID NO: 153).

In some embodiments, the set of probes includes two or more subtype-specific HP probes (e.g., first probes) conjugated to a substrate (such as a bead, for example a magnetic). The two or more probes may be specific for the same influenza virus subtype (such as two or more H5 subtype-specific probes) or may be specific for two or more different influenza subtypes.

In other embodiments, the set of probes includes at least one HP (for example, at least one HP (or first probe) conjugated to a substrate) and at least one BP (or second probe) for a particular influenza virus type or subtype. Thus, in some examples, a set of probes is a set of N1 subtype-specific probes (for example, two or more of probes including a first portion of SEQ ID NOs: 1-6), a set of N2 subtype-specific probes (for example, two or more of probes including a first portion of SEQ ID NOs: 7-11), a set of N3 subtype-specific probes (for example, two or more of probes including a first portion of SEQ ID NOs: 12-14), a set of N4 subtype-specific probes (for example, two or more of probes including a first portion of SEQ ID NOs: 15-17), a set of N5 subtype-specific probes (for example, two or more of probes including a first portion of SEQ ID NOs: 18-27), a set of N6 subtype-specific probes (for example, two or more of probes including a first portion of SEQ ID NOs: 28-33), a set of N7 subtype-specific probes (for example, two or more of probes including a first portion of SEQ ID NOs: 34-43), a set of N8 subtype-specific probes (for example, two or more of probes including a first portion of SEQ ID NOs: 44-46), or a set of N9 subtype-specific probes (such as two or more of probes including a first portion of SEQ ID NOs: 47-51). In other examples, set of probes includes a set of H1 subtype-specific probes (for example, two or more of probes including a first portion of SEQ ID NOs: 52-59), a set of H2 subtype-specific probes (for example, two or more of probes including a first portion of SEQ ID NOs: 60-63), a set of H3 subtype-specific probes (for example, two or more of probes including a first portion of SEQ ID NOs: 64-68), a set of H4 subtype-specific probes (for example, two or more of probes including a first portion of SEQ ID NOs: 69-73), a set of H5 subtype-specific probes (for example, two or more of probes including a first portion of SEQ ID NOs: 74-89), a set of H6 subtype-specific probes (for example, two or more of probes including a first portion of SEQ ID NOs: 90-94), a set of H7 subtype-specific probes (for example, two or more of probes including a first portion of SEQ ID NOs: 95-100), a set of H8 subtype-specific probes (for example, two or more of probes including a first portion of SEQ ID NOs: 101-103), a set of H9 subtype-specific probes (for example, two or more of probes including a first portion of SEQ ID NOs: 104-110), a set of H10 subtype-specific probes (for example, two or more of probes including a first portion of SEQ ID NOs: 111-115), a set of H11 subtype-specific probes (for example, two or more of probes including a first portion of SEQ ID NOs: 116-119), a set of H12 subtype-specific probes (for example, two or more of probes including a first portion of SEQ ID NOs: 120-122), a set of H13 subtype-specific probes (for example, two or more of probes including a first portion of SEQ ID NOs: 123-128), a set of H14 subtype-specific probes (for example, two or more of probes including a first portion of SEQ ID NOs: 129-131), a set of H15 subtype-specific probes (for example, two or more of probes including a first portion of SEQ ID NOs: 132-134), or a set of H16 subtype-specific probes (for example, two or more of probes including a first portion of SEQ ID NOs:135-140).

In still further embodiments, a set of probes includes one or more TMPs (e.g., detection probes) for a particular influenza virus type or subtype, or two or more influenza virus TMPs. Thus, in some examples, a set of probes includes one or more N1 subtype-specific detection probes (for example a probe including SEQ ID NO: 6), one or more N2 subtype-specific detection probes (for example a probe including SEQ ID NO: 10 or 11), one or more N3 subtype-specific detection probes (for example a probe including SEQ ID NO: 14), one or more N4 subtype-specific detection probes (for example a probe including SEQ ID NO: 17), one or more N5 subtype-specific detection probes (for example a probe including SEQ ID NO: 26 or 27), one or more N6 subtype-specific detection probes (for example a probe including SEQ ID NO: 32 or 33), one or more N7 subtype-specific detection probes (for example a probe including SEQ ID NO: 40-43), one or more N8 subtype-specific detection probes (for example a probe including SEQ ID NO: 46), one or more N9 subtype-specific detection probes (for example a probe including SEQ ID NO: 51), one or more H1 subtype-specific detection probes (for example a probe including SEQ ID NO: 58 or 59), one or more H2 subtype-specific detection probes (for example a probe including SEQ ID NO: 62 or 63), one or more H3 subtype-specific detection probes (for example a probe including SEQ ID NO: 67 or 68), one or more H4 subtype-specific detection probes (for example a probe including SEQ ID NO: 72 or 73), one or more H5 subtype-specific detection probes (for example a probe including SEQ ID NO: 86-89 or 160), one or more H6 subtype-specific detection probes (for example a probe including SEQ ID NO: 94), one or more H7 subtype-specific detection probes (for example a probe including SEQ ID NO: 99 or 100), one or more H8 subtype-specific detection probes (for example a probe including SEQ ID NO: 103), one or more H9 subtype-specific detection probes (for example a probe including SEQ ID NO: 108-110), one or more H10 subtype-specific detection probes (for example a probe including SEQ ID NO: 113-115), one or more H11 subtype-specific detection probes (for example a probe including SEQ ID NO: 119), one or more H12 subtype-specific detection probes (for example a probe including SEQ ID NO: 122), one or more H13 subtype-specific detection probes (for example a probe including SEQ ID NO: 126-128), one or more H14 subtype-specific detection probes (for example a probe including SEQ ID NO: 131), one or more H15 subtype-specific detection probes (for example a probe including SEQ ID NO: 134), and/or one or more H16 subtype-specific detection probes (for example a probe including SEQ ID NO: 138-140). In some examples, the set of probes also includes one or more influenza A virus-specific detection probes (for example, one or more probes including SEQ ID NO: 143 or 146), one or more Newcastle virus-specific detection probes (for example, a probe including SEQ ID NO: 151), and/or a β-actin-specific detection probe (for example, a probe including SEQ ID NO: 154).

Also disclosed are primers capable of hybridizing to and directing the amplification of nucleic acids enriched using the methods disclosed herein. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or 40 (for example 15-30, 20-30, or 25-40) nucleotides in length. In several embodiments, the primer is capable of specifically binding to and directing the amplification of the enriched influenza virus nucleic acid or a portion thereof. In particular examples, the primers are "universal" primers that are capable of binding to and directing amplification of nucleic acids that include the adapter nucleic acids disclosed herein. Thus, in some examples, the primers include or are complementary to all or a portion of one of the disclosed adapter probe sequences (e.g., include or are complementary to SEQ ID NOs: 155 or 156). Exemplary forward and reverse universal primers include or consist of SEQ ID NOs: 157 and 158, respectively.

In certain embodiments the primers are included in a set of primers, such as a pair of primers, capable of hybridizing to and amplifying an enriched influenza virus nucleic acid. Such a set of primers comprises at least one forward primer and at least one reverse primer, where the primers are specific for the amplification of an influenza subtype nucleic acid. In some examples, the set of primers includes primers including or consisting of the sequences of SEQ ID NOs: 157 and 158.

Although exemplary probes and primers are provided in SEQ ID NOs: 1-158, one skilled in the art will appreciate that the primer or probe sequences can be varied slightly by moving the probe or primer a few nucleotides upstream or downstream from the nucleotide positions that they hybridize to on the influenza nucleic acid, provided that the probe or primer is still specific for an influenza virus sequence, such as specific for the subtype of the influenza sequence. For example, one of ordinary skill in the art will appreciate that by analyzing sequence alignments of influenza type or subtype genes that variations of the probes or primers disclosed herein can be made for example, by "sliding" the probes and/or primers a few nucleotides 5' or 3' from their positions, and that such variation will still be specific for the influenza viral subtype.

Also provided by the present application are probes and primers that include variations to the nucleotide sequences shown in any of SEQ ID NOs: 1-158, as long as such variations permit detection of the influenza virus nucleic acid, such as an influenza subtype nucleic acid. For example, a probe or primer can have at least 90% sequence identity such as at least 91%, at least 92%, at least 93%, at least 94%, at least 95%, at least 96%, at least 97%, at least 98%, at least 99% to a nucleic acid consisting of the sequence shown in any of SEQ ID NOs: 1-158. In some examples, the number of nucleotides does not change, but the nucleic acid sequence shown in any of SEQ ID NOs: 1-158 can vary at a few nucleotides, such as changes at 1, 2, 3, or 4 nucleotides.

The present application also provides probes and primers that are slightly longer or shorter than the nucleotide sequences shown in any of SEQ ID NOs: 1-158, as long as such deletions or additions permit detection or amplification of the desired influenza nucleic acid, such as an influenza subtype. For example, a probe or primer can include a few nucleotide deletions or additions at the 5'- and/or 3'-end of the probe or primer shown in any of SEQ ID NOs: 1-158, such as addition or deletion of 1, 2, 3, or 4 nucleotides from the 5'- or 3'-end, or combinations thereof (such as a deletion from one end and an addition to the other end). In such examples, the number of nucleotides may change. One of skill in the art will appreciate that sequence alignments provide sufficient guidance as to what additions and/or subtractions can be made, while still maintaining specificity for the influenza viral subtype.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In other examples, the probes and/or primers include one or more synthetic bases or alternative bases (such as inosine). In other examples, the probes and/or primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, WA). In other examples, the probes and primers disclosed herein include a minor groove binder conjugated to the 5' or 3' end of the oligonucleotide (see, e.g., U.S. Pat. No. 6,486,308). In particular examples, to improve annealing temperature of a probe with low GC content or short sequences, one or more locked nucleic acids (LNA) and/or a minor grove binding (MGB) moiety is included in a probe.

V. Kits

The nucleic acid probes and primers disclosed herein can be supplied in the form of a kit for use in the detection, typing, and/or subtyping of a target nucleic acid, such as an influenza virus nucleic acid. In such a kit, an appropriate amount of one or more of the nucleic acid probes and/or primers is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid probes for use in detection, typing, and/or subtyping of nucleic acids (such as influenza virus nucleic acids). The kits can additionally include one or more control samples, probes, and/or primers.

In some examples, the kits include two or more probes for detection of a target nucleic acid. The kits may include at least one HP and at least one BP that are capable of specifically hybridizing to a target nucleic acid. In some examples, at least one of the HP or BP in the kit is covalently linked to a substrate. In other examples, the probes are not covalently linked to a substrate and the kit may optionally include a substrate and/or reagents for covalently linking a HP or BP to the substrate. The kits may also include at least one hydrolysis probe for detection of the target nucleic acid that is enriched with the HP and BP using the methods described herein.

In some embodiments, kits also may include the reagents necessary to carry out hybridization and/or PCR amplification reactions, including one or more of nucleic acid sample preparation reagents, appropriate buffers (such as hybridization buffer, polymerase buffer, and/or ligase buffer), salts (for example, TMAC), and deoxyribonucleotides (dNTPs), or enzymes (such as DNA polymerase and/or DNA ligase). In one example, the kits include a hybridization buffer, such as a buffer including TMAC (for example, a buffer that includes 3 M TMAC at working (1×) concentration, such as 3 M TMAC, 50 mM Tris-HCl, pH 8.0, 2 mM EDTA, 1 mg/ml SDS).

In certain embodiments the kit includes a set of probes, such as two or more (for example, 2-30, 5-15, 10-20, or 15-30, such as 2, 3, 4, 5, 6, 7, 8, 9, 10, or more) probes capable of hybridizing to an influenza virus nucleic acid. In some examples, the set of probes includes one or more probes that are specific for a single influenza virus subtype (such as 2, 3, 4, 5, 6, 7, 8, 9, or more probes specific for a single influenza virus subtype). In particular examples, the set of probes includes sets of probes as shown in FIG. 5, such as a set of probes for detection of subtypes H8, N8, N7, H4, H2, a set of probes for detection of subtypes H9, H4, and H7 (optionally also including probes for detection of NDV and InfA(−)strand RNA), a set of probes for detection of subtypes N6, N4, H12, and H3 (optionally also including probes for detection of InfA(+)strand RNA), a set of probes for detection of subtypes H11, N1, H14, H3, and H6, a set of probes for detection of subtypes H16, H10, N2, and N5 (optionally also including probes for detection of a control, such as β-actin), and/or a set of probes for detection of subtypes H13, H15, N9, and H1 (optionally also including probes for detection of a control, such as a swine gene, for example, swine β-actin).

Thus, in some examples, a set of probes is N1 subtype-specific (for example, probes including a first portion of SEQ ID NOs: 1-6), N2 subtype-specific (for example, probes including a first portion of SEQ ID NOs: 7-11), N3 subtype-specific (for example, probes including a first portion of SEQ ID NOs: 12-14), N4 subtype-specific (for example, probes including a first portion of SEQ ID NOs: 15-17), N5 subtype-specific (for example, probes including a first portion of SEQ ID NOs: 18-27), N6 subtype-specific (for example, probes including a first portion of SEQ ID NOs: 28-33), N7 subtype-specific (for example, probes including a first portion of SEQ ID NOs: 34-43), N8 subtype-specific (for example, probes including a first portion of SEQ ID NOs: 44-46), or N9 subtype-specific (such as probes including a first portion of SEQ ID NOs: 47-51). In other examples, the disclosed influenza virus probes are H1 subtype-specific (for example, probes including a first portion of SEQ ID NOs: 52-59), H2 subtype-specific (for example, probes including a first portion of SEQ ID NOs: 60-63), H3 subtype-specific (for example, probes including a first portion of SEQ ID NOs: 64-68), H4 subtype-specific (for example, probes including a first portion of SEQ ID NOs: 69-73), H5 subtype-specific (for example, probes including a first portion of SEQ ID NOs: 74-89), H6 subtype-specific (for example, probes including a first portion of SEQ ID NOs: 90-94), H7 subtype-specific (for example, probes including a first portion of SEQ ID NOs: 95-100), H8 subtype-specific (for example, probes including a first portion of SEQ ID NOs: 101-103), H9 subtype-specific (for example, probes including a first portion of SEQ ID NOs: 104-110), H10 subtype-specific (for example, probes including a first portion of SEQ ID NOs: 111-115), H11 subtype-specific (for example, probes including a first portion of SEQ ID NOs: 116-119), H12 subtype-specific (for example, probes including a first portion of SEQ ID NOs: 120-122), H13 subtype-specific (for example, probes including a first portion of SEQ ID NOs: 123-128), H14 subtype-specific (for example, probes including a first portion of SEQ ID NOs: 129-131), H15 subtype-specific (for example, probes including a first portion of SEQ ID NOs: 132-134), or H16 subtype-specific (for example, probes including a first portion of SEQ ID NOs:135-140). In other embodiments, the probe is not subtype-specific, but is specific for influenza A (for example, probes including a first portion of SEQ ID NOs: 141-148).

In some embodiments, the set of probes in the kit includes two or more subtype-specific HP probes conjugated to a substrate (such as a bead). The two or more probes may be specific for the same influenza virus subtype (such as two or more H5 subtype-specific probes) or may be specific for two or more different influenza subtypes.

In other embodiments, the set of probes in the kit includes at least one HP (for example, at least one HP probe conjugated to a substrate) and at least one BP for a particular influenza virus type or subtype. Thus, in some examples, the set of probes in the kit includes at least one H1 subtype-specific HP and at least one H1 subtype-specific BP (for example, one or more first probes with a first portion of SEQ ID NO: 52-54 and one or more second probes with a first portion of SEQ ID NO: 55-57), at least one H2 subtype-specific HP and at least one H2 subtype-specific BP (for example, a first probe with a first portion of SEQ ID NO: 60 and a second probe with a first portion of SEQ ID NO: 61), at least one H3 subtype-specific HP and at least one H3 subtype-specific BP (for example, a first probe with a first portion of SEQ ID NO: 64 and one or more second probes with a first portion of SEQ ID NO: 65 or 66), at least one H4 subtype-specific HP and at least one H4 subtype-specific BP (for example, a first probe with a first portion of SEQ ID NO: 69 and one or more second probes with a first portion of SEQ ID NO: 70 or 71), at least one H5 subtype-specific HP and at least one H5 subtype-specific BP (for example, one or more first probes with a first portion of SEQ ID NO: 74-79 and one or more second probes with a first portion of SEQ ID NO: 80-85 or 159), at least one H6 subtype-specific HP and at least one H6 subtype-specific BP (for example, one or more first probes with a first portion of SEQ ID NO: 90 or 91 and one or more second probes with a first portion of SEQ ID NO: 92 or 93), at least one H7 subtype-specific HP and at least one H7 subtype-specific BP (for example, one or more first probes with a first portion of SEQ ID NO: 95 or 96 and one or more second probes with a first portion of SEQ ID NO: 97 or 98), at least one H8 subtype-specific HP and at least one H8 subtype-specific BP (for example, a first probe with a first portion of SEQ ID NO: 101 and a second probe with a first portion of SEQ ID NO:102), at least one H9 subtype-specific HP and at least one H9 subtype-specific BP (for example, one or more first probes with a first portion of SEQ ID NO: 104 or 105 and one or more second probes with a first portion of SEQ ID NO: 106 or 107), at least one H10 subtype-specific HP and at least one H10 subtype-specific BP (for example, a first probe with a first portion of SEQ ID NO: 111 and a second probe with a first portion of SEQ ID NO: 112), at least one H11 subtype-specific HP and at least one H11 subtype-specific BP (for example, a first probe with a first portion of SEQ ID NO: 116 and one or more second probes with a first portion of SEQ ID NO: 117 or 118), at least one H12 subtype-specific HP and at least one H12 subtype-specific BP (for example, a first probe with a first portion of SEQ ID NO: 120 and a second probe with a first portion of SEQ ID NO: 112), at least one H13 subtype-specific HP and at least one H13 subtype-specific BP (for example, one or more first probes with a first portion of SEQ ID NO: 123 or 124 and a second probe with a first portion of SEQ ID NO: 125), H13 subtype-specific probes (for example, two or more of probes including a first portion of SEQ ID NOs: 123-128), at least one H14 subtype-specific HP and at least one H14 subtype-specific BP (for example, a first probe with a first portion of SEQ ID NO: 129 and a second probe with a first portion of SEQ ID NO: 130), at least one H15 subtype-specific HP and at least one H15 subtype-specific BP (for example, a first probe with a first portion of SEQ ID NO: 132 and a second probe with a first portion of SEQ ID NO: 133), and/or at least one H16 subtype-specific HP and at least one H16 subtype-specific BP (for example, a first probe with a first portion of SEQ ID NO: 135 and one or more second probes with a first portion of SEQ ID NO: 136 or 137). In other examples, the set of probes in the kit includes two or more influenza A specific probes (for example, one or more first probes with a first portion of SEQ ID NO: 141, 144, or 147 and one or more second probes with a first portion of SEQ ID NO: 142, 245, or 148). In further examples, the set of probes in the kit includes at least one Newcastle disease virus-specific HP (such as a first probe with a first portion of SEQ ID NO: 149) and at least one Newcastle disease virus-specific BP (such as a second probe with a first portion of SEQ ID NO: 150) and/or at least one β-actin-specific HP (such as a first probe with a first portion of SEQ ID NO: 152) and at least one β-actin-specific BP (such as a second probe with a first portion of SEQ ID NO: 153).

In still further embodiments, the kit includes one or more TMPs for a particular influenza virus type or subtype, or one or more influenza virus TMPs. Thus, in some examples, the kit includes one or more N1 subtype-specific detection probes (for example a probe including SEQ ID NO: 6), one or more N2 subtype-specific detection probes (for example a probe including SEQ ID NO: 10 or 11), one or more N3 subtype-specific detection probes (for example a probe including SEQ ID NO: 14), one or more N4 subtype-specific detection probes (for example a probe including SEQ ID NO: 17), one or more N5 subtype-specific detection probes (for example a probe including SEQ ID NO: 26 or 27), one or more N6 subtype-specific detection probes (for example a probe including SEQ ID NO: 32 or 33), one or more N7 subtype-specific detection probes (for example a probe including SEQ ID NO: 40-43), one or more N8 subtype-specific detection probes (for example a probe including SEQ ID NO: 46), one or more N9 subtype-specific detection probes (for example a probe including SEQ ID NO: 51), one or more H1 subtype-specific detection probes (for example a probe including SEQ ID NO: 58 or 59), one or more H2 subtype-specific detection probes (for example a probe including SEQ ID NO: 62 or 63), one or more H3 subtype-specific detection probes (for example a probe including SEQ ID NO: 67 or 68), one or more H4 subtype-specific detection probes (for example a probe including SEQ ID NO: 72 or 73), one or more H5 subtype-specific detection probes (for example a probe including SEQ ID NO: 86-89 or 160), one or more H6 subtype-specific detection probes (for example a probe including SEQ ID NO: 94), one or more H7 subtype-specific detection probes (for example a probe including SEQ ID NO: 99 or 100), one or more H8 subtype-specific detection probes (for example a probe including SEQ ID NO: 103), one or more H9 subtype-specific detection probes (for example a probe including SEQ ID NO: 108-110), one or more H10 subtype-specific detection probes (for example a probe including SEQ ID NO: 113-115), one or more H11 subtype-specific detection probes (for example a probe including SEQ ID NO: 119), one or more H12 subtype-specific detection probes (for example a probe including SEQ ID NO: 122), one or more H13 subtype-specific detection probes (for example a probe including SEQ ID NO: 126-128), one or more H14 subtype-specific detection probes (for example a probe including SEQ ID NO: 131), one or more H15 subtype-specific detection probes (for example a probe including SEQ ID NO: 134), and/or one or more H16 subtype-specific detection probes (for example a probe including SEQ ID NO: 138-140). In some examples, the kit also includes one or more influenza A virus-specific detection probes (for example, one or more probes including SEQ ID NO: 143 or 146), one or more Newcastle virus-specific detection probes (for example, a probe including SEQ ID NO: 151), and/or a β-actin-specific detection probe (for example, a probe including SEQ ID NO: 154).

In certain embodiments the kit includes a set of primers, such as a pair of primers, capable of hybridizing to and amplifying an enriched influenza virus nucleic acid. Such a set of primers comprises at least one forward primer and at least one reverse primer, where the primers are specific for the amplification of an influenza subtype nucleic acid. In some examples, the set of primers includes primers including or consisting of the sequences of SEQ ID NOs: 157 and 158.

The amount of probe(s) and/or primer(s) supplied in the kit can be any appropriate amount, and may depend on the target market to which the product is directed. For instance, if the kit is adapted for research or clinical use, the amount of each nucleic acid primer provided would likely be an amount sufficient to carry out several reactions for detecting a target nucleic acid. General guidelines for determining appropriate amounts may be found in Innis et al., Sambrook et al., and Ausubel et al.

In some examples, the kits may also include materials for obtaining, collecting, or storing a sample, such as swabs, lancets, needles, syringes, microscope slides, blood collection tubes, and the like.

EXAMPLES

The following examples are provided to illustrate certain particular features and/or embodiments. These examples should not be construed to limit the disclosure to the particular features or embodiments described.

Example 1

Materials and Methods

Virus isolation and determination of 50% egg infectious dose ($EID_{50}$): Four influenza A virus isolates: H5N1 (A/poultry/Bangladesh/91392/2013) isolated from poultry in Bangladesh in 2013, H6N5 (A/wigeon/Italy/6127-23/2007) isolated from a wigeon in Italy in 2007, H10N7 (A/duck/Vietnam/NCVD-0100/2012) isolated from a duck in Vietnam in 2012, and H7N9 (A/Anhui/01/2013) isolated from a patient in China in 2013 were grown in embryonated chicken eggs and their $EID_{50}$ was determined following the Reed and Muench method (Muench, Am. J. Hygiene 27:3, 1938). HA and NA sequences were submitted to the Global Initiative on Sharing All Influenza Data (GISAID) database (available on the World Wide Web at platform.gisaid.org) with the following accession numbers EPI_ISL_221822 (A/poultry/Bangladesh/91392/2013), EPI_ISL_221823 (A/duck/Vietnam/NCVD-0100/2012), EPI_ISL_221824 (A/wigeon/Italy/6127-23/2007), and EPI_ISL_159416 (A/Anhui/01/2013).

Database inquiry and primer/probe design: Four different HA- and NA-subtypes of influenza A viruses (H5, N5, N7, and N9) were chosen and their HA and NA gene sequences were previously generated to confirm their subtype. Database mining included influenza A viruses from animal hosts and environmental samples collected globally from all geographic regions in the past 10 years, excluding genetically manipulated laboratory-derived strains. After removing low quality, incomplete, redundant, and misclassified sequences, the total number of sequences remaining for probe design was 450 (N5), 543 (N7), 908 (N9), 3983 (H5), and 6965 (M gene of influenza A) (Table 1). All influenza A viruses were from animal (non-human) hosts and environmental samples (excluding laboratory-derived strains) and were from all continents. The relatively conserved internal M gene was selected as a positive control for all subtypes of influenza A viruses. The HA or NA sequences of each subtype were aligned using the MAFFT program (MAFFT V7.017). An HA or NA phylogenetic tree was then built from these aligned sequences using Neighbor-Joining methods in the Geneious program (Geneious 8.1.6, Biomatters Ltd). Sequences with the closest genetic distances on a phylogenetic tree were extracted and re-aligned to form different clusters of sequences for probe design.

TABLE 1

Database search for sequences of animal influenza A viruses for probe design

| | Subtype | Gene | Date of sample collection | # of sequences in the database[a] | Quality QC1[b] | Quality QC2[c] | Quality QC3[d] | Quality QC4[e] |
|---|---|---|---|---|---|---|---|---|
| 1 | HxN1 | N1 | Jan. 1, 2004-Jul. 2, 2014 | 7,626 | 7592 | 6429 | 5201 | 5201 |
| 2 | HxN2 | N2 | Jan. 1, 2004-Jul. 2, 2014 | 6,343 | 6309 | 5670 | 4803 | 4800 |
| 3 | HxN3 | N3 | Jan. 1, 2004-Jul. 2, 2014 | 775 | 770 | 710 | 556 | 556 |
| 4 | HxN4 | N4 | Jan. 1, 2004-Jul. 2, 2014 | 499 | 497 | 412 | 332 | 331 |
| 5 | HxN5 | N5 | Jan. 1, 2004-Jul. 2, 2014 | 608 | 603 | 524 | 451 | 450 |
| 6 | HxN6 | N6 | Jan. 1, 2004-Jul. 2, 2014 | 1,632 | 1623 | 1534 | 1158 | 1154 |
| 7 | HxN7 | N7 | Jan. 1, 2004-Jul. 2, 2014 | 1,239 | 1211 | 864 | 545 | 543 |

TABLE 1-continued

Database search for sequences of animal influenza A viruses for probe design

| | Subtype | Gene | Date of sample collection | # of sequences in the database[a] | Quality QC1[b] | Quality QC2[c] | Quality QC3[d] | Quality QC4[e] |
|---|---|---|---|---|---|---|---|---|
| 8 | HxN8 | N8 | Jan. 1, 2004-Jul. 2, 2014 | 1,470 | 1467 | 1405 | 1070 | 1066 |
| 9 | HxN9 | N9 | Jan. 1, 2004-Jul. 2, 2014 | 1,330 | 1315 | 1201 | 909 | 908 |
| 1 | H1Nx | H1 | Jan. 1, 2004-Jan. 2, 2015 | 7,812 | 7694 | 3309 | 2806 | 2805 |
| 2 | H2Nx | H2 | Jan. 1, 2004-Jan. 2, 2015 | 711 | 708 | 576 | 506 | 506 |
| 3 | H3Nx | H3 | Jan. 1, 2004-Jan. 2, 2015 | 3,496 | 3481 | 2435 | 1917 | 1916 |
| 4 | H4Nx | H4 | Jan. 1, 2004-Jan. 2, 2015 | 1,262 | 1253 | 963 | 672 | 669 |
| 5 | H5Nx | H5 | Jan. 1, 2004-Jul. 2, 2014 | 6,661 | 6660 | 6621 | 3984 | 3983 |
| 6 | H6Nx | H6 | Jan. 1, 2004-Jan. 2, 2015 | 1,117 | 1111 | 818 | 726 | 723 |
| 7 | H7Nx | H7 | Jan. 1, 2004-Jan. 2, 2015 | 2,850 | 2830 | 2326 | 1742 | 1741 |
| 8 | H8Nx | H8 | Jan. 1, 2004-Jan. 2, 2015 | 252 | 249 | 203 | 198 | 198 |
| 9 | H9Nx | H9 | Jan. 1, 2004-Jan. 2, 2015 | 2,537 | 2531 | 1126 | 1032 | 1031 |
| 10 | H10Nx | H10 | Jan. 1, 2004-Jan. 2, 2015 | 1,291 | 1277 | 963 | 667 | 667 |
| 11 | H11Nx | H11 | Jan. 1, 2004-Jan. 2, 2015 | 1,069 | 1059 | 963 | 828 | 828 |
| 12 | H12Nx | H12 | Jan. 1, 2004-Jan. 2, 2015 | 512 | 505 | 357 | 232 | 232 |
| 13 | H13Nx | H13 | Jan. 1, 2004-Jan. 2, 2015 | 260 | 254 | 153 | 139 | 139 |
| 14 | H14Nx | H14 | Jan. 1, 2004-Jan. 2, 2015 | 30 | 29 | 24 | 21 | 12 |
| 15 | H15Nx | H15 | Jan. 1, 2004-Jan. 2, 2015 | 17 | 15 | 12 | 9 | 9 |
| 16 | H16Nx | H16 | Jan. 1, 2004-Jan. 2, 2015 | 106 | 105 | 76 | 70 | 70 |
| | Influenza A | M | Jan. 1, 2004-May 15, 2014 | 12,265 | 12,229 | 9,162 | 6,965 | 6,965 |

[a] The sequences were downloaded from the Database of Influenza Viruses @CDC (DISC) and GISAID. All but genetically manipulated zoonotic influenza A viruses were excluded from the analysis.
[b] The sequences containing more than two ambiguous nucleotides were removed from analysis.
[c] All sequences less than 95% of full length open reading frame were removed.
[d] Duplicate entries with identical sequences were removed.
[e] Misclassification of influenza A subtype was identified using phylogenetic and BLAST analysis. All incorrect subtypes were excluded from analysis.

Three categories of probes were designed for each subtype; hybridization probe (HP), bridge probe (BP), and TaqMan probe (TMP). TMPs were selected from relatively conserved but subtype-specific regions. Once each TMP was finalized, HP and BP were selected around the TMP without overlapping with TMP to ensure specificity. All probes were searched against the National Center for Biotechnology Information (NCBI) database using the blastn program to exclude any non-target matches. The sequences of the probes are listed in Table 2. Probes were synthesized by Integrated DNA Technologies (Coralville, IA) unless otherwise indicated.

TABLE 2

Probe sequences for influenza A virus subtypes

| Subtype | Probe | Sequence (5'-3') | SEQ ID NO: |
|---|---|---|---|
| N1 | HP-1 | TTTTTGAAHMARYTACTTGTCRATRGTRAATGGCA | 1 |
| | HP-2 | AAYYAYTTGTCAAYGKYRAATGGCARCTCAGCACC | 2 |
| | BP-1 | CCACAAAARGAAATGMTRCTYCCACTDGTCCARAT | 3 |
| | BP-2 | ACAGTGTCACTRTYTACMCCACARAARGATATRCT | 4 |
| | BP-3 | CCACAGAARGARATRCTGCTTCCGCTAGCCCAGAT | 5 |

TABLE 2-continued

Probe sequences for influenza A virus subtypes

| Subtype | Probe | Sequence (5'-3') | SEQ ID NO: |
|---|---|---|---|
| | TMP-1 | CCGTCTGGCCADGACCA[5] | 6 |
| N2 | HP-1 | AAAATTGCGAAAGCTTATAYAGGCATRARRYYRAT | 7 |
| | BP-1 | GTCCACCAYACYCTRGYYTCYTKYGGYCTYCCTCT | 8 |
| | BP-2 | CCYGARGTRCCACAAAAYACRACAATACTGTTYGA | 9 |
| | TMP-1 | CCATCAGGCCATGAGCCTGTTCCATA | 10 |
| | TMP-2 | CCCCATCAGGCCATGAGCCTGA | 11 |
| N3 | HP-1 | TRTTACTTGGGCATAAACCCAATRTTRGMACCATC | 12 |
| | BP-1 | CCACAGAADGTRACTATACTRTTRCTKGTCCAAGA | 13 |
| | TMP-1 | CCCGATCCAGGTTCATTGTCTAGYCC | 14 |
| N4 | HP-1 | TACTTGTCTATGTCAAARGGCARBAGAGCGCCATC | 15 |
| | BP-1 | CTACCGCTAGTCCATATGGTYTTYTCYTTRGGCTG | 16 |
| | TMP-1 | CCAACYTGTGGTATCAGAATYAACACCACARA | 17 |
| N5 | HP-1 | CTACTAGARGTCCAAATGCTTGTCCTCTCTTCTGG | 18 |
| | HP-1-2 | CTACTWGAVGTCCAAATGCTYGTCCTCTCTTCTGG | 19 |
| | HP-2 | CATCTTATCGATGTCRAAKGGTAGAATTGCTCCAT | 20 |
| | HP-2-2 | CATCTTATCGATGTCRRAKGGTAGAATTGCTCCAT | 21 |
| | BP-1 | AACATGGAACTAAGCAYTGTTTAYYAGTCATTGTG | 22 |
| | BP-1-2 | AGTCATTGTDRYYGGRAYGGTGAAAGCTCCRCTGTA | 23 |
| | BP-2 | CAAAACACAGTGGARCTACTYGARGTCCAAATGCT | 24 |
| | BP-2-2 | GGGACCTYACTRRAAACACCACARAMACAGTGGA | 25 |
| | TMP-1 | Cy5-CCTCTTATCATTTCCARCCAGAAACATGGA-3IAbRQSp | 26 |
| | TMP-2 | Cy5-CTGGGACCTCACTGGAAACACCACAAAAC-3IAbRQSp | 27 |
| N6 | HP-1 | TACTTRAAGTAGATGATTTCAGCCCCATCATGCCA | 28 |
| | HP-2 | CTACTTAAAGTAGATGATYTCWGCMCCATCRTGCC | 29 |
| | BP-1 | ATRCTATTGGAYGTCCAMARTACACTACTYTCTTT | 30 |
| | BP-2 | CTCCCYCTRATYARYTCYACATARAAACAAGGATT | 31 |
| | TMP-1 | CCAAGATCCCAATCGCTCCTTGGATC[5] | 32 |
| | TMP-2 | CACCATCRTGCCAGGACCATGATCC | 33 |
| N7 | HP-1 | AWTTTACGAAAAGTATTGRATYTGTGCCCCATCGG | 34 |
| | BP-1 | CTCGTCCACCAAACATACTTGGCTTCTTCHGGYCT | 35 |
| | BP-1-2 | CTTCCTCTTATYARTTCAACATARAAACAGGGRTT | 36 |
| | BP-2 | CATACGTATTTAGCCTCTTCGGGTCTTCCTCTAAT | 37 |
| | BP-2-2 | ACTRTTACTYGYCCACCABACRTAYTTRGCCTCTT | 38 |
| | BP-3 | CCACATAGGGCAATTARACTRTTACTTGTCCACCA | 39 |
| | TMP-1 | HEX-CATAGTGC"A"ACTAAACTGTTRCTCGTCCACC-3IAbRQSp | 40 |
| | TMP-2 | HEX-CTTCCACA"T"AGGGCAATTAGACTGTTRCTTG-3IAbRQSp | 41 |
| | TMP-3 | HEX-CCGGACCCAACTGGGAATGGG-3IAbRQSp | 42 |
| | TMP-3-2 | AACCGGACCCAACTGGGAATGGG | 43 |

TABLE 2-continued

Probe sequences for influenza A virus subtypes

| Subtype | Probe | Sequence (5'-3') | SEQ ID NO: |
|---|---|---|---|
| N8 | HP-1 | ATCTTRTCGATGTCAAARGGAAGAATWGCTCCATC | 44 |
|  | BP-1 | ATGGAGCTRCTDGARGTCCAKATHGTYKTYTCTTC | 45 |
|  | TMP-1 | C + TCC + AC +A C + ATY + AC + AA + TGG[6] | 46 |
| N9 | HP-1 | TCTTAGAGGAAGTACTCTATTTTAGCCCCATCAGG | 47 |
|  | HP-1-2 | TCTTAGAGGAAGTACTCTATTTYAGCMCCATCWGG | 48 |
|  | BP-1 | AATTCTGTRCTGGAACACATYGATACTATRCTATT | 49 |
|  | BP-1-2 | CTGGTCCACCAYACTTTRTCCTCYTTRGGYCTYCC | 50 |
|  | TMP-1 | TEX-CCAGTTCCATTGTCCMAGGAATTCTGTRC-3IAbRQSp | 51 |
| H1 | HP-1 | TAAATGCATAYTCTGCATTGYARYGAYCCATTAGA | 52 |
|  | HP-2 | TCTYAGATRCATATTCTRCAYTGYAAAGACCCATT | 53 |
|  | HP-3 | ATACATATTCTRCAYTGTARMGAMCCATTRGAGCA | 54 |
|  | BP-1 | AGGGAGACTAAYARDACYAGGGAACTGGCGACTGT | 55 |
|  | BP-2 | GCCCCCAGGGAGACYARRARAACYARDGAACTGGC | 56 |
|  | BP-3 | CCYAGAGAGACTAVYAGTACYRRHGAGCTGGCGAC | 57 |
|  | TMP-1 | CACATCCAGAAACTGAYTGCCCCAG | 58 |
|  | TMP-2 | CACATCCAGAARCTGATTGCCCCAG | 59 |
| H2 | HP-1 | ATYCTGCAYTGCAGAGAYCCRTTRGARCACATCCA | 60 |
|  | BP-1 | ATGATTGCCARTGACARGGARCCTGCHACTGTAGC | 61 |
|  | TMP-1 | TCCCAGCTATCATGATTGCCAGTGACA | 62 |
|  | TMP-2 | CCAGCCATCATGATTGCCAGTGACA | 63 |
| H3 | HP-1 | AATGCAAATGTTGCAYCTRATGTTGCCYTYYTGGC | 64 |
|  | BP-1 | TGGCAAAGGARATCCAYARGATCCARTCYTTGTATCC | 65 |
|  | BP-2 | TTGTTTAWTGCTTCATCYCTGTATAYGTMATGGTCA | 66 |
|  | TMP-1 | CCCACATAATRAAACCAATAGAACAACGC | 67 |
|  | TMP-2 | CAAAGCAARAAGCATGATATGGCAAGGA | 68 |
| H4 | HP-1 | AAATRCAAATCTGRCACCKGAKGTTTCCRTTYTGA | 69 |
|  | BP-1 | AGTGCAACGARYAARAAGCATGATATGAAAAGGA | 70 |
|  | BP-2 | TCCAAAGRATRRTGTCYTTGTAYCCCTGGGTCAAT | 71 |
|  | TMP-1 | CACCGGATGTTTCCRTTCTGACAAGCCC | 72 |
|  | TMP-2 | CAAAAAGCATGAYATGGAGAATGAAATCCA | 73 |
| H5 | HP-1 | ACCTTRTCRTARAGGTTCYTDACATTTGAGTCATG | 74 |
|  | HP-1-2 | ACCTTDTCRTARAGRTTCYTDACATTTGAGTCATG | 75 |
|  | HP-2 | TAGATGCAAATTCTGCACTGCAATGAYCCATTRGA | 76 |
|  | HP-2-2 | TAGATGCAAAYYCTGCACTGCAATGAYCCATTRGA | 77 |
|  | HP-3 | ACTCCATTTAGRCTGCAKAGCTTYCRTTGTGTGC | 78 |
|  | HP-3-2 | ACTCCATTTAGRCYGCAKAGCTTYCRTTGTGTGY | 79 |
|  | BP-1 | ACCAGAAGTTCAGCATTATAAGTCCARACATCTAG | 80 |
|  | BP-1-2 | ACYARRAGTTCWGCRTTATAAGTCCARACATCTAG | 81 |
|  | BP-2 | CCAGCTAYCATGATTGCCAGTGCTAGGGAACTCGC | 82 |

TABLE 2-continued

Probe sequences for influenza A virus subtypes

| Subtype | Probe | Sequence (5'-3') | SEQ ID NO: |
|---|---|---|---|
| | BP-2-2 | CCAGCYAYCATGATTGCCAGTRCTARGGAACTCRC | 83 |
| | BP-3 | TCTGTCGAGTTGTTTGCATGGTAACCAATGCAAAT | 84 |
| | BP-3-2 | GTCGAGTTRTTTGCATGGTAACCAATGCAAATYTG | 85 |
| | BP3-3 | GTCGAGTTRTTTGCATGRTAACCAATGCAAATYTG | 159 |
| | TMP-1 | FAM-CTCTCATTTTCCATGAGAACC-BHQ1[1] | 86 |
| | TMP-1-2 | TAGAGTTCTCTCATTTTCCATGAGAACYARAAGTTCAGC | 87 |
| | TMP-2 | FAM-CATCCAAA"A"RGATAGACCAGCTAYCATGATTG-3IAbRQSp[2] | 88 |
| | TMP-3 | FAM-CAGTRACA"T"TCTTTTCCATTATTGTGTCAACCTG-3IAbRQSp | 89 |
| | TMP-3-1 | CAGTRACATTCTTTTCCATTATYGTGTCAACCTG | 160 |
| H6 | HP-1 | CAYTGCATTGAACYATTTGAACACATCCAAAGACC | 90 |
| | HP-2 | ATYCTGCAYTGCATTGARCYATTYGARCACATCCA | 91 |
| | BP-1 | GTACTATAAATGGCAAGDATTTGATACACRYCAAA | 92 |
| | BP-2 | CTATAAATRGCAAGRATYTGATAYACACCRAGRTT | 93 |
| | TMP-1 | CTGCTCGATAYCGTACTAT | 94 |
| H7 | HP-1 | TATATACAAATAGTGCACYGCATGTTTCCATTCTT | 95 |
| | HP-2 | TTCAYRCAYATGAARRYAAGGCCCATTRCAATGGC | 96 |
| | BP-1 | GATTATGTCYTTGTATCCACTACTCAAYTTCACTG | 97 |
| | BP-2 | AGTATYAYMTCTTTRTARCCRCTGCTYARTTTGAC | 98 |
| | TMP-1 | CATGATGCCCCGAAGCTAAACCATAAGATT | 99 |
| | TMP-2 | CATGATGCCCCGAAGCTAAACCAAAGTATC | 100 |
| H8 | HP-1 | AATACAGAACATGCATCTACAAGATCCATTYTGCA | 101 |
| | BP-1 | GACTGGCCGCCACYGTACTGTARATGCTRAGAATT | 102 |
| | TMP-1 | ACCTCCAGCAATCAGGATTGCCAAGCA | 103 |
| H9 | HP-1 | ATGTTGCRYCTGCAHGAHCCATTDGACATRGCCCAGA | 104 |
| | HP-2 | TCATTTGAATGCTGRAAHCCRTACCAGCCWGCAAC | 105 |
| | BP-1 | CCHTCAGAYTCCAGYTTDAYYCCYTCTATTTTCTG | 106 |
| | BP-2 | CAWCCBCCYTCTATRAAYCCAGCTATRGCACCAAA | 107 |
| | TMP-1 | ATCCTCACCATTTATTCGACTGTCGCCTCA | 108 |
| | TMP-2 | CTTGCRATGGGGTTTGCTGCCTTC | 109 |
| | TMP-3 | ATAGCTGGATTCATAGAAGGAGGTTGGCCWGG | 110 |
| H10 | HP-1 | TAAATRCAGATTGTGCATCGCATGTTYCCATTYYTCA | 111 |
| | BP-1 | GCCCCGAAGCTAAACCAVARKATDAYRTCYTTRTA | 112 |
| | TMP-1 | ACAAGYCCCATGATGACAGCCAAAAG | 113 |
| | TMP-2 | CAAGACCCATGACAACGGCTAGAAGAACA | 114 |
| | TMP-3 | ACAAGACCCATWACAACGGCTAGAAGAACAAA | 115 |
| H11 | HP-1 | CAATTYTAAATGCAAATGKTACATCTRCATGAYCC | 116 |
| | BP-1 | AAATTGACAGTATTTTRTAVACRTTSCCRYTRGAA | 117 |
| | BP-2 | TCTARTYTCACYCCYTCRATYTCCTGRCGRTTGAT | 118 |

TABLE 2-continued

Probe sequences for influenza A virus subtypes

| Subtype | Probe | Sequence (5'-3') | SEQ ID NO: |
|---|---|---|---|
|  | TMP-1 | CTGTCRATTTACAGCTGCATTGCAAGCAGTCTC | 119 |
| H12 | HP-1 | ATACAGAAAGTACAACGAACATTTCCATTYTGACA | 120 |
|  | BP-1 | ACTAAGCTTGARGCAACRCTGCTGTAGATGCTCA | 121 |
|  | TMP-1 | CCGAAAATGAAACCCCCAATAATCATGAGC | 122 |
| H13 | HP-1 | ATACAAACATTGAATCGRCAGYTYCCAYTACTACA | 123 |
|  | HP-2 | ACTTATATACARATATTRAAHCGGCARYTKCCACT | 124 |
|  | BP-1 | ACTGCTTGCRATGCARCTGTAWATYGAYARTGCTT | 125 |
|  | TMP-1 | CAGGCCCACATRATGAAAGAGAGTATGAGTC | 126 |
|  | TMP-2 | ATTGAAYCGGCAATTGCCACTAYTACATG | 127 |
|  | TMP-3 | CATGYCCACATGATGAATGCAAGTATGAG | 128 |
| H14 | HP-1 | CAAGCCCAWAGAACAAATCCCARAATCAGTGCCAC[1] | 129 |
|  | BP-1 | TTGTTRATGGCYTCATCCCTRTAGATGTTGTGRTC | 130 |
|  | TMP-1 | ACAAAGCATGACATGGAGAAAGAAATCCACAG | 131 |
| H15 | HP-1 | CGCAGATTCCCGTTTTTCACACACATGAAAATAAG | 132 |
|  | BP-1 | TCCTGTCGATATTCAGTGTGATTGTAAGTRTTRTT | 133 |
|  | TMP-1 | CATGATGCCCCGAAGCTAAACCATAGTATYAC | 134 |
| H16 | HP-1 | TATATACAMACATTRAACCGGCAATTNCCAYTGCT | 135 |
|  | BP-1 | ATTGTCTTCAGTCTTCAAYTTKATCCCTTCRATTT | 136 |
|  | BP-2 | CTGCTTGCAATGCARCTATAAATTGMCAGKAYTTT | 137 |
|  | TMP-1 | TGAGTCCTACCAGAACAACACTGCTTGCA | 138 |
|  | TMP-2 | CATGCCCACATTATRAATGCAAGTATGAGACC | 139 |
|  | TMP-3 | TATGAGACCYACCATCACAA | 140 |
| InfA[3] (M) | HP-1 | CATTYCCATTDAGGGCATTYTGGACAAAVCGTCTA | 141 |
|  | BP-1 | CGCTCACTGGGCACGGTGAGCGTRAAYACAAAYCC | 142 |
|  | TMP-1 | FAM-CTACGCTGCAGTCCTCGCTCACTGG-3IAbRQSp | 143 |
| InfA (−) RNA (M) | HP-1 | GGGCATTYTGGAYAAANCGTCTACGCTGCAGTCC | 144 |
|  | BP-1 | TCACTGGGCACGGTGAGCGTRAAYACAAAHCCYAA | 145 |
|  | TMP-1[4] | CTACGCTGCAGTCCTCGCTCACTGG | 146 |
| InfA (+) RNA (M) | HP-1 | TTRGGDTTTGTRTTYACGCTCACCGTGCCCAGTGA | 147 |
|  | BP-1 | GGACTGCAGCGTAGACGNTTTRTCCARAATGCCCT | 148 |
| NDV | HP-1 | GAGTATYTTRGCAACYTGRGGAGAGGCATTTGCTA | 149 |
|  | BP-1 | GARGGYCCGAGYACATCACTGAGCCCRACRGATAG | 150 |
|  | TMP-1 | TCTCTAGCAGTGGGACAGCCTGCTATCC | 151 |
| Avian β-actin | HP-1 | CTGCTCRAAAYCCAGRGCRACRTAGCACAGCTTCT | 152 |
|  | BP-1 | TAGATGGGCACAGTGTGGGTAACRCCATCACCAGA | 153 |
|  | TMP-1 | CAGGTCACGGCCAGCCAGATCC | 154 |

*Nucleotides in quotes (e.g., "A") include a linked ZEN quencher
[1]Synthesized by Life Technologies (Carlsbad, CA) with a minor groove binding (MGB) molecule at 3'-end
[2]3IAbRQSp is 3' Iowa Black® RQ quencher
[3]InfA probes were designed against the consensus sequence of the matrix (M) gene of 6965 Influenza A viruses (Table 1)
[4]The same TMP is used for detection of (−) and (+) InfA RNA
[5]Synthesized as MGB probe
[6]Synthesized as LNA probe. "+" indicates the position of LNA. For example A+ means the nucleotide A is synthesized as a locked nucleic acid R = G or A; Y = T or C; Y = T + C; M = A or C; K = G or T; S = G or C; W = A or T; B = C or G or T; D = A or G or T; H = A or C or T; V = A or G or C; N = any nucleotide The HP and BP probes (Table 2) were synthesized as chimeras with an adapter as illustrated in FIG. 1. The sequence of the HP adapter was 5'-CGACCAG-GAAACAGCTATGACC-3' (SEQ ID NO: 155). HP was at the 3' end of the adapter and the 5' end of the adapter included an amine group (amino modifier C12, AmMC12) to mediate conjugation of the probe to magnetic beads (e.g., 5'-AmMC12-CGACCAGGAAACAGCTATGACC-HP).

The sequence of the BP adapter was 5'-TT-CACTGGCCGTCGTTTTACAAC-3' (SEQ ID NO: 156). BP was at the 5' end of the adapter and a 3' amino modifier (AmMO) was introduced to decrease potential digestion of probe by T4 DNA polymerase (e.g., 5'-BP-TT-CACTGGCCGTCGTTTTACAAC-AmMO-3'). The sequences of the universal adapter primers (UAP) used in this study were TGTTGTAAAACGACGGCCAGTGA ($UAP_F$; SEQ ID NO: 157) and CGACCAGGAAACGAC-TATGACC ($UAP_R$; SEQ ID NO: 158).

Probe conjugation: A suspension of 1.0 mL of Dynabeads® magnetic beads (Cat 65011, Thermo Fisher Scientific) was dispensed into a copolymer microcentrifuge tube (Cat BP-4202S, CP Lab Safety). The tube was placed in a magnet for 2 minutes and the supernatant was removed. The Dynabeads® were washed twice in 1 mL 100 mM MES buffer, pH4.5 (Cat M2933, Sigma-Aldrich), 10 minutes each round. The beads were re-suspended in 180 µL of the MES buffer. Sixty microliters of amine-substituted HPs (666.7 µM) were added into the beads and they were agitated on a HulaMixer® sample mixer (Cat 15920D, Life Technologies) at 20 rpm for 30 minutes. One hundred microliters of 10 mg/mL EDC (1-ethyl-3-[3-dimethylaminopropyl] carbodiimide hydrochloride) (Cat 77149, Thermo Scientific) was added into the beads and the agitation was continued for another 60 minutes. Then 300 µL of 0.04% Tween® 20 detergent was added to the beads and mixed well by vortexing. The beads were washed briefly in 1.0 mL 0.1% lithium dodecyl sulfate (Cat L9781, Sigma-Aldrich) and three times in 1 mL TT buffer (25 mM Tris buffer, pH 8.0, 0.01% Tween® 20). The coupled Dynabeads® were stored in 1 mL TT buffer at 4° C.

Quality control (QC) of probe conjugation: Two methods were used for QC of probe conjugation: (1) spectrophotometer QC method and (2) adapter-complementary probe QC method. In the spectrophotometer QC method, the amounts of free probe left in the supernatant before and after conjugation was measured in duplicate using a NanoDrop™ spectrophotometer (Cat ND-2000, Thermo Fisher Scientific). The A260 readings were then used to calculate the percentage of probes coupled onto the Dynabeads®. In the adapter-complementary probe QC method, a 3'-6-FAM probe complementary to the adapter sequence was annealed to the on-bead HPs (experimental set) or uncoupled beads (background control) at 42° C. for 30 minutes in 1× tetramethylammonium chloride (TMAC) hybridization solution (Wood WI 1985). Following a brief washing in WBB (10 mM Tris-HCl, pH8.0, 0.1M LiCl, 0.01% Tween® 20), the fluorescent signals from the adapter-complementary probes were collected on an Mx3005P thermocycler (Agilent Technologies). The relative fluorescence intensity of the experimental set over the background control was then used to evaluate the hybridization efficiency.

RNA extraction, cDNA generation, hybridization, and PCR template preparation: Viral RNA was extracted from allantoic fluid on a MagNA Pure® LC system using MagNA Pure® LC Total Nucleic Acid Isolation kit (Cat 03038505001, Roche Life Science). cDNA was generated from total RNA using random primer-based SuperScript® VILO™ cDNA synthesis kit (Cat 11755250, Thermo Fisher Scientific). RNase H digestion (Cat M0297L, New England BioLabs Inc) was performed following cDNA synthesis to remove RNA from DNA/RNA duplex. Hybridization was executed on a ThermoMixer® with a ThermoTop® heated lid (Cat 5382000023, Eppendorf) to prevent condensation and ensure constant reaction volume over extended time of incubation. Briefly, 5.0 µL of HP-coupled Dynabeads® were resuspended in 160 µL 1×TMAC hybridization buffer (Wood WI 1985) together with 10.0 µL cDNA and 2.0 µL 50 nM BP. The mixture was incubated on a thermomixer at 42° C. with constant agitation at 1,000 rpm for 30 min. Following incubation, the beads were washed briefly in 150 µL WBA (10 mM Tris-HCl, pH 8.0, 0.1 M LiCl, 0.01% Tween-20, 0.1% LDS) followed by a brief wash in WBB (10 mM Tris-HCl, pH 8.0, 0.1 M LiCl, 0.01% Tween-20). The beads were then suspended in 50 µL T4 DL/DP buffer (100 µM dNTP, 0.1 mg/mL BSA, 0.1% Tween-20, 1× T4 DNA ligase buffer) with 0.3 U T4 DNA polymerase (Cat M0203L, New England BioLabs Inc) and 200 U T4 DNA ligase (Cat M0202M, New England BioLabs Inc) and were incubated at room temperature (20° C.-25° C.) for 10 minutes. After a brief rinse with 100 µL $H_2O$, the beads were suspended in 50 µL 0.2 N NaOH and incubated at room temperature for 5 minutes followed by an immediate neutralization step using 50 µL NB (0.2 N HCL). The beads were then washed twice with 100 µL $H_2O$ and resuspended in 1×PicoMaxx® High Fidelity PCR mix (Cat #600424, Agilent Technologies) with 200 nM $UAP_F$/$UAP_R$. A brief PCR amplification was carried out at 95° C. 2 min for 1 cycle, 95° C. 40 sec, 60° C. 30 sec, followed by 72° C. 20 sec for 10 cycles. The resulting mixture was used as a template for subtyping influenza A virus using singleplex or multiplex TaqMan qPCR as illustrated in FIG. 1.

Singleplex and Multiplex AmASIV: In singleplex AmASIV, HPs, BPs and TMPs were specific for only one HA or NA subtype. The TMPs were labeled with different fluorophores representing different HA or NA subtypes (H5, FAM; N7, HEX; N9, TEX; N5, Cy5). The working TMP concentrations were titrated to maximize sensitivity. The FAM-H5_TMP, HEX-N7_TMP, TEX-N9_TMP, and Cy5-N5_TMP were used at 100 nM, 400 nM, 150 nM, and 75 nM, respectively. $UAP_F$ and $UAP_R$ were used at 400 nM. Singleplex reactions were prepared using 1× Brilliant® Multiplex QPCR Master (Cat 600553, Agilent Technologies). The PCR was carried out on a AriaMx real-time PCR thermocycler (PN G8830-6400, Agilent Technologies) at 95° C. 10 min for 1 cycle, 95° C. for 15 sec followed by 55° C. for 60 sec for 45 cycles.

In multiplex AmASIV, HPs, BPs and TMPs representing multiple HA and NA subtypes were combined into a single reaction. HPs specific for H5, N5, N7, and N9 were mixed and conjugated onto Dynabeads® magnetic beads. BPs specific for these four genes were combined and diluted into a working solution at a final concentration of 50 nM for each BP. The BP mixture together with the on-bead HPs were then hybridized to cDNA of individual subtypes of influenza A virus. TMPs specific for H5, N5, N7, and N9 were mixed together at the working concentration that was optimized in their singleplex assay. The remaining procedures and PCR amplification conditions remained the same as the singleplex AmASIV assay.

Evaluation of sensitivity and specificity of AmASIV assay: RNA was extracted from 100 µL of virus of each subtype listed in Table 1 and eluted into 100 µL RNase-free $H_2O$. Two microliters of RNA was diluted into 98 µL $H_2O$. The relative quantity of RNA was estimated by taking 5 µL diluted RNA as template for RT-PCR using the FDA-approved influenza A TaqMan qPCR assay following the recommended protocol (available on the World Wide Web at partner.cdc.gov/Sites/NCIRD/clsis/SitePages/default.aspx 2015). cDNA was synthesized from undiluted RNA as described above. Ten-fold serial dilutions of the cDNA were then used as input for the multiplex AmASIV assay. As a control, the same set of diluted cDNA was also quantified using the FDA-approved TaqMan qPCR assays. Limit of detection (LOD) of the AmASIV and the TaqMan qPCR assays were determined when at least two out of three reactions were positive and the $C_T$ value were less than or equal to 37. To minimize PCR signal variations, cDNA of each subtype was diluted to yield a $C_T$ value between 22 and 28. The cDNA was then used as template to assess the specificity of the AmASIV assay from three different perspectives: 1) determination if the multiplex TMPs detected any non-target subtypes; 2) influenza B cDNA was processed in parallel as a near neighbor non-target control; 3) no input control (NIC) was included to test if BP might ligate to HP to produce false positive results.

Example 2

Conjugation of Hybridization Probes to Magnetic Beads

Figure 2C:
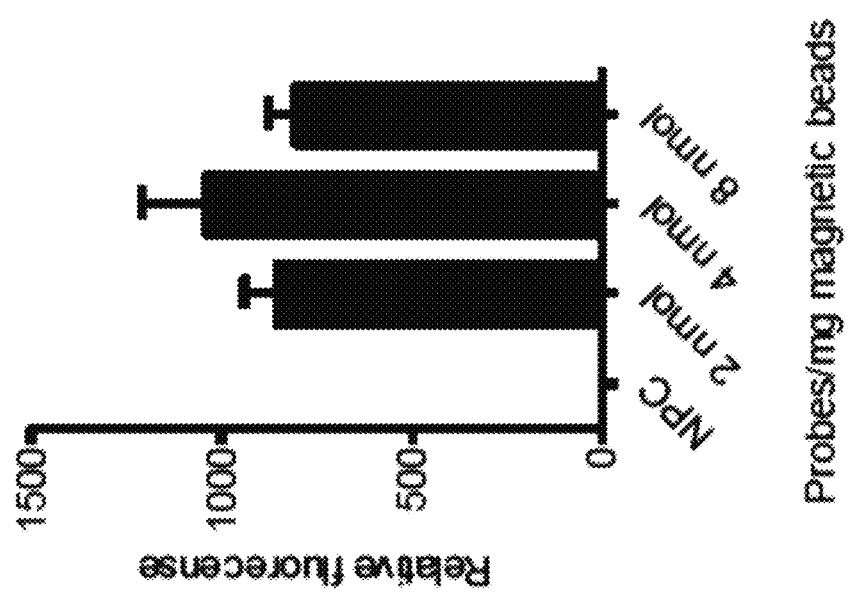
FIGS. 2A-2C are a series of graphs showing conjugation of the hybridization probes to magnetic beads.
Figure 2B:
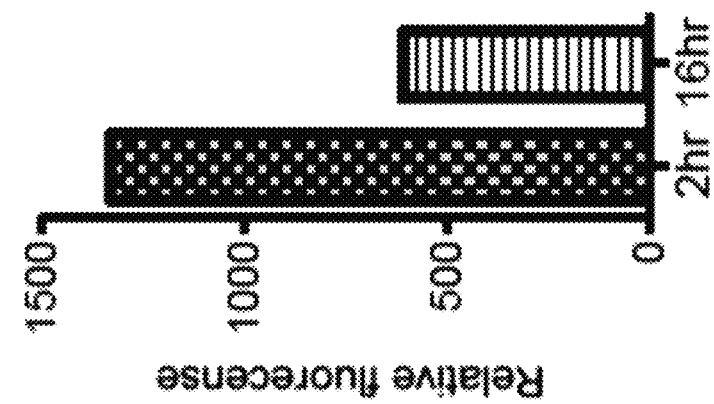
Figure 2A:
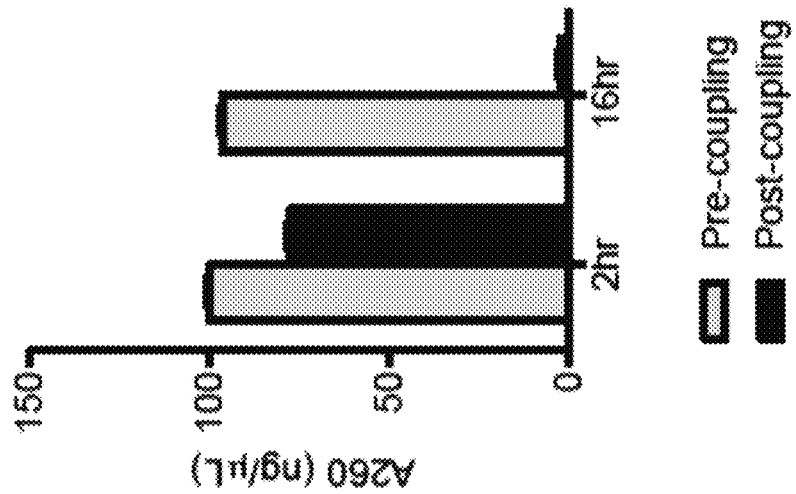

The first step of AmASIV test was to couple HPs to Dynabeads® magnetic beads (FIG. 1). Subsequently, the spectrophotometer QC method was used to determine that 23% of the input HPs were conjugated onto the Dynabeads® after 2 hours of coupling (FIG. 2A). This number increased to 97% by extending the incubation to 16 hours (FIG. 2A). Following HP-beads conjugation, the efficiency of probe-target hybridization was assessed using the adapter-complementary probe QC method. The relative strength of fluorescence of the experimental group over the background control was used to evaluate hybridization efficiency. There was more than a 50% drop in relative fluorescence after 16 hours conjugation as compared to 2 hours of conjugation (FIG. 2B). A series of conjugation times (30 min, 1 hour, and 2 hours) suggested that maximal hybridization efficiency was achieved after 1 hour. The binding capacity of the beads became saturated when HP concentration reached ~4 nmol per mg of beads under the specified conjugation condition (FIG. 2C). Further increasing the input of HPs to 8 nmol reduced the coupling efficiency (FIG. 2C).

Counterintuitively, extended incubation with EDC increased coupling efficiency, but reduced hybridization efficiency (FIGS. 2A and 2B). This could result from DNA damage caused by EDC, as EDC has been reported to chemically modify single-stranded DNA and may affect DNA-DNA hybridization (Vera Lund et al., *Nucl. Acids Res.* 16:10861-10880, 1988). Therefore, conditions for probe conjugation including duration of coupling reaction and the ratio of Dynabeads® to HPs were optimized to maximize probe coupling efficiency while minimizing potential DNA damage caused by EDC.

Example 3

Figure 3A:
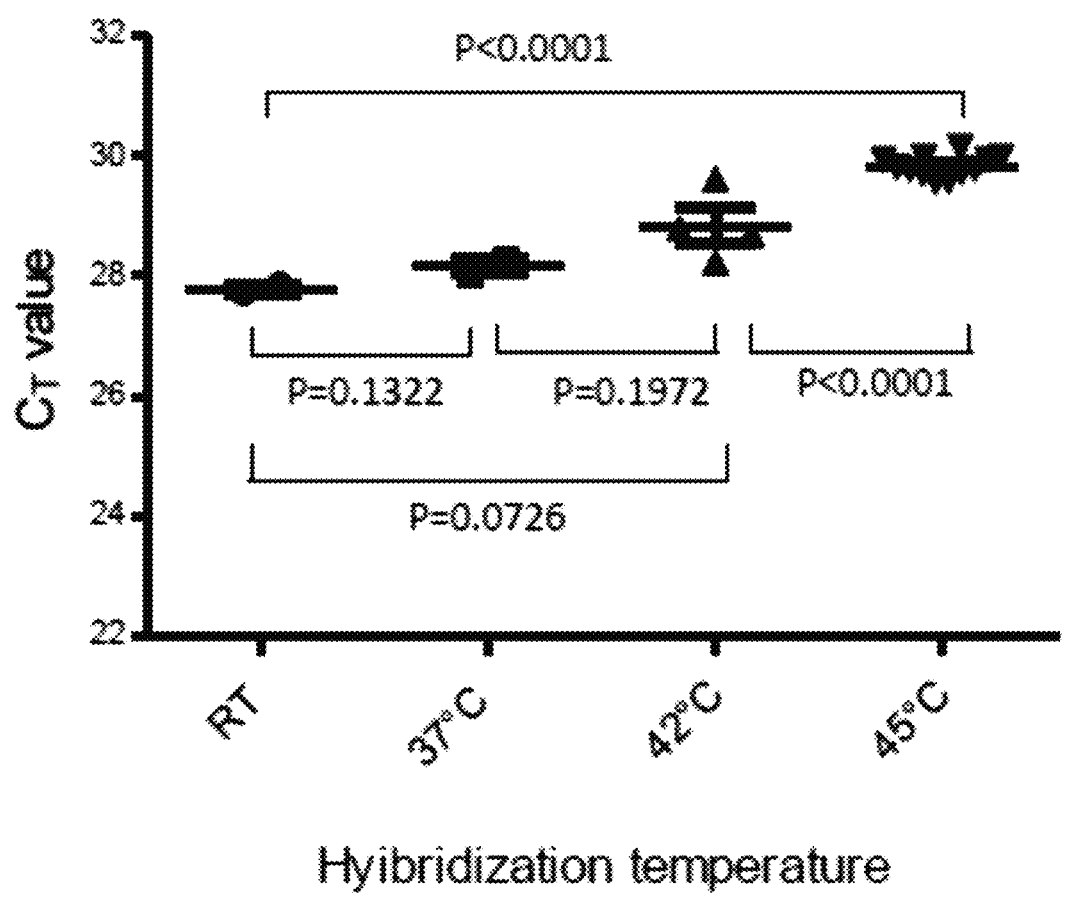
FIGS. 3A-3B are graphs showing effect of hybridization temperature on cDNA hybridization (FIG. 3A) and effect of duration of hybridization on target detection (FIG. 3B).
Figure 3B:
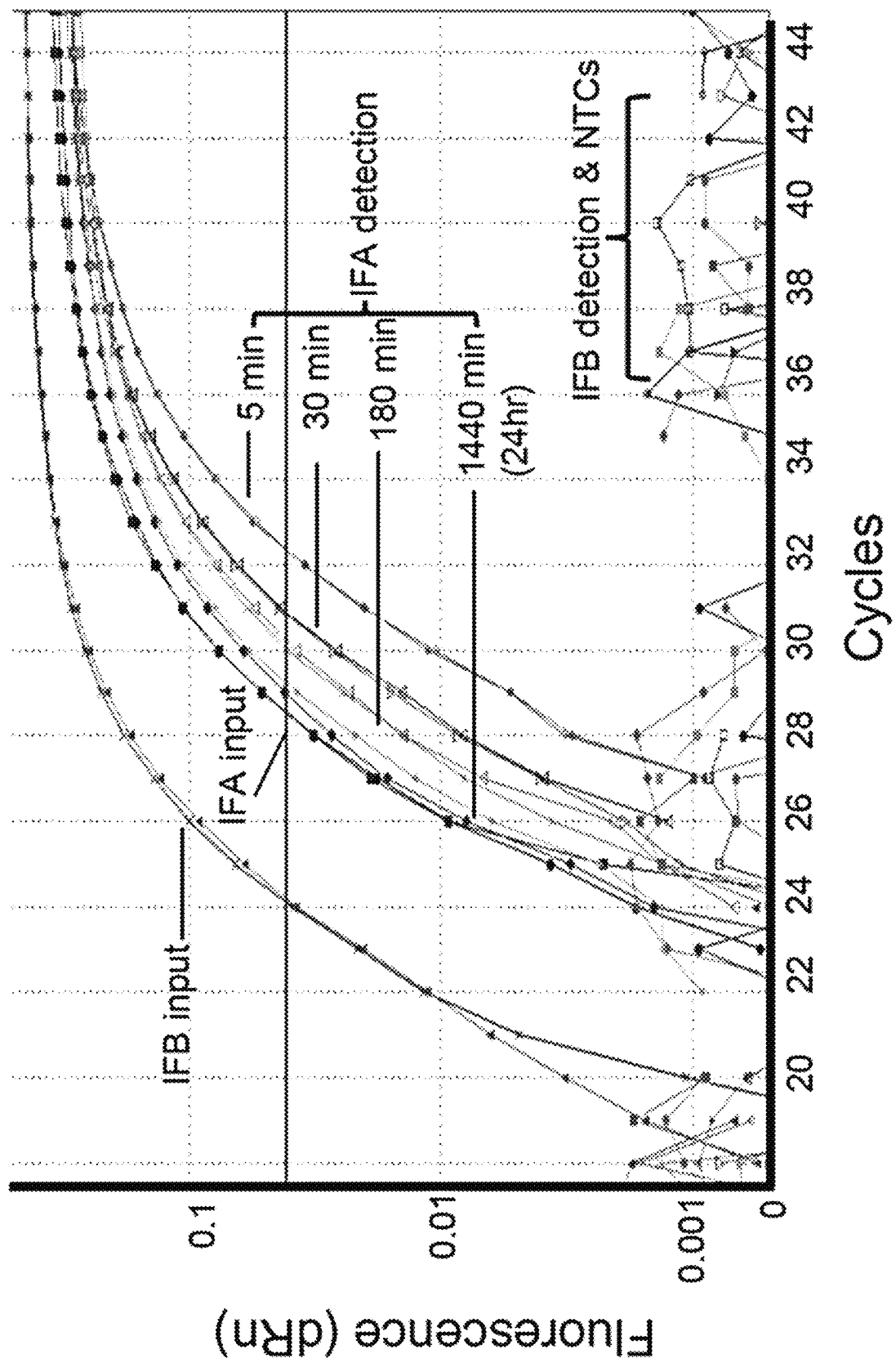

Hybridization of Influenza cDNA to Bead-Conjugated Hybridization Probes and Subtype Differentiation TaqMan qPCR in detection of influenza cDNA hybridized to HP exhibited no significant changes in $C_T$ value (changes of $C_T$<1, P≥0.07) across the temperatures tested, suggesting increasing hybridization temperature from room temperature (~22° C.) to 37° C. and further to 42° C. had no significant impact on cDNA-probe hybridization efficiency (FIG. 3A). Further increasing hybridization temperature to 45° C., however, reduced the hybridization efficiency significantly by about 50% as compared to the hybridization performed at room temperature (changes of $C_T$=2, P<0.0001) (FIG. 3A). After 5 minutes of hybridization, H5N1 cDNA captured on beads was detected by the influenza A TaqMan qPCR ($C_T$=32.5), but the $C_T$ value was 3.2 cycles higher than that ($C_T$=29.3) of the input H5N1 cDNA prior to hybridization (FIG. 3B). This difference translates to at least 10% of target detection, assuming up to 100% PCR amplification efficiency. Based on similar calculations, extended time of hybridization was able to detect ~30% (30 min), ~62% (180 min), or nearly 100% (24 hr) of the input cDNA (FIG. 3B). In contrast, ~30 fold more influenza B virus cDNA, which was used as a near neighbor non-target control, was not recognized after 24 hours, showing the specificity of the reaction (FIG. 3B).

Subtype differentiation was done through subtype-specific TaqMan probes that were labeled with different fluorophores representing different HA or NA subtypes (FIG. 4A). These fluorophores have distinct peak of emission wavelengths that are at least 30 nM away from each other to ensure specific signal collection from each subtype (FIG. 4A). The similar $C_T$ value of singleplex as compared to 4-plex AmASIV for each individual subtype indicate that the 4-plex AmASIV performed equally well to their corresponding singleplex assay (FIG. 4B). When different subtypes of viruses were mixed together to mimic co-infections, the multiplex AmASIV correctly identified all subtypes in the sample.

Example 4

Sensitivity and Specificity of AmASIV

The analytical sensitivity of multiplex AmASIV was assessed in two ways (Table 3). First, the LOD was determined in terms of $EID_{50}$ per reaction or copies of RNA per reaction; second, the analytical sensitivity of multiplex AmASIV test was compared to that of singleplex TaqMan real-time PCR assays that are commonly used as the gold standard assays for clinical diagnosis of influenza by the Centers for Disease Control and Prevention and U.S. state public health laboratories (available on the World Wide Web at partner.cdc.gov/Sites/NCIRD/clsis/SitePages/default.aspx 2015). The LOD of the multiplex AmASIV test showed differences depending on the subtype tested. For example, the LOD of N5 AmASIV assay was $10^2$ $EID_{50}$/reaction, which was equivalent to that of the influenza A TaqMan qPCR that was designed against the relatively conserved M gene (Table 3). The LOD of H5, N7, or N9 AmASIV assay, however, was about 1 log higher than the M-gene qPCR (Table 3). Nevertheless, LOD of the H5 AmASIV ($10^{-0.6}$) was the same as that of H5 subtype-specific singleplex TaqMan assay that was designed against highly variable hemagglutinin gene segments of diverse influenza A(H5) viruses (Table 3).

TABLE 3

Limit of detection of AmASIV for subtyping influenza A viruses

| Virus[a] | Passage[1] (Harvest Date) | $EID_{50}$/mL | Influenza A TaqMan qPCR[2] CT ± SD[3] | LOD $EID_{50}$/reaction (CT ± SD)[4] | | |
|---|---|---|---|---|---|---|
| | | | | AmASIV | Influenza A TaqMan qPCR[2] | Subtype-specific TaqMan qPCR |
| H5N1 | E2 (Aug. 1, 2013) | $10^{3.50}$ | 25.0 ± 0.1 | $10^{-0.6}$ (25.8 ± 0.3) | $10^{-1.6}$ (32.9 ± 0.1) | $10^{-0.6}$ (36.4 ± 0.3)[5] |
| H6N5 | EX/E1 (Mar. 11, 2010) | $10^{9.19}$ | 18.2 ± 0.1 | $10^{2}$ (26.9 ± 1.1) | $10^{2}$ (35.4 ± 0.3) | NA |
| H10N7 | E1 (Jun. 26, 2013) | $10^{5.81}$ | 19.7 ± 0.1 | $10^{-0.3}$ (24.1 ± 0.3) | $10^{-1.3}$ (35.9 ± 0.8) | NA |
| H7N9 | P3/E1/E1 (Jul. 3, 2013) | $10^{6.00}$ | 18.2 ± 0.1 | $10^{-0.5}$ (30.3 ± 0.6) | $10^{-1.5}$ (36.5 ± 1.1) | NA |

LOD = limit of detection;
NA = subtype-specific assay was not available
[a]Viruses: H5N1 - A/poultry/Bangladesh/91392/2013; H6N5 - A/wigeon/Italy/6127-23/2007; H10N7 - A/duck/Vietnam/NCVD-0100/2012; N7N9 - A/Anhui/01/2013
[1]Virus was propagated in eggs (E) or host unknown (P). Passage numbers are indicated; X = unknown passage number
[2]FDA-approved TaqMan qPCR assay designed against the matrix gene of influenza A virus
[3]The relative amount of RNA extracted from each subtype of virus was estimated using the RT-PCR method described in Example 1. The CT value and standard deviation (SD) were calculated from triplicate RT-PCR reactions
[4]The CT value and SD were calculated from triplicate TaqMan RT-PCR reactions
[5]The lowest LOD of the FDA-approved TaqMan qPCR assays (H5a and H5b) designed against hemagglutinin gene of influenza A(H5) virus.

H5 probes in the 4-plex mix, whereas the N5, N7, and N9 specific probes did not react with the H5 cDNA. Likewise, the N5, N7, and N9 viruses were also detected only by their corresponding probes. There was no non-specific reaction with the other HA and NA subtypes tested (Table 4). Further, when an equivalent amount of influenza B virus RNA was processed in parallel as a near neighbor non-target control, none of the probes interacted with the influenza B virus cDNA, and the negative and positive controls yielded the expected results (Table 4).

TABLE 4

Specificity of AmASIV assay in detection of influenza A virus

| | AmASIV TMP Mix (4-plex) | | | | Control | | | |
|---|---|---|---|---|---|---|---|---|
| | FAM | Cy5 | HEX | TEX | | | | |
| Virus[a] | (H5) | (N5) | (N7) | (N9) | InfB[1] | NIC[2] | NTC[3] | Input[4] |
| H5N1 | 26.5 ± 0.4 | — | — | — | — | — | — | 25.9 ± 0.2 |
| H6N5 | — | 27.8 ± 0.5 | — | — | — | — | — | 26.2 ± 0 |
| H10N7 | — | — | 26.0 ± 0.3 | — | — | — | — | 24.7 ± 0.2 |
| H7N9 | — | — | — | 27.8 ± 0.5 | — | — | — | 27.1 ± 0.4 |

[a]Viruses: H5N1 - A/poultry/Bangladesh/2013; H6N5 - A/wigeon/Italy/2007; H10N7 - A/duck/Vietnam/2012; N7N9 - A/Anhui/01/2013
[1]Influenza B cDNA (Ct 25 ± 0.4) was processed in parallel with the influenza A cDNA as a near neighbor non-target control
[2]No input control (NIC) used equivalent amount of water to replace influenza cDNA in the AmASIV protocol
[3]No template control (NTC) used water instead of template in real-time PCR reactions
[4]Input of influenza cDNA prior to the AmASIV procedure was estimated using the FDA-approved influenza A TaqMan qPCR designed against influenza A matrix gene Example 5

Sensitivity and Specificity of Additional AmASIV Assays

Additional HPs were coupled to Dynabeads® magnetic beads as described in Example 1. A set of multiplex AmASIV assays were carried out as shown in FIG. 5A to detect each HA (H1-H16) and NA (N1-N9) subtype. The sets were designed to detect HA or NA of different clades or groups, in order to increase assay specificity. The assay also included controls for mature (−) strand RNA of influenza virus, NDV, and avian beta-actin. The assay can optionally also include probes for positive strand InfA cRNA and mRNA (InfA(+) RNA) and a swine control to detect swine-origin samples.

Figure 6A:
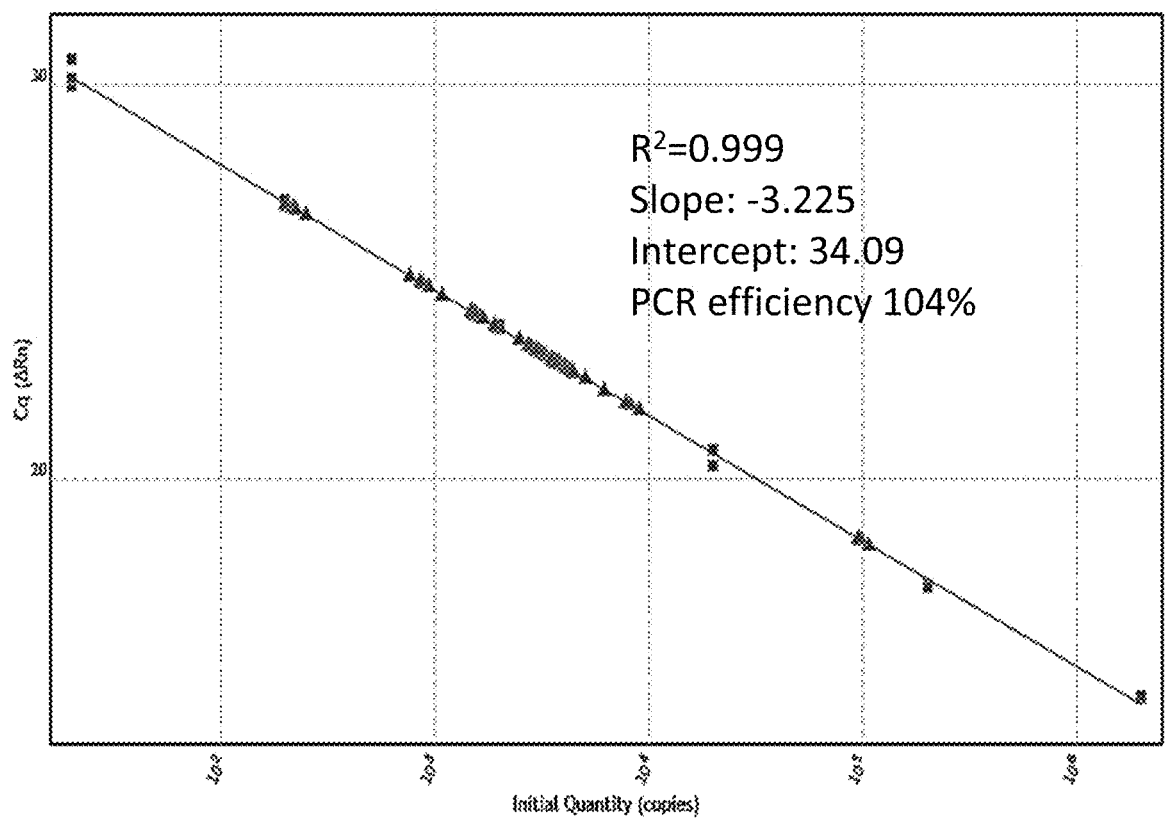
Figure 6B:
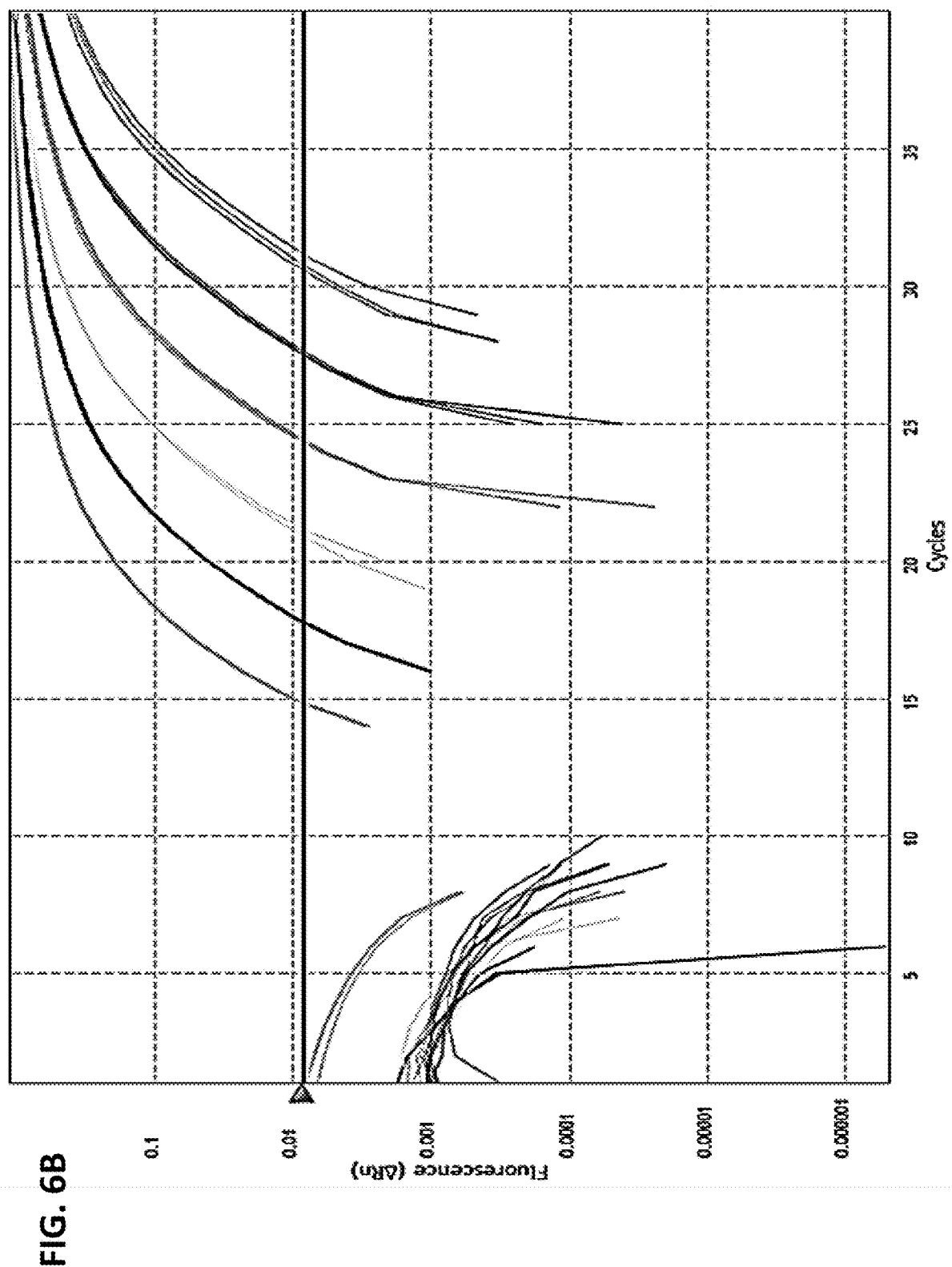

FIGS. 6A-6C are a series of panels showing RNA quantification of the indicated influenza A subtypes. FIGS. 6A and 6B are graphs showing quantification of the RNA of influenza A virus using standard curve analysis. RNA transcripts of the influenza A matrix gene were generated using in vitro RNA transcription. Six 10-fold serial dilutions of the transcripts were used as templates for TaqMan real-time RT-PCR (FIG. 6A). Standard curves were generated using copies of the transcripts against the Ct value from triplicate reactions per dilution of the transcripts (FIG. 6B). Influenza A virus isolates covering all HA (H1-H16) and NA (N1-N9) subtypes were quantified using standard curve analysis (FIGS. 6B and 6C).

The limit of detection (LOD) of the AmASIV assay is shown in FIG. 7A (for H1-H16) and FIG. 7B (for N1-N9). The LOD can be improved by titrating concentration of BP and TMP per reaction. Under optimal conditions, the sensitivity of the AmASIV assay is comparable to singleplex TaqMan real time RT-PCR (Table 3).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A kit comprising at least two probes, wherein the at least two probes comprise:

(a) a first probe comprising a first portion comprising a nucleic acid sequence at least 90% identical to any one of SEQ ID NOs: 1 or 2 and a second portion comprising SEQ ID NO: 155, and a second probe comprising a first portion comprising a nucleic acid sequence at least 90% identical to any one of SEQ ID NOs: 3-5 and a second portion comprising SEQ ID NO: 156;

(b) a first probe comprising a first portion comprising a nucleic acid sequence at least 90% identical to SEQ ID NO: 7 and a second portion comprising SEQ ID NO: 155, and a second probe comprising a first portion comprising a nucleic acid sequence at least 90% identical to any one of SEQ ID NOs: 8 or 9 and a second portion comprising SEQ ID NO: 156;

(c) a first probe comprising a first portion comprising a nucleic acid sequence at least 90% identical to SEQ ID NO: 12 and a second portion comprising SEQ ID NO: 155, and a second probe comprising a first portion comprising a nucleic acid sequence at least 90% identical to SEQ ID NO: 13 and a second portion comprising SEQ ID NO: 156;

(d) a first probe comprising a first portion comprising a nucleic acid sequence at least 90% identical to SEQ ID NO: 15 and a second portion comprising SEQ ID NO: 155, and a second probe comprising a first portion comprising a nucleic acid sequence at least 90% identical to SEQ ID NO: 16 and a second portion comprising SEQ ID NO: 156;

(e) a first probe comprising a first portion comprising a nucleic acid sequence at least 90% identical to any one of SEQ ID NOs: 18-21 and a second portion comprising SEQ ID NO: 155, and a second probe comprising a first portion comprising a nucleic acid sequence at least 90% identical to any one of SEQ ID NOs: 22-25 and a second portion comprising SEQ ID NO: 156;

(f) a first probe comprising a first portion comprising a nucleic acid sequence at least 90% identical to any one of SEQ ID NOs: 28 or 29 and a second portion comprising SEQ ID NO: 155, and a second probe comprising a first portion comprising a nucleic acid sequence at least 90% identical to any one of SEQ ID NOs: 30 or 31 and a second portion comprising SEQ ID NO: 156;

(g) a first probe comprising a first portion comprising a nucleic acid sequence at least 90% identical to SEQ ID NO: 34 and a second portion comprising SEQ ID NO: 155, and a second probe comprising a first portion comprising a nucleic acid sequence at least 90% identical to any one of SEQ ID NOs: 35-39 and a second portion comprising SEQ ID NO: 156;

(h) a first probe comprising a first portion comprising a nucleic acid sequence at least 90% identical to SEQ ID NO: 44 and a second portion comprising SEQ ID NO: 155, and a second probe comprising a first portion comprising a nucleic acid sequence at least 90% identical to SEQ ID NO: 45 and a second portion comprising SEQ ID NO: 156;

(i) a first probe comprising a first portion comprising a nucleic acid sequence at least 90% identical to any one of SEQ ID NOs: 47 or 48 and a second portion comprising SEQ ID NO: 155, and a second probe comprising a first portion comprising a nucleic acid sequence at least 90% identical to any one of SEQ ID NOs: 49 or 50 and a second portion comprising SEQ ID NO: 156;

(j) a first probe comprising a first portion comprising a nucleic acid sequence at least 90% identical to any one of SEQ ID NOs: 52-54 and a second portion comprising SEQ ID NO: 155, and a second probe comprising a first portion comprising a nucleic acid sequence at least 90% identical to any one of SEQ ID NOs: 55-57 and a second portion comprising SEQ ID NO: 156;

(k) a first probe comprising a first portion comprising a nucleic acid sequence at least 90% identical to SEQ ID NO: 60 and a second portion comprising SEQ ID NO: 155, and a second probe comprising a first portion comprising a nucleic acid sequence at least 90% identical to SEQ ID NO: 61 and a second portion comprising SEQ ID NO: 156;

(l) a first probe comprising a first portion comprising a nucleic acid sequence at least 90% identical to SEQ ID NO: 64 and a second portion comprising SEQ ID NO: 155, and a second probe comprising a first portion comprising a nucleic acid sequence at least 90% identical to any one of SEQ ID NOs: 65 or 66 and a second portion comprising SEQ ID NO: 156;

(m) a first probe comprising a first portion comprising a nucleic acid sequence at least 90% identical to SEQ ID NO: 69 and a second portion comprising SEQ ID NO: 155, and a second probe comprising a first portion comprising a nucleic acid sequence at least 90% identical to any one of SEQ ID NOs: 70 or 71 and a second portion comprising SEQ ID NO: 156;

(n) a first probe comprising a first portion comprising a nucleic acid sequence at least 90% identical to any one of SEQ ID NOs: 74-79 and a second portion comprising SEQ ID NO: 155, and a second probe comprising a first portion comprising a nucleic acid sequence at least 90% identical to any one of SEQ ID NOs: 80-85 or 159 and a second portion comprising SEQ ID NO: 156;

(o) a first probe comprising a first portion comprising a nucleic acid sequence at least 90% identical to any one of SEQ ID NOs: 90 or 91 and a second portion comprising SEQ ID NO: 155, and a second probe comprising a first portion comprising a nucleic acid sequence at least 90% identical to any one of SEQ ID NOs: 92 or 93 and a second portion comprising SEQ ID NO: 156;

(p) a first probe comprising a first portion comprising a nucleic acid sequence at least 90% identical to any one of SEQ ID NOs: 95 or 96 and a second portion comprising SEQ ID NO: 155, and a second probe comprising a first portion comprising a nucleic acid sequence at least 90% identical to any one of SEQ ID NOs: 97 or 98 and a second portion comprising SEQ ID NO: 156;

(q) a first probe comprising a first portion comprising a nucleic acid sequence at least 90% identical to SEQ ID NO: 101 and a second portion comprising SEQ ID NO: 155, and a second probe comprising a first portion comprising a nucleic acid sequence at least 90% identical to SEQ ID NO: 102 and a second portion comprising SEQ ID NO: 156;

(r) a first probe comprising a first portion comprising a nucleic acid sequence at least 90% identical to any one of SEQ ID NOs: 104 or 105 and a second portion comprising SEQ ID NO: 155, and a second probe comprising a first portion comprising a nucleic acid sequence at least 90% identical to any one of SEQ ID NOs: 106 or 107 and a second portion comprising SEQ ID NO: 156;

(s) a first probe comprising a first portion comprising a nucleic acid sequence at least 90% identical to SEQ ID NO: 111 and a second portion comprising SEQ ID NO: 155, and a second probe comprising a first portion comprising a nucleic acid sequence at least 90% identical to SEQ ID NO: 112 and a second portion comprising SEQ ID NO: 156;

(t) a first probe comprising a first portion comprising a nucleic acid sequence at least 90% identical to SEQ ID NO: 116 and a second portion comprising SEQ ID NO: 155, and a second probe comprising a first portion comprising a nucleic acid sequence at least 90% identical to any one of SEQ ID NOs: 117 or 118 and a second portion comprising SEQ ID NO: 156;

(u) a first probe comprising a first portion comprising a nucleic acid sequence at least 90% identical to SEQ ID NO: 120 and a second portion comprising SEQ ID NO: 155, and a second probe comprising a first portion comprising a nucleic acid sequence at least 90% identical to SEQ ID NO: 121 and a second portion comprising SEQ ID NO: 156;

(v) a first probe comprising a first portion comprising a nucleic acid sequence at least 90% identical to any one of SEQ ID NOs: 123 or 124 and a second portion comprising SEQ ID NO: 155, and a second probe comprising a first portion comprising a nucleic acid sequence at least 90% identical to SEQ ID NO: 125 and a second portion comprising SEQ ID NO: 156;

(w) a first probe comprising a first portion comprising a nucleic acid sequence at least 90% identical to SEQ ID NO: 129 and a second portion comprising SEQ ID NO: 155, and a second probe comprising a first portion comprising a nucleic acid sequence at least 90% identical to SEQ ID NO: 130 and a second portion comprising SEQ ID NO: 156;

(x) a first probe comprising a first portion comprising a nucleic acid sequence at least 90% identical to SEQ ID NO: 132 and a second portion comprising SEQ ID NO: 155, and a second probe comprising a first portion comprising a nucleic acid sequence at least 90% identical to SEQ ID NO: 133 and a second portion comprising SEQ ID NO: 156; and/or (y) a first probe comprising a first portion comprising a nucleic acid sequence at least 90% identical to SEQ ID NO: 135 and a second portion comprising SEQ ID NO: 155, and a second probe comprising a first portion comprising a nucleic acid sequence at least 90% identical to any one of SEQ ID NOs: 136 or 137 and a second portion comprising SEQ ID NO: 156.

2. The kit of claim 1, further comprising at least one probe comprising the nucleic acid sequence of any one of SEQ ID NOs: 6, 10, 11, 14, 17, 26, 27, 32, 33, 40-43, 46, 51, 58, 59, 62, 63, 67, 68, 72, 73, 86-89, 160, 94, 99, 100, 103, 108-110, 113-115, 119, 122, 126-128, 131, 134, 138-140, 143, 146, 151, or 154 and a detectable label.

3. The kit of claim 1, further comprising a pair of primers comprising the nucleic acid sequences of SEQ ID NOs: 157 and 158.

4. The kit of claim 1, further comprising at least one pair of control probes, comprising:

(a) a first probe comprising a first portion comprising a nucleic acid sequence at least 90% identical to SEQ ID NO: 141 and a second portion comprising SEQ ID NO: 155, and a second probe comprising a first portion comprising a nucleic acid sequence at least 90% identical to SEQ ID NO: 142 and a second portion comprising SEQ ID NO: 156;

(b) a first probe comprising a first portion comprising a nucleic acid sequence at least 90% identical to SEQ ID NO: 144 and a second portion comprising SEQ ID NO: 155, and a second probe comprising a first portion comprising a nucleic acid sequence at least 90% identical to SEQ ID NO: 145 and a second portion comprising SEQ ID NO: 156;

(c) a first probe comprising a first portion comprising a nucleic acid sequence at least 90% identical to SEQ ID NO: 147 and a second portion comprising SEQ ID NO: 155, and a second probe comprising a first portion comprising a nucleic acid sequence at least 90% identical to SEQ ID NO: 148 and a second portion comprising SEQ ID NO: 156;

(d) a first probe comprising a first portion comprising a nucleic acid sequence at least 90% identical to SEQ ID NO: 149 and a second portion comprising SEQ ID NO: 155, and a second probe comprising a first portion comprising a nucleic acid sequence at least 90% identical to SEQ ID NO: 150 and a second portion comprising SEQ ID NO: 156; and/or (e) a first probe comprising a first portion comprising a nucleic acid sequence at least 90% identical to SEQ ID NO: 152 and a second portion comprising SEQ ID NO: 155, and a second probe comprising a first portion comprising a nucleic acid sequence at least 90% identical to SEQ ID NO: 153 and a second portion comprising SEQ ID NO: 156.

5. The kit of claim 4, further comprising a third probe comprising a nucleic acid sequence at least 90% identical to any one of SEQ ID NOs: 143, 146, 151, or 154 and a detectable label.

6. The kit of claim 5, wherein the third probe comprises the nucleic acid sequence of any one of SEQ ID NOs: 143, 146, 151, or 154 and a detectable label.

7. The kit of claim 1, wherein at least one of the at least two probes is covalently linked to a substrate.

8. The kit of claim 7, wherein the substrate comprises a magnetic bead.

* * * * *

```
                            SEQUENCE LISTING

<160> NUMBER OF SEQ ID NOS: 160

<210> SEQ ID NO 1
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 1
tttttgaahm arytacttgt cratrgtraa tggca                              35

<210> SEQ ID NO 2
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 2
aayyayttgt caaygkyraa tggcarctca gcacc                              35

<210> SEQ ID NO 3
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 3
ccacaaaarg aaatgmtrct yccactdgtc carat                              35

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 4
acagtgtcac trtytacmcc acaraargat atrct                              35

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
ccacagaarg aratrctgct tccgctagcc cagat                              35

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
ccgtctggcc adgacca                                                  17
```

<210> SEQ ID NO 7
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 7
aaaattgcga aagcttatay aggcatrarr yyrat                      35

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8
gtccaccaya cyctrgyytc ytkyggycty cctct                      35

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 9
ccygargtrc cacaaaayac racaatactg ttyga                      35

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 10
ccatcaggcc atgagcctgt tccata                                26

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ccccatcagg ccatgagcct ga                                    22

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
trttacttgg gcataaaccc aatrttrgma ccatc                      35

<210> SEQ ID NO 13
<211> LENGTH: 35
<212> TYPE: DNA
<213> ORGANISM: Artificial Sequence
<220> FEATURE:

<223> OTHER INFORMATION: Synthetic oligonucleotide

<400> SEQUENCE: 13
ccacagaadg tractatact rttrctkgtc caaga                          35

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 14
cccgatccag gttcattgtc tagycc                                    26

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
tacttgtcta tgtcaaargg carbagagcg ccatc                          35

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
ctaccgctag tccatatggt yttytcyttr ggctg                          35

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
ccaacytgtg gtatcagaat yaacaccaca ra                             32

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
ctactagarg tccaaatgct tgtcctctct tctgg                          35

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
ctactwgavg tccaaatgct ygtcctctct tctgg                          35

```
<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
catcttatcg atgtcraakg gtagaattgc tccat                          35

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
catcttatcg atgtcrrakg gtagaattgc tccat                          35

<210> SEQ ID NO 22
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 22
aacatggaac taagcaytgt ttayyagtca ttgtg                          35

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 23
agtcattgtd ryyggraygg tgaaagctcc rctgta                         36

<210> SEQ ID NO 24
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 24
caaaacacag tggarctact ygargtccaa atgct                          35

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 25
gggacctyac trraaacacc acaraamaca gtgga                          35

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide
```

```
<400> SEQUENCE: 26
cctcttatca tttccarcca gaaacatgga                              30

<210> SEQ ID NO 27
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 27
ctgggacctc actggaaaca ccacaaaac                               29

<210> SEQ ID NO 28
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 28
tacttraagt agatgatttc agccccatca tgcca                        35

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 29
ctacttaaag tagatgatyt cwgcmccatc rtgcc                        35

<210> SEQ ID NO 30
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 30
atrctattgg aygtccamar tacactacty tcttt                        35

<210> SEQ ID NO 31
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 31
ctcccyctra tyarytcyac ataraaacaa ggatt                        35

<210> SEQ ID NO 32
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 32
ccaagatccc aatcgctcct tggatc                                  26

<210> SEQ ID NO 33
<211> LENGTH: 25
```

```
<212> TYPE: DNA
<213> ORGANISM: Artificial Sequence
<220> FEATURE:
<223> OTHER INFORMATION: Synthetic oligonucleotide

<400> SEQUENCE: 33
caccatcrtg ccaggaccat gatcc                                              25

<210> SEQ ID NO 34
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 34
awtttacgaa aagtattgra tytgtgcccc atcgg                                   35

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 35
ctcgtccacc aaacatactt ggcttcttch ggyct                                   35

<210> SEQ ID NO 36
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 36
cttcctctta tyarttcaac ataraaacag ggrtt                                   35

<210> SEQ ID NO 37
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 37
catacgtatt tagcctcttc gggtcttcct ctaat                                   35

<210> SEQ ID NO 38
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 38
actrttacty gyccaccaba crtayttrgc ctctt                                   35

<210> SEQ ID NO 39
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 39
```
ccacataggg caattaract rttacttgtc cacca                35

<210> SEQ ID NO 40
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 40
catagtgcaa ctaaactgtt rctcgtccac c                   31

<210> SEQ ID NO 41
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 41
cttccacata gggcaattag actgttrctt g                   31

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
ccggacccaa ctgggaatgg g                              21

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
aaccggaccc aactgggaat ggg                            23

<210> SEQ ID NO 44
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 44
atcttrtcga tgtcaaargg aagaatwgct ccatc               35

<210> SEQ ID NO 45
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 45
atggagctrc tdgargtcca kathgtykty tcttc               35

<210> SEQ ID NO 46
<211> LENGTH: 18
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: locked nucleic acid
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 46
ctccacacat yacaatgg                                                 18

<210> SEQ ID NO 47
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 47
tcttagagga agtactctat tttagcccca tcagg                              35

<210> SEQ ID NO 48
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 48
tcttagagga agtactctat ttyagcmcca tcwgg                              35

<210> SEQ ID NO 49
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 49
aattctgtrc tggaacacat ygatactatr ctatt                              35

<210> SEQ ID NO 50
<211> LENGTH: 35
<212> TYPE: DNA
<213> ORGANISM: Artificial Sequence
<220> FEATURE:
<223> OTHER INFORMATION: Synthetic oligonucleotide
```

<400> SEQUENCE: 50
ctggtccacc ayactttrtc ctcyttrggy ctycc					35

<210> SEQ ID NO 51
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 51
ccagttccat tgtccmagga attctgtrc					29

<210> SEQ ID NO 52
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 52
taaatgcata ytctgcattg yarygaycca ttaga					35

<210> SEQ ID NO 53
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 53
tctyagatrc atattctrca ytgyaaagac ccatt					35

<210> SEQ ID NO 54
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 54
atacatattc trcaytgtar mgamccattr gagca					35

<210> SEQ ID NO 55
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 55
agggagacta ayardacyag ggaactggcg actgt					35

<210> SEQ ID NO 56
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 56
gcccccaggg agacyarrar aacyardgaa ctggc					35

<210> SEQ ID NO 57
<211> LENGTH: 35

```
<212> TYPE: DNA
<213> ORGANISM: Artificial Sequence
<220> FEATURE:
<223> OTHER INFORMATION: Synthetic oligonucleotide

<400> SEQUENCE: 57
ccyagagaga ctavyagtac yrrhgagctg gcgac                              35

<210> SEQ ID NO 58
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 58
cacatccaga aactgaytgc ccccag                                       26

<210> SEQ ID NO 59
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 59
cacatccaga arctgattgc ccccag                                       26

<210> SEQ ID NO 60
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 60
atyctgcayt gcagagaycc rttrgarcac atcca                             35

<210> SEQ ID NO 61
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 61
atgattgcca rtgacargga rcctgchact gtagc                             35

<210> SEQ ID NO 62
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 62
tcccagctat catgattgcc agtgaca                                      27

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
```
ccagccatca tgattgccag tgaca                                           25

<210> SEQ ID NO 64
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 64
aatgcaaatg ttgcayctra tgttgcctyt ytggc                                35

<210> SEQ ID NO 65
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 65
tggcaaagga ratccayarg atccartcyt tgtatcc                              37

<210> SEQ ID NO 66
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 66
ttgtttawtg cttcatcyct gtataygtma tggtca                               36

<210> SEQ ID NO 67
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 67
cccacataat raaacccaat agaacaacgc                                      30

<210> SEQ ID NO 68
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 68
caaagcaara agcatgatat ggcaaagga                                       29

<210> SEQ ID NO 69
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 69
aaatrcaaat ctgrcacckg akgtttccrt tytga                                35

<210> SEQ ID NO 70
<211> LENGTH: 35
<212> TYPE: DNA
<213> ORGANISM: Artificial Sequence

```
<220> FEATURE:
<223> OTHER INFORMATION: Synthetic oligonucleotide

<400> SEQUENCE: 70
agtgcaacga ryaaraagca tgatatggaa aagga                               35

<210> SEQ ID NO 71
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 71
tccaaagrat rrtgtcyttg tayccctggg tcaat                               35

<210> SEQ ID NO 72
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 72
caccggatgt ttccrttctg acaagccc                                      28

<210> SEQ ID NO 73
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 73
caaaaagcat gayatggaga atgaaatcca                                    30

<210> SEQ ID NO 74
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 74
accttrtcrt araggttcyt dacatttgag tcatg                              35

<210> SEQ ID NO 75
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 75
accttdtcrt aragrttcyt dacatttgag tcatg                              35

<210> SEQ ID NO 76
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 76
tagatgcaaa ttctgcactg caatgaycca ttrga                              35
```

<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 77
tagatgcaaa yyctgcactg caatgaycca ttrga                             35

<210> SEQ ID NO 78
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 78
actccattta grctgcakag cttyccrttg tgtgc                             35

<210> SEQ ID NO 79
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 79
actccattta grcygcakag cttyccrttg tgtgy                             35

<210> SEQ ID NO 80
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 80
accagaagtt cagcattata agtccaraca tctag                             35

<210> SEQ ID NO 81
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 81
acyarragtt cwgcrttata agtccaraca tctag                             35

<210> SEQ ID NO 82
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 82
ccagctayca tgattgccag tgctagggaa ctcgc                             35

<210> SEQ ID NO 83
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 83
ccagcyayca tgattgccag trctarggaa ctcrc                            35

<210> SEQ ID NO 84
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 84
tctgtcgagt tgtttgcatg gtaaccaatg caaat                            35

<210> SEQ ID NO 85
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 85
gtcgagttrt ttgcatggta accaatgcaa atytg                            35

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 86
ctctcatttt ccatgagaac c                                           21

<210> SEQ ID NO 87
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 87
tagagttctc tcattttcca tgagaacyar aagttcagc                        39

<210> SEQ ID NO 88
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 88
catccaaaar gatagaccag ctaycatgat tg                               32

<210> SEQ ID NO 89
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 89
cagtracatt cttttccatt attgtgtcaa cctg                             34

<210> SEQ ID NO 90

<210> SEQ ID NO 90
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 90
caytgcattg aacyatttga acacatccaa agacc                      35

<210> SEQ ID NO 91
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 91
atyctgcayt gcattgarcy attygarcac atcca                      35

<210> SEQ ID NO 92
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 92
gtactataaa tggcaagdat ttgatacacr ycaaa                      35

<210> SEQ ID NO 93
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 93
ctataaatrg caagratytg atayacaccr agrtt                      35

<210> SEQ ID NO 94
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 94
ctgctcgata ycgtactat                                        19

<210> SEQ ID NO 95
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 95
tatatacaaa tagtgcacyg catgtttcca ttctt                      35

<210> SEQ ID NO 96
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 96
ttcayrcaya tgaarryaag gcccattrca atggc        35

<210> SEQ ID NO 97
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 97
gattatgtcy ttgtatccac tactcaaytt cactg        35

<210> SEQ ID NO 98
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 98
agtatyaymt ctttrtarcc rctgctyart ttgac        35

<210> SEQ ID NO 99
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 99
catgatgccc cgaagctaaa ccataagatt              30

<210> SEQ ID NO 100
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 100
catgatgccc cgaagctaaa ccaaagtatc              30

<210> SEQ ID NO 101
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 101
aatacagaac atgcatctac aagatccatt ytgca        35

<210> SEQ ID NO 102
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 102
gactggccgc cacygtactg taratgctra gaatt        35

<210> SEQ ID NO 103
<211> LENGTH: 27
<212> TYPE: DNA

```
<213> ORGANISM: Artificial Sequence
<220> FEATURE:
<223> OTHER INFORMATION: Synthetic oligonucleotide

<400> SEQUENCE: 103
acctccagca atcaggattg ccaagca                                        27

<210> SEQ ID NO 104
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 104
atgttgcryc tgcahgahcc attdgacatr gcccaga                             37

<210> SEQ ID NO 105
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 105
tcatttgaat gctgraahcc rtaccagccw gcaac                               35

<210> SEQ ID NO 106
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 106
cchtcagayt ccagyttday yccytctatt ttctg                               35

<210> SEQ ID NO 107
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 107
cawccbccyt ctatraaycc agctatrgca ccaaa                               35

<210> SEQ ID NO 108
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 108
atcctcacca tttattcgac tgtcgcctca                                     30

<210> SEQ ID NO 109
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 109
cttgcratgg ggtttgctgc cttc                                           24
```

<210> SEQ ID NO 110
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 110
atagctggat tcatagaagg aggttggccw gg                                32

<210> SEQ ID NO 111
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 111
taaatrcaga ttgtgcatcg catgttycca ttyytca                           37

<210> SEQ ID NO 112
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 112
gccccgaagc taaaccavar katdayrtcy ttrta                             35

<210> SEQ ID NO 113
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 113
acaagyccca tgatgacagc caaaag                                       26

<210> SEQ ID NO 114
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 114
caagacccat gacaacggct agaagaaca                                    29

<210> SEQ ID NO 115
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 115
acaagaccca twacaacggc tagaagaaca aa                                32

<210> SEQ ID NO 116
<211> LENGTH: 35
<212> TYPE: DNA
<213> ORGANISM: Artificial Sequence
<220> FEATURE:

<223> OTHER INFORMATION: Synthetic oligonucleotide

<400> SEQUENCE: 116
caattytaaa tgcaaatgkt acatctrcat gaycc        35

<210> SEQ ID NO 117
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 117
aaattgacag tattttrtav acrttsccry trgaa        35

<210> SEQ ID NO 118
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 118
tctartytca cyccytcrat ytcctgrcgr ttgat        35

<210> SEQ ID NO 119
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 119
ctgtcrattt acagctgcat tgcaagcagt ctc        33

<210> SEQ ID NO 120
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 120
atacagaaag tacaacgaac atttccatty tgaca        35

<210> SEQ ID NO 121
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 121
actaagcttg argcaacrct gctgtagatg ctca        34

<210> SEQ ID NO 122
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 122
ccgaaaatga aaccccaat aatcatgagc        30

```
<210> SEQ ID NO 123
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 123
atacaaacat tgaatcgrca gytyccayta ctaca                                  35

<210> SEQ ID NO 124
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 124
acttatatac aratattraa hcggcarytk ccact                                  35

<210> SEQ ID NO 125
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 125
actgcttgcr atgcarctgt awatygayar tgctt                                  35

<210> SEQ ID NO 126
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 126
caggcccaca tratgaaaga gagtatgagt c                                      31

<210> SEQ ID NO 127
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 127
attgaaycgg caattgccac taytacatg                                         29

<210> SEQ ID NO 128
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 128
catgyccaca tgatgaatgc aagtatgag                                         29

<210> SEQ ID NO 129
<211> LENGTH: 35
<212> TYPE: DNA
<213> ORGANISM: Artificial Sequence
<220> FEATURE:
<223> OTHER INFORMATION: Synthetic oligonucleotide
```

<400> SEQUENCE: 129
caagcccawa gaacaaatcc caraatcagt gccac                              35

<210> SEQ ID NO 130
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 130
ttgttratgg cytcatccct rtagatgttg tgrtc                              35

<210> SEQ ID NO 131
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 131
acaaagcatg acatggagaa agaaatccac ag                                 32

<210> SEQ ID NO 132
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 132
cgcagattcc cgtttttcac acacatgaaa ataag                              35

<210> SEQ ID NO 133
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 133
tcctgtcgat attcagtgtg attgtaagtr ttrtt                              35

<210> SEQ ID NO 134
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 134
catgatgccc cgaagctaaa ccatagtaty ac                                 32

<210> SEQ ID NO 135
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: n is a, c, g, or t

<400> SEQUENCE: 135
tatatacama cattraaccg gcaattncca ytgct                              35

<210> SEQ ID NO 136
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 136
attgtcttca gtcttcaayt tkatcccttc rattt                    35

<210> SEQ ID NO 137
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 137
ctgcttgcaa tgcarctata aattgmcagk ayytt                    35

<210> SEQ ID NO 138
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 138
tgagtcctac cagaacaaca ctgcttgca                           29

<210> SEQ ID NO 139
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 139
catgcccaca ttatraatgc aagtatgaga cc                       32

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
tatgagaccy accatcacaa                                     20

<210> SEQ ID NO 141
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 141
cattyccatt dagggcatty tggacaaavc gtcta                    35

<210> SEQ ID NO 142
<211> LENGTH: 35
<212> TYPE: DNA
<213> ORGANISM: Artificial Sequence
<220> FEATURE:

```
<223> OTHER INFORMATION: Synthetic oligonucleotide

<400> SEQUENCE: 142
cgctcactgg gcacggtgag cgtraayaca aaycc                              35

<210> SEQ ID NO 143
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 143
ctacgctgca gtcctcgctc actgg                                        25

<210> SEQ ID NO 144
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: n is a, c, g, or t

<400> SEQUENCE: 144
gggcattytg gayaaancgt ctacgctgca gtcc                              34

<210> SEQ ID NO 145
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 145
tcactgggca cggtgagcgt raayacaaah ccyaa                             35

<210> SEQ ID NO 146
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 146
ctacgctgca gtcctcgctc actgg                                        25

<210> SEQ ID NO 147
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 147
ttrggdtttg trttyacgct caccgtgccc agtga                             35

<210> SEQ ID NO 148
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

```
<222> LOCATION: (18)..(18)
<223> OTHER INFORMATION: n is a, c, g, or t

<400> SEQUENCE: 148
ggactgcagc gtagacgntt trtccaraat gccct                      35

<210> SEQ ID NO 149
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 149
gagtatyttr gcaacytgrg gagaggcatt tgcta                      35

<210> SEQ ID NO 150
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 150
garggyccga gyacatcact gagcccracr gatag                      35

<210> SEQ ID NO 151
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 151
tctctagcag tgggacagcc tgctatcc                              28

<210> SEQ ID NO 152
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 152
ctgctcraaa yccagrgcra crtagcacag cttct                      35

<210> SEQ ID NO 153
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 153
tagatgggca cagtgtgggt aacrccatca ccaga                      35

<210> SEQ ID NO 154
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 154
caggtcacgg ccagccagat cc                                    22
```

```
<210> SEQ ID NO 155
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 155
cgaccaggaa acagctatga cc                                              22

<210> SEQ ID NO 156
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 156
ttcactggcc gtcgttttac aac                                             23

<210> SEQ ID NO 157
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 157
tgttgtaaaa cgacggccag tga                                             23

<210> SEQ ID NO 158
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 158
cgaccaggaa acgactatga cc                                              22

<210> SEQ ID NO 159
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 159
gtcgagttrt ttgcatgrta accaatgcaa atytg                                35

<210> SEQ ID NO 160
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 160
cagtracatt cttttccatt atygtgtcaa cctg                                 34
```